United States Patent
Gu et al.

(10) Patent No.: US 10,752,780 B2
(45) Date of Patent: Aug. 25, 2020

(54) CHROMOPHORES FOR PHOTOCHROMIC COMPOSITIONS USEFUL FOR THREE DIMENSIONAL DISPLAY APPLICATIONS

(71) Applicant: Nitto Denko Corporation, Osaka (JP)

(72) Inventors: Tao Gu, San Diego, CA (US); Bogumila Rachwal, Oceanside, CA (US); Ozair Siddiqui, Murrieta, CA (US); Stanislaw Rachwal, Oceanside, CA (US); Isamu Kitahara, San Diego, CA (US); Sergey Simavoryan, San Diego, CA (US); Peng Wang, San Diego, CA (US); Michiharu Yamamoto, San Jose, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 16/004,152

(22) Filed: Jun. 8, 2018

(65) Prior Publication Data
US 2018/0291207 A1    Oct. 11, 2018

Related U.S. Application Data

(62) Division of application No. 15/306,428, filed as application No. PCT/US2015/026897 on Apr. 21, 2015, now Pat. No. 10,077,362.
(Continued)

(51) Int. Cl.
*C09B 62/008* (2006.01)
*G02B 1/04* (2006.01)
(Continued)

(52) U.S. Cl.
CPC ........ *C09B 62/0081* (2013.01); *C07C 255/65* (2013.01); *C07D 213/42* (2013.01); *C07D 231/12* (2013.01); *C07D 239/26* (2013.01); *C07D 249/06* (2013.01); *C07D 261/08* (2013.01); *C08K 5/23* (2013.01);
(Continued)

(58) Field of Classification Search
CPC ... G02F 1/29; C09B 62/0081; C09B 62/0088; C09B 29/0003; C09B 29/0011; C09B 29/0807; C09B 62/0083; C09B 62/0086; G02B 1/04; G02B 5/23; G11B 7/244; G11B 7/245; G11B 7/24044; C07C 255/65; C09K 19/601; C09D 133/12; C08L 33/12;
(Continued)

(56) References Cited

FOREIGN PATENT DOCUMENTS

| JP | 762594 | * | 3/1995 | ............... G02F 1/15 |
| WO | WO2012/018342 A1 | * | 2/2012 | ............... G02F 1/29 |

* cited by examiner

*Primary Examiner* — Bijan Ahvazi
(74) *Attorney, Agent, or Firm* — K&L Gates LLP; Louis C. Cullman; Hal Gibson

(57) ABSTRACT

Described herein are novel azo-benzene type chromophores. The chromophores are useful in photochromic compositions comprising a polymer matrix and a chromophore, wherein the chromophore is a novel azo-benzene type structure. The photochromic composition is photoresponsive upon irradiation by at least one wavelength of laser light across the visible light spectrum. Photochromic devices which comprise the novel azo-benzene type chromophore compound show significantly higher photoinduced birefringence, higher diffraction efficiency, and brighter images than devices that comprise well known azo-benzene chromophores. The photochromic composition may include a liquid crystal.

18 Claims, 2 Drawing Sheets

Related U.S. Application Data

(60) Provisional application No. 61/983,297, filed on Apr. 23, 2014.

(51) Int. Cl.
| | | |
|---|---|---|
| *G02B 5/23* | (2006.01) |
| *C09D 133/12* | (2006.01) |
| *C08L 33/12* | (2006.01) |
| *G11B 7/24044* | (2013.01) |
| *C08K 5/23* | (2006.01) |
| *G11B 7/244* | (2006.01) |
| *G11B 7/245* | (2006.01) |
| *C09K 19/60* | (2006.01) |
| *C07C 255/65* | (2006.01) |
| *C07D 231/12* | (2006.01) |
| *C07D 239/26* | (2006.01) |
| *C07D 249/06* | (2006.01) |
| *C07D 261/08* | (2006.01) |
| *C07D 213/42* | (2006.01) |
| *C09B 29/01* | (2006.01) |
| *C09B 29/08* | (2006.01) |

(52) U.S. Cl.
CPC .......... *C08L 33/12* (2013.01); *C09B 29/0003* (2013.01); *C09B 29/0011* (2013.01); *C09B 29/0807* (2013.01); *C09B 62/0083* (2013.01); *C09B 62/0086* (2013.01); *C09B 62/0088* (2013.01); *C09D 133/12* (2013.01); *C09K 19/601* (2013.01); *G02B 1/04* (2013.01); *G02B 5/23* (2013.01); *G11B 7/244* (2013.01); *G11B 7/245* (2013.01); *G11B 7/24044* (2013.01)

(58) Field of Classification Search
CPC ...... C08K 5/23; C07D 231/12; C07D 239/26; C07D 213/42; C07D 249/06; C07D 261/08
USPC .............. 252/301.16, 301.35, 586; 264/1.37; 359/244
See application file for complete search history.

CHROMOPHORES FOR PHOTOCHROMIC COMPOSITIONS USEFUL FOR THREE DIMENSIONAL DISPLAY APPLICATIONS

CROSS-REFERENCE TO RELATED APPLICATIONS

This patent application is a divisional of U.S. application Ser. No. 15/306,428, filed Oct. 24, 2016, which is a national phase of PCT/US2015/026897, filed on Apr. 21, 2015, which claims the benefit of priority to U.S. Provisional Patent Application No. 61/983,297, filed Apr. 23, 2014. The foregoing applications are fully incorporated herein by reference for all purposes.

BACKGROUND

Field

The embodiments generally relate to chromophore compounds comprising novel azo-benzene type structures. The chromophores are useful in photochromic compositions comprising a polymer matrix and at least chromophore, wherein the chromophore comprises a novel azo-benzene type structure. The photochromic composition is photoresponsive upon irradiation by at least one wavelength of light across the visible light spectrum. Photochromic devices which comprise the novel azo-benzene type chromophore compound show photoresponsive properties, including high diffraction efficiency, high photoinduced birefringence, and fast response time. The photochromic composition may include a liquid crystal.

Description of the Related Art

Holographic memories have attracted much attention due to their potential use in three-dimensional display applications and high capacity data storage mediums. There are several different types of optical information recording media capable of storing holographic information, which include photorefractive materials and photochromic materials. Both photochromic and photorefractive materials have many promising applications, such as high-density optical data storage, dynamic holography, optical image processing, phase conjugated mirrors, optical computing, parallel optical logic, and pattern recognition. Particularly, high diffraction efficiency can contribute significantly to high-density optical data storage or holographic display applications.

Originally, the photorefractive effect was found in a variety of inorganic electro-optical (EO) crystals, such as $LiNbO_3$. In these materials, the mechanism of a refractive index modulation by the internal space-charge field is based on a linear electro-optical effect. In 1990 and 1991, the first organic photorefractive crystal and polymeric photorefractive materials were discovered and reported. Some relevant information related to these materials can be found in U.S. Pat. No. 5,064,264, the contents of which are hereby incorporated by reference in their entirety. Organic photorefractive materials offer many advantages over the original inorganic photorefractive crystals, such as large optical nonlinearities, low dielectric constants, low cost, lightweight, structural flexibility, and ease of device fabrication. However, researchers have found that large scale organic photorefractive devices easily breakdown, and they have been unable to design organic photorefractive compositions that do not exhibit this high breakdown issue.

Similarly, photochromic materials have also been around for decades. The photochromic effect occurs when a compounds optical properties, such as absorption, emission, reflection, birefringence or scattering, are reversibly modified by means of a photoinduced physical and/or chemical processes. Typical organic photochromic materials are polymers having an azo-benzene structure. Relevant literature includes U.S. Pat. Nos. 5,641,846, 7,951,922, and S. Xie, A. Natansohn and P. Rochon, Chem. Rev., vol. 5 (1993) p. 403-411, *"Recent Development in Aromatic Azo Polymers Research"*, T. Bieringer, R. Wuttke, D. Haarer, U. Gesner and J. Rubner, Macromol. Chem. Phys., vol. 196 (1995) p. 1375-1390, *"Relaxation of holographic gratings in liquid-crystalline side chain polymers with azo chromophores"*, and A. Natansohn and P. Rochon, ACS Symposium Series, vol. 672 (1997) p. 236-250, "Azobenzene-containing polymers: digital and holographic storage" and A. Natansohn, P. Rochon, X. Meng, C. Barrett, T. Buffeteau, S. Bonenfant and M. Pezolet, Macromolecules, vol. 31 (1998) p. 1155-1161, *"Molecular addressing Selective photoinduced cooperative motion of polar ester groups in copolymers containing azobenzene groups"*.

The photochromic composition may be made by mixing molecular components that provide desirable individual properties into a host polymer matrix. However, many of the previously prepared compositions failed to show good photochromic performances, (e.g., high diffraction efficiency, fast response time and long-term stability). Efforts have been made, therefore, to provide compositions which show high diffraction efficiency, fast response time and long stability. However, a photochromic composition that provides all the various properties required for practical application such as sensitivity, response speed, long-term storage stability, and repeatability has not yet been found.

SUMMARY

A primary objective of the present disclosure is to provide novel chromophores comprising azo-benzene type structures. The chromophores are useful in photochromic compositions to provide good optical information recording properties such as fast response time, high diffraction efficiency, and high transmittance. In some embodiments, the chromophore may be used in a photochromic composition. In some embodiments, a photochromic composition comprises a polymer matrix and a chromophore. The chromophore is a novel azo-benzene type compound. The inventors have discovered that the photochromic composition, as disclosed herein, provides fast response time, high diffraction efficiency, and high transmittance.

In some embodiments, a chromophore is represented by formula (I-a), (I-b), (I-c), (I-d), (I-e) or (I-f):

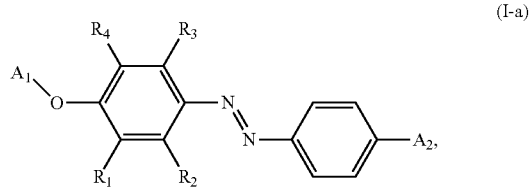

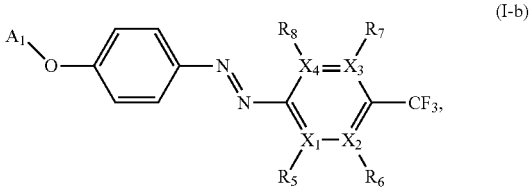

-continued

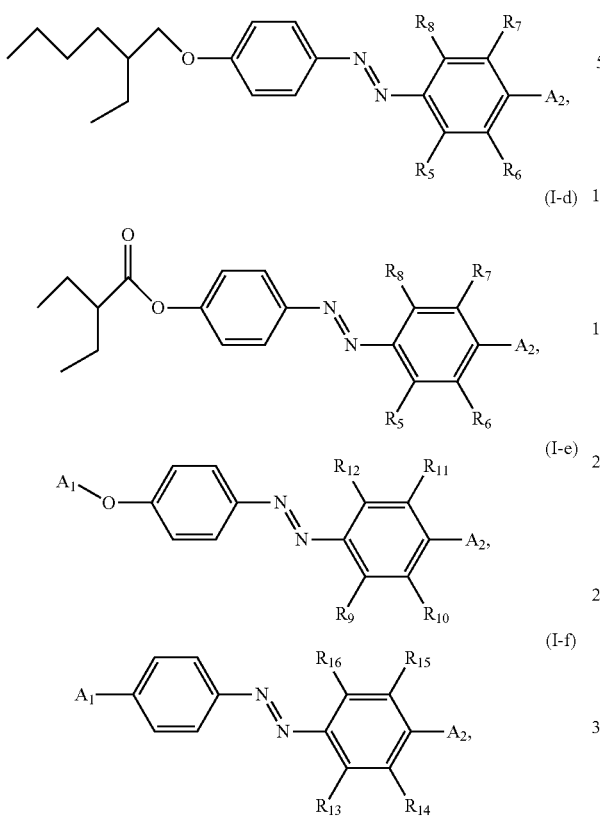

wherein $A_1$ is optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether and/or any combination of said groups. In some embodiments, $A_2$ is selected from —CN, —CF$_3$, and —NO$_2$. In some embodiments, $X_1$-$X_4$ are each independently selected from C or N, provided that at least one of $X_1$-$X_4$ is N. In some embodiments, $R_1$-$R_4$ are each independently selected from the group consisting of hydrogen, —F, —CN, or —CF$_3$, provided that at least one of $R_1$-$R_4$ is not hydrogen. In some embodiments, $R_5$-$R_8$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —CF$_3$, and/or any combination of said groups. In some embodiments, $R_9$-$R_{12}$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —CF$_3$, and/or any combination of said groups, provided that at least one of $R_9$-$R_{12}$ is not hydrogen.

In some embodiments, $R_{13}$-$R_{16}$ are each independently selected from hydrogen, —F, —CN, and —CF$_3$, provided that at least one of $R_{13}$-$R_{16}$ is not hydrogen.

In some embodiments, a chromophore represented by formula (II):

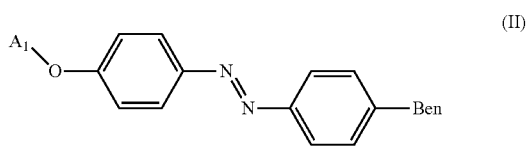

wherein Ben is

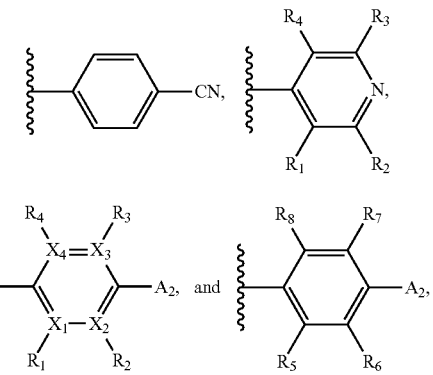

wherein $A_1$ is selected from optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, and/or any combination of said groups. In some embodiments, $A_2$ is selected from —H, —F, —CN, —CF$_3$, and —NO$_2$. In some embodiments, $X_1$-$X_4$ are each independently selected from C or N, provided that at least one of $X_1$-$X_4$ is N. In some embodiments, $R_1$-$R_8$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —CF$_3$, and/or any combination of said groups, provided that at least one of $R_5$-$R_8$ is not hydrogen.

A chromophore represented by formulae (III):

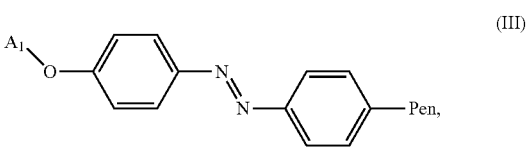

wherein Pen is

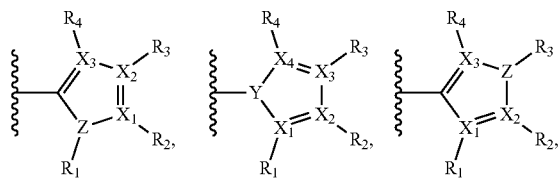

wherein $A_1$ is selected from optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, and/or any combination of said groups. In some embodiments, $X_1$-$X_4$ are each independently selected from C and N. In some embodiments, Z is selected from S, O, C, and N. In some embodiments, Y is selected from C and N. In some embodiments, $R_1$-$R_4$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —CF$_3$, —NO$_2$, —Br, and/or any combination of said groups.

Another aspect includes a photochromic composition. In some embodiments, a photochromic composition comprises a polymer matrix and a chromophore. In some embodiments, the chromophore comprises a moiety as represented by any of formulae (I-a), (I-b), (I-c), (I-d), (I-e), (I-f), (II), and (III).

The photochromic composition may include a liquid crystal, which can provide additional photoresponse. In some embodiments, addition of a liquid crystal to the photochromic composition may provide an increase in the photoinduced birefringence.

In an embodiment, the polymer matrix may also comprise a substance selected from the group consisting of polyethylene terephthalate, polyacrylate, polymethacrylate, polyvinyl carbazole, polymethyl methacrylate, polyvinyl butyral, ethylene vinyl acetate, ethylene tetrafluoroethylene, polyimide, amorphous polycarbonate, polystyrene, siloxane sol-gel, polyurethane, and combinations thereof. In an embodiment, the polymer may also comprise at least a repeating unit including a moiety selected from the group consisting of the carbazole moiety, tetraphenyl diaminobiphenyl moiety, and triphenylamine moiety. In some embodiments, the composition can be used for holographic data storage, as image recording materials, and in optical devices.

Some embodiments provide a composition configured to be photoresponsive upon irradiation by at least a first laser having a first wavelength in the visible light spectrum. Some embodiments provide a composition configured to be photoresponsive upon irradiation by at least a first laser having a first wavelength in the visible light spectrum and a second laser having a second wavelength in the visible light spectrum. The composition can be configured to be photoresponsive upon irradiation with a third laser having a third wavelength in the visible light spectrum, such that the third laser is different from the first laser and the second laser, wherein the third laser is selected from a blue laser, a green laser, and a red laser. In an embodiment, the composition is configured to be photoresponsive by each of a blue laser, a green laser, and a red laser. For example, the composition can be configured to be photoresponsive upon irradiation with a red laser, a green laser, and/or a blue laser, by the selection and incorporation of appropriate chromophore and polymer. In an embodiment, the composition is configured to be photoresponsive upon irradiation with a red laser, a green laser, and a blue laser, by the selection and incorporation of appropriate chromophore, liquid crystalline compound, and polymer.

The compositions described herein have great utility in a variety of optical applications, including holographic storage, optical correlation, phase conjugation, non-destructive evaluation, and imaging.

These and other embodiments are described in greater detail below.

DETAILED DESCRIPTION

Figure 1:
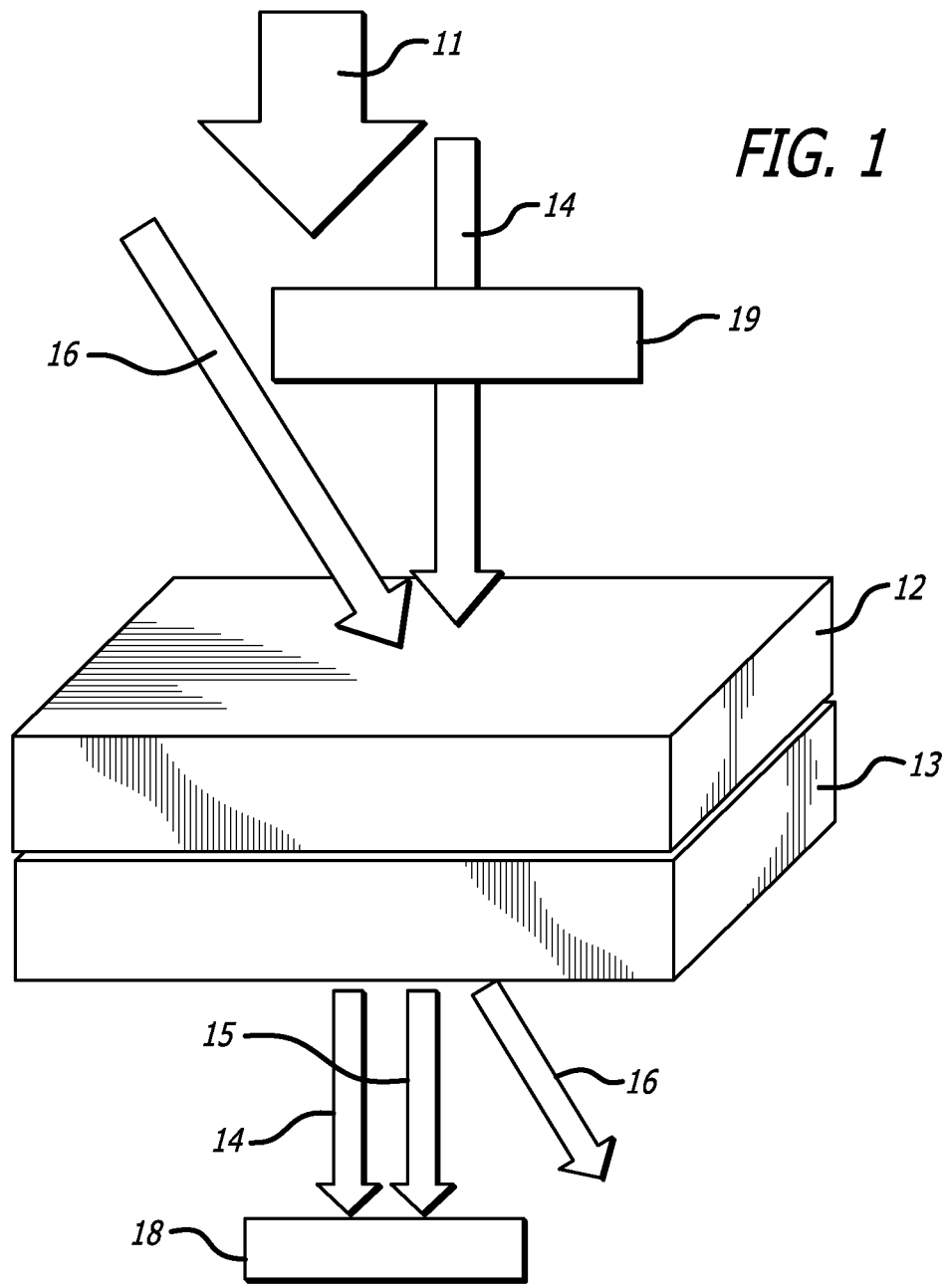
FIG. 1 is a schematic depiction illustrating a hologram recording system with a photochromic composition.

Some embodiments include a chromophore compound with a novel azo-benzene type structure. The azo-benzene chromophores, described herein, may be useful in a variety of applications. In some embodiments, the chromophore is useful in photochromic compositions. In some embodiments, a photochromic composition comprises a polymer matrix, and a chromophore, wherein the chromophore is an azo-benzene derivative, and wherein the photochromic composition is photoresponsive upon irradiation by at least one wavelength of laser light across the visible light spectrum. The inventors have discovered that the photochromic composition comprising the novel azo-benzene derivative chromophore, as disclosed herein, provides good photoresponse, such as high photoinduced birefringence and fast response time. The photochromic compositions of the present application provide significantly improved photoresponsive properties which may be useful in a variety of optical applications including three dimensional displays, holographic data storage, optical correlation, phase conjugation, non-destructive evaluation, and imaging.

The term "alkyl" used herein refers to a branched or straight fully saturated acyclic aliphatic hydrocarbon group (i.e. composed of carbon and hydrogen containing no double or triple bonds). Alkyls include, but are not limited to, methyl, ethyl, propyl, isopropyl, butyl, isobutyl, tertiary butyl, pentyl, hexyl, and the like.

The term "heteroalkyl" used herein refers to an alkyl group comprising one or more heteroatoms. When two or more heteroatoms are present, they may be the same or different. Examples of heteroalkyl groups include, but are not limited to, $CH_2$—OH, —$OC_nH_{2n+1}$, where n is any integer greater than or equal to 1.

The term "cycloalkyl" used herein refers to saturated aliphatic ring system moiety having three to twenty carbon atoms including, but not limited to, cyclopropyl, cyclopentyl, cyclohexyl, cycloheptyl, and the like.

The term "alkenyl" used herein refers to a monovalent straight or branched chain moiety of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain moiety of from two to twenty carbon atoms containing a carbon triple bond including, but not limited to, 1-propynyl, 1-butynyl, 2-butynyl, and the like.

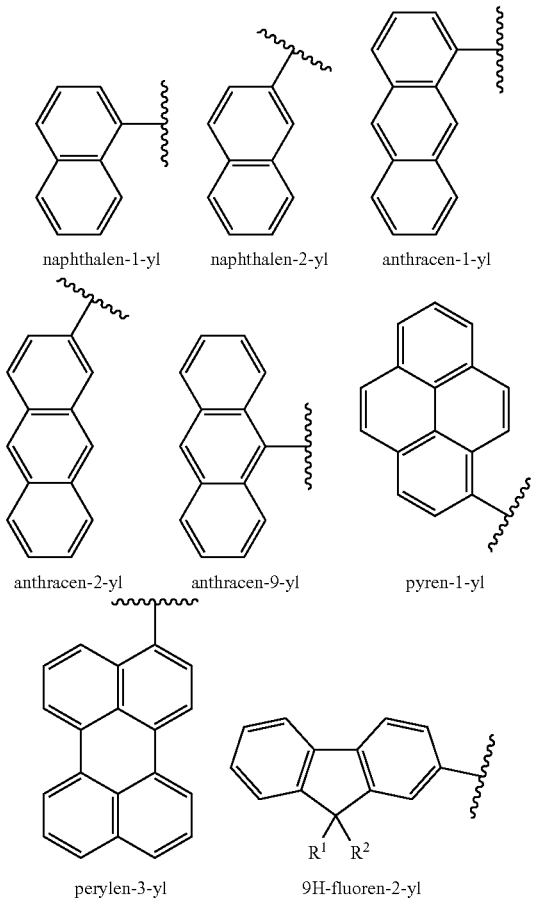

naphthalen-1-yl   naphthalen-2-yl   anthracen-1-yl anthracen-2-yl   anthracen-9-yl   pyren-1-yl perylen-3-yl   9H-fluoren-2-yl The term "aryl" used herein refers to homocyclic aromatic moiety whether one ring or multiple fused rings. Examples of aryl groups include, but are not limited to, phenyl, naphthyl, phenanthrenyl, naphthacenyl, fluorenyl, pyrenyl, and the like.

The term "alkaryl" or "alkylaryl" used herein refers to an alkyl-substituted aryl moiety. Examples of alkaryl include, but are not limited to, ethylphenyl, 9,9-dihexyl-9H-fluorene, and the like.

The term "aralkyl" or "arylalkyl" used herein refers to an aryl-substituted alkyl moiety. Examples of aralkyl include, but are not limited to, phenylpropyl, phenylethyl, and the like.

The term "heteroaryl" used herein may also refer to an aromatic ring system moiety in which one or more ring atoms are heteroatoms, whether one ring or multiple fused rings. When two or more heteroatoms are present, they may be the same or different. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyridazinyl, pyrimidinyl, pyrazinyl, pyrrolyl, oxazolyl, indolyl, thiazyl, and the like. Further examples of substituted and unsubstituted heteroaryl rings include:

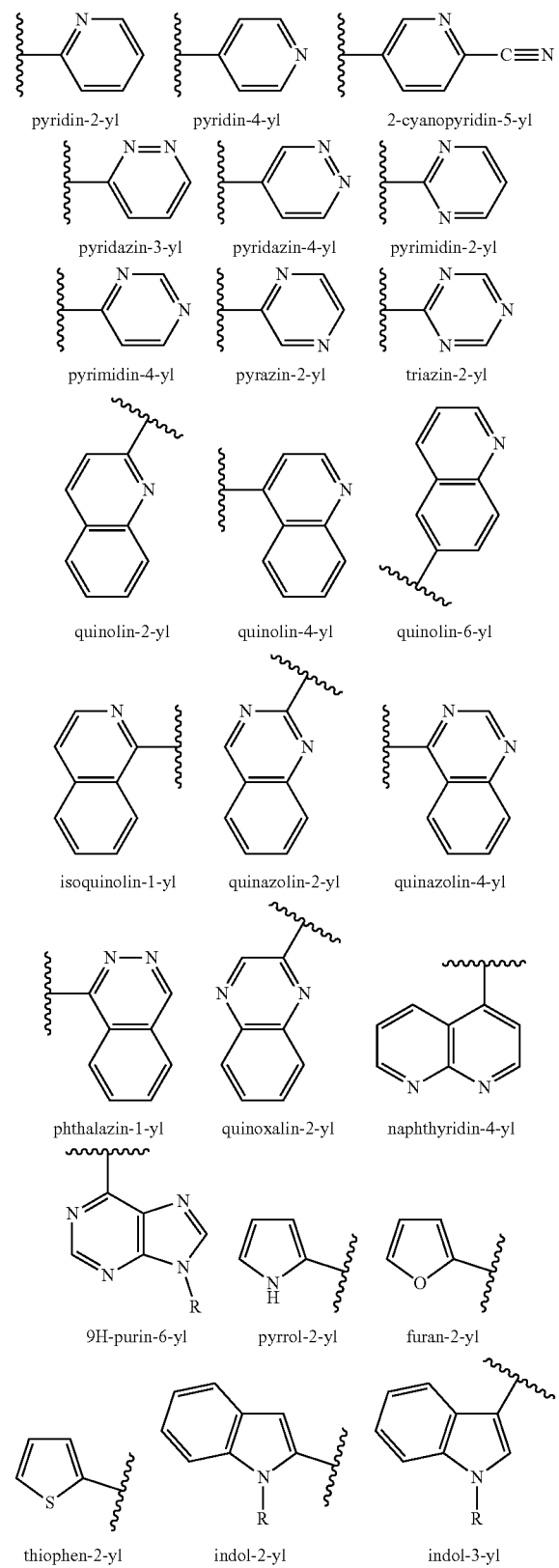

pyridin-2-yl   pyridin-4-yl   2-cyanopyridin-5-yl pyridazin-3-yl   pyridazin-4-yl   pyrimidin-2-yl pyrimidin-4-yl   pyrazin-2-yl   triazin-2-yl quinolin-2-yl   quinolin-4-yl   quinolin-6-yl isoquinolin-1-yl   quinazolin-2-yl   quinazolin-4-yl phthalazin-1-yl   quinoxalin-2-yl   naphthyridin-4-yl 9H-purin-6-yl   pyrrol-2-yl   furan-2-yl thiophen-2-yl   indol-2-yl   indol-3-yl

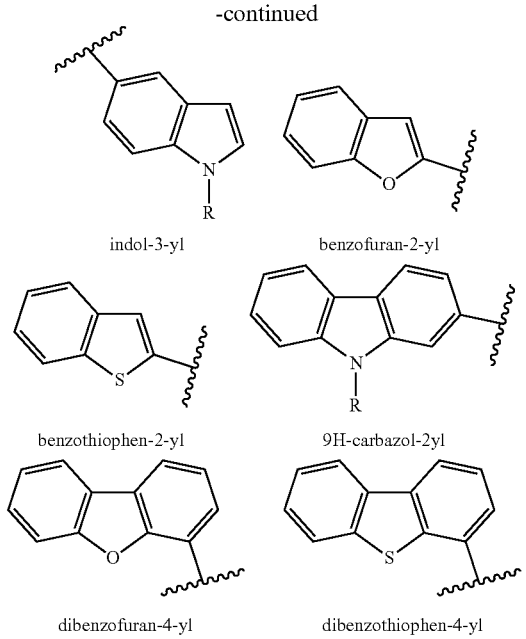

indol-3-yl
benzofuran-2-yl
benzothiophen-2-yl
9H-carbazol-2yl
dibenzofuran-4-yl
dibenzothiophen-4-yl The term "alkoxy" used herein refers to straight or branched chain alkyl moiety covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "heteroatom" used herein, is any atom that is not hydrogen or carbon. Typical heteroatoms include but are not limited to S (sulfur), N (nitrogen), O (oxygen), P (phosphorous), Cl (chlorine), Br (bromine), I (iodine), F (fluorine), etc.

The term "cyclic amino" used herein refers to either secondary or tertiary amines in a cyclic moiety. Examples of cyclic amino groups include, but are not limited to, aziridinyl, piperidinyl, N-methylpiperidinyl, and the like.

The term "cyclic imido" used herein refers to an imide in the moiety of which the two carbonyl carbons are connected by a carbon chain. Examples of cyclic imide groups include, but are not limited to, 1,8-naphthalimide, pyrrolidine-2,5-dione, 1H-pyrrole-2,5-dione, and the likes.

The term "aryloxy" used herein refers to an aryl moiety covalently bonded to the parent molecule through an —O— linkage.

The term "acyloxy" used herein refers to a moiety R—C(=O)O—.

The term "carbamoyl" used herein refers to —NHC(=O)R.

The term "keto" and "carbonyl" used herein refers to C=O.

The term "carboxy" used herein refers to —COOH.

The term "ester" used herein refers to C(=O)O.

The term "amido" used herein refers to —NRC(=O)R'.

The term "amino" used herein refers to —NR'R".

As used herein, a substituted group is derived from the unsubstituted parent structure in which there has been an exchange of one or more hydrogen atoms for another atom or group. When substituted, the substituent group(s) is (are) one or more group(s) individually and independently selected from $C_1$-$C_6$ alkyl, $C_1$-$C_6$ alkenyl, $C_1$-$C_6$ alkynyl, $C_3$-$C_7$ cycloalkyl (optionally substituted with halo, alkyl, alkoxy, carboxyl, haloalkyl, CN, —$SO_2$-alkyl, —$CF_3$, and —$OCF_3$), cycloalkyl geminally attached, $C_1$-$C_6$ heteroalkyl, $C_3$-$C_{10}$ heterocycloalkyl (e.g., tetrahydrofuryl) (optionally substituted with halo, alkyl, alkoxy, carboxyl, CN, —$SO_2$-alkyl, —$CF_3$, and —$OCF_3$), aryl (optionally substituted with halo, alkyl, aryl optionally substituted with $C_1$-$C_6$ alkyl, arylalkyl, alkoxy, aryloxy, carboxyl, amino, imido, amido (carbamoyl), optionally substituted cyclic imido, cylic amido, CN, —NH—C(=O)-alkyl, —$CF_3$, and —$OCF_3$), arylalkyl (optionally substituted with halo, alkyl, alkoxy, aryl, carboxyl, CN, —$SO_2$-alkyl, —$CF_3$, and —$OCF_3$), heteroaryl (optionally substituted with halo, alkyl, alkoxy, aryl, heteroaryl, aralkyl, carboxyl, CN, —$SO_2$-alkyl, —$CF_3$, and —$OCF_3$), halo (e.g., chloro, bromo, iodo and fluoro), cyano, hydroxy, optionally substituted cyclic imido, amino, imido, amido, —$CF_3$, $C_1$-$C_6$ alkoxy, aryloxy, acyloxy, sulfhydryl (mercapto), halo($C_1$-$C_6$)alkyl, $C_1$-$C_6$ alkylthio, arylthio, mono- and di-($C_1$-$C_6$)alkyl amino, quaternary ammonium salts, amino($C_1$-$C_6$)alkoxy, hydroxy($C_1$-$C_6$) alkylamino, amino($C_1$-$C_6$)alkylthio, cyanoamino, nitro, carbamoyl, keto (oxy), carbonyl, carboxy, glycolyl, glycyl, hydrazino, guanyl, sulfamyl, sulfonyl, sulfinyl, thiocarbonyl, thiocarboxy, sulfonamide, ester, C-amide, N-amide, N-carbamate, O-carbamate, urea and combinations thereof. Wherever a substituent is described as "optionally substituted" that substituent can be substituted with the above substituents.

Azo-benzene is an organic compound with the formula $C_{12}H_{10}N_2$. The photochromic effect occurs due to the photoisomerization of the cis and trans isomers, which can be switched with exposure to particular wavelengths of light. The wavelengths at which azobenzene isomerization occurs depends on the particular structure of each azo molecule. The general formula of azo-benzene is shown below.

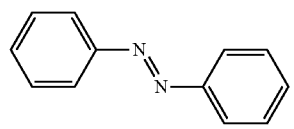

Described herein are novel azo-benzene derivative chromophore compounds.

Formula (I)

In some embodiments, a chromophore is represented by formula (I-a), (I-b), (I-c), (I-d), (I-e), or (I-f):

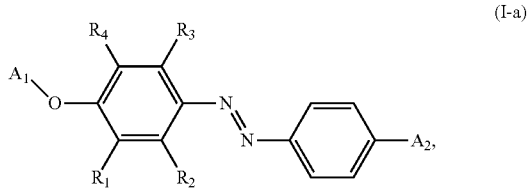

(I-a)

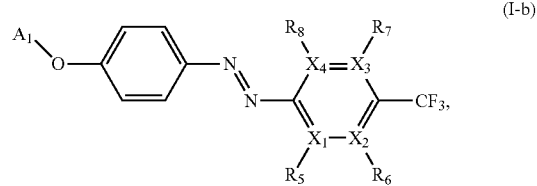

(I-b)

-continued

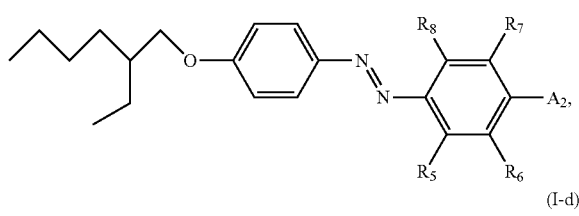
(I-c)

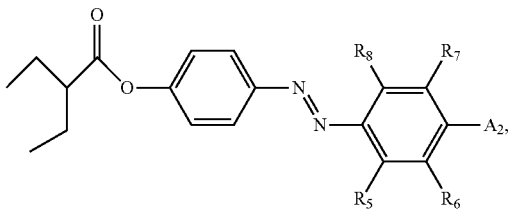
(I-d)

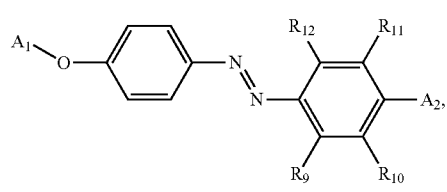
(I-e)

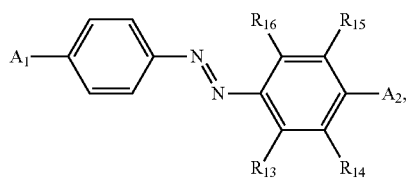
(I-f)

wherein $A_1$ is optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether and/or any combination of said groups. In some embodiments, $A_1$ is $C_{3-10}$ alkyl, such as $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or $C_{3-6}$ acyl, such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.

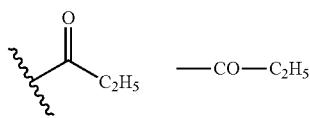

In some embodiments, $A_1$ of formula (I-a), (I-b), (I-e), and (I-f), is —$H_2C$—$CH_2$—$CH_2$—$CH_2$—$CH_2$—$CH_3$, —$CH_2$—$CH_2$—$CH_2$—$CH_3$,

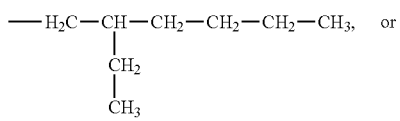 or

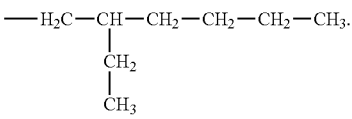

In some embodiments, $A_1$ is $H_2C$—$CH_2$—$CH_2$—$CH_2$—$CH_2$—$CH_3$. In some embodiments, $A_1$ is —$CH_2$—$CH_2$—$CH_2$—$CH_3$. In some embodiments, $A_1$ is —$H_2C$—CH—$CH_2$—$CH_2$—$CH_2$—$CH_3$.
         |
         $CH_2$
         |
         $CH_3$ In some embodiments, $A_1$ is $CH_3$

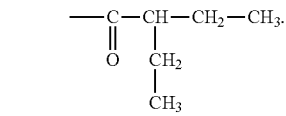

In some embodiments, such as compounds of formula (I-a). (I-c), (I-d), (I-e), or (I-f) $A_2$ is selected from —CN, —$CF_3$, and —$NO_2$. In some embodiments, $A_2$ is —CN. In some embodiments related to compounds of formula (I-c), $A_2$ is —CN. In some embodiments, $X_1$-$X_4$ are each independently selected from C or N, provided that at least one of $X_1$-$X_4$ is N. With respect to formula (I-a), in some embodiments, $R_1$-$R_4$ are each independently hydrogen, —F, —CN, or —$CF_3$, provided that $R_1$ or $R_2$ is not hydrogen.

With respect to formula (I-b), (I-c), or (I-d), in some embodiments, $R_5$-$R_8$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —$CF_3$, and/or any combination of said groups.

With respect to formula (I-b), (I-c), or (I-d), in some embodiments, $R_5$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_5$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_5$ is H. In some embodiments related to compounds of formula (I-c), $R_5$ is H.

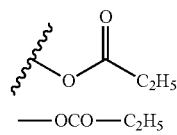
—OCO—$C_2H_5$

With respect to formula (I-b), (I-c), or (I-d), in some embodiments, $R_6$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_6$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_6$ is H. In some embodiments related to compounds of formula (I-c), $R_6$ is H.

With respect to formula (I-b), (I-c), or (I-d), in some embodiments, $R_7$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_7$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_7$ is H. In some embodiments related to compounds of formula (I-c), $R_7$ is H.

With respect to formula (I-b), (I-c), or (I-d), in some embodiments, $R_8$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_8$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_8$ is H. In some embodiments related to compounds of formula (I-c), $R_8$ is H.

In some embodiments, $R_9$-$R_{12}$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —$CF_3$, and/or any combination of said groups, provided that at least one of $R_9$-$R_{12}$ is not hydrogen.

With respect to formula (I-e), in some embodiments, $R_9$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_9$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_9$ is H. In some embodiments, $R_9$ is $CH_3$.

With respect to formula (I-e), in some embodiments, $R_{10}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{10}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{10}$ is H.

With respect to formula (I-e), in some embodiments, $R_{11}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{11}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{11}$ is H.

With respect to formula (I-e), in some embodiments, $R_{12}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{12}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc;

optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{12}$ is H.

With respect to formula (I-f), in some embodiments, $R_{13}$-$R_{16}$ are each independently selected from hydrogen, —F, —CN, and —$CF_3$, provided that at least one of $R_{13}$-$R_{16}$ is not hydrogen.

With respect to formula (I-f), in some embodiments, $R_{13}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{13}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{13}$ is H.

With respect to formula (I-f), in some embodiments, $R_{14}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{14}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{14}$ is H. In some embodiments, $R_{14}$ is CN.

With respect to formula (I-f), in some embodiments, $R_{15}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{15}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{15}$ is H.

With respect to formula (I-f), in some embodiments, $R_{16}$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_{16}$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_{16}$ is H.

In some embodiments, $R_1$ of formula (I-a) is —F or —$CF_3$. In some embodiments, $R_1$ of formula (I-a) is —F. In some embodiments, $R_1$ of formula (I-a) is —$CF_3$.

In some embodiments, $A_2$ of formula (I-a), (I-b), (I-c), (I-d), (I-e), or (I-f), is —CN.

In some embodiments, $R_2$-$R_4$ of formula (I-a) are independently hydrogen or —F.

In some embodiments, $X_1$ of formula (I-b) is N, and $R_5$-$R_8$ of formula (I-b), (I-c), or (I-d) are hydrogen.

In some embodiments, $R_9$-$R_{12}$ of formula (I-e) are independently hydrogen or alkyl.

In some embodiments, $R_{13}$-$R_{16}$ of formula (I-f) are independently hydrogen and —CN.

In some embodiments the chromophore comprises one of the following structures as represented by formula (I-a):

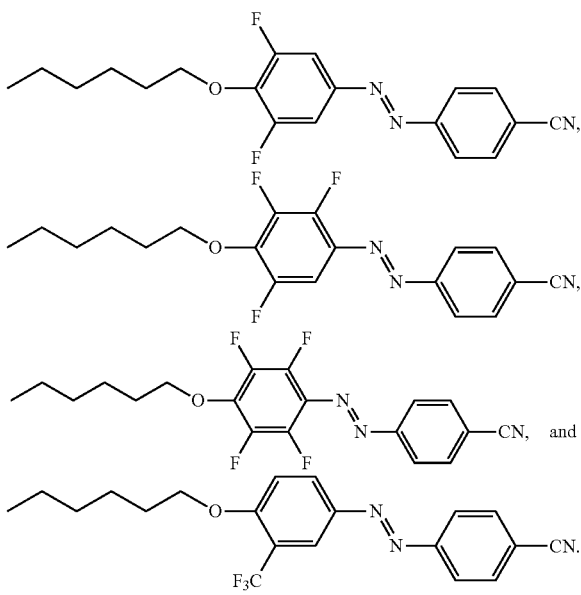

In some embodiments the chromophore comprises the following structure as represented by formula (I-b):

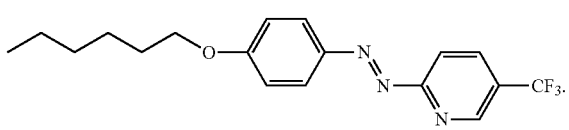

In some embodiments the chromophore comprises the following structure as represented by formula (I-c):

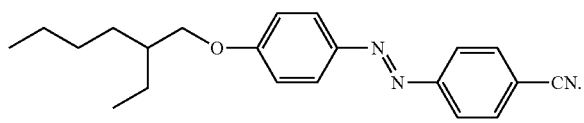 [SMILES: CCCCC(CC)COc1ccc(/N=N/c2ccc(C#N)cc2)cc1]

In some embodiments the chromophore comprises the following structure as represented by formula (I-d):

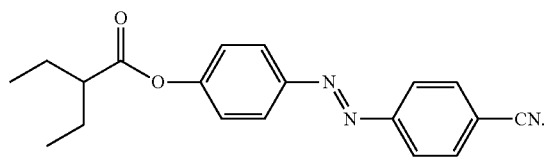 [SMILES: CCC(CC)C(=O)Oc1ccc(/N=N/c2ccc(C#N)cc2)cc1]

In some embodiments the chromophore comprises the following structure as represented by formula (I-e):

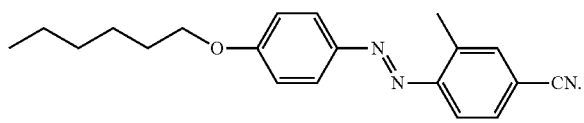 [SMILES: CCCCCCOc1ccc(/N=N/c2ccc(C#N)cc2C)cc1]

In some embodiments the chromophore comprises one of the following structures as represented by formula (I-f):

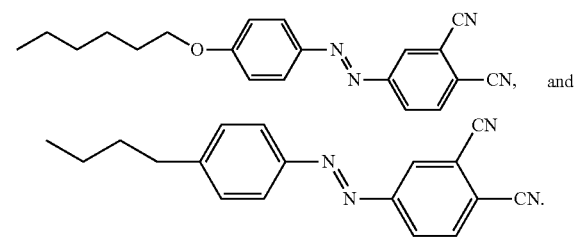

Formula (II)

In some embodiments, a chromophore is represented by formula (II):

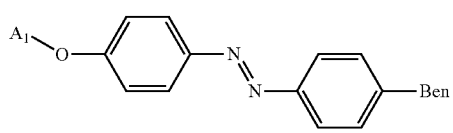

wherein Ben=

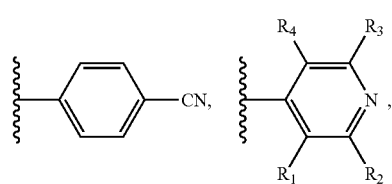

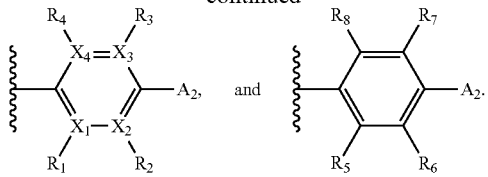

Some embodiments include a compound represented by Formula (IIa):

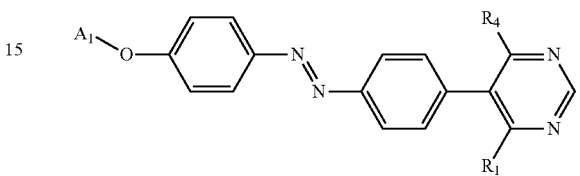

With respect to Formula (II) or (IIa), $A_1$ is selected from optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, and/or any combination of said groups.

With respect to formula (II), in some embodiments, $A_2$ is —H, —F, —CN, —CF$_3$, or —NO$_2$. In some embodiments, $A_2$ is —CN. In some embodiments, $A_2$ is —H.

With respect to formula (II), in some embodiments, $X_1$-$X_4$ are each independently selected from C or N, provided that at least one of $X_1$-$X_4$ is N.

With respect to formula (II), in some embodiments, $X_1$ is C.

With respect to formula (II), in some embodiments, $X_2$ is C. In some embodiments, $X_2$ is N.

With respect to formula (II), in some embodiments, $X_3$ is C. In some embodiments, $X_2$ is N. With respect to formula (II), in some embodiments, $X_1$ and $X_3$ are N.

With respect to formula (II), in some embodiments, $X_4$ is C.

With respect to formula (II) or (IIa), in some embodiments, $R_1$-$R_8$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —CF$_3$, and/or any combination of said groups, provided that at least one of $R_5$-$R_8$ is not hydrogen.

With respect to formula (II) or (IIa), in some embodiments, $R_1$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_1$ is H; $C_{1-12}$ alkyl, such as CC$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc; optionally substituted alkoxy such as —O—C—O—C$_3$H$_7$, —O—C$_4$H$_9$, —O—C$_5$H$_{11}$, —O—C$_6$H$_{13}$, —O—C$_7$H$_{15}$, —O—C$_8$H$_{17}$, —O—C$_9$H$_{19}$, —O—C$_{10}$H$_{21}$, etc; $C_{1-12}$ acyl, such as such as —CO—

$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_1$ is H.

With respect to formula (II), in some embodiments, $R_2$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_2$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_2$ is H. In some embodiments, $R_2$ is $CH_3$.

With respect to formula (II), in some embodiments, $R_3$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_3$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_3$ is H.

With respect to formula (II) or (IIa), in some embodiments, $R_4$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_4$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_4$ is H.

With respect to formula (II), in some embodiments, $R_5$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_5$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_5$ is H.

With respect to formula (II), in some embodiments, $R_6$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_6$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_6$ is H. In some embodiments, $R_6$ is acetyl.

With respect to formula (II), in some embodiments, $R_7$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_7$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$C_8H_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_7$ is H.

With respect to formula (II), in some embodiments, $R_8$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_8$ is H; $C_{1-12}$ alkyl, such as $CC_3H_7$, $C_4H_9$, $C_5H_{11}$, $C_6H_{13}$, $C_7H_{15}$, $C_8H_{17}$, $C_9H_{19}$, $C_{10}H_{21}$, etc; optionally substituted alkoxy such as —O—C—O—$C_3H_7$, —O—$C_4H_9$, —O—$C_5H_{11}$, —O—$C_6H_{13}$, —O—$C_7H_{15}$, —O—$CH_{17}$, —O—$C_9H_{19}$, —O—$C_{10}H_{21}$, etc; $C_{1-12}$ acyl, such as such as —CO—$C_2H_5$, —CO—$C_3H_7$, —CO—$C_4H_9$, —CO—$C_5H_{11}$, —CO—$C_6H_{13}$, —CO—$C_7H_{15}$, —CO—$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_8$ is H. n.

In some embodiments, $A_1$ of formula (II) or (IIa) is $C_{3-10}$ alkyl, such as $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or $C_{3-6}$ acyl, such as —CO—$C_2H_5$, —CO—$C_3H_7$, —CO—$C_4H_9$, —CO—$C_5H_{11}$, —CO—

$C_6H_{13}$, $-CO-C_7H_{15}$, $-CO-C_8H_{17}$, $-CO-C_9H_{19}$, $-CO$-phenyl, etc. In some embodiments, $A_1$ of formula (II) is $H_2C-CH_2-CH_2-CH_2-CH_2-CH_3-CH_2-CH_2-CH_2-CH_3$,

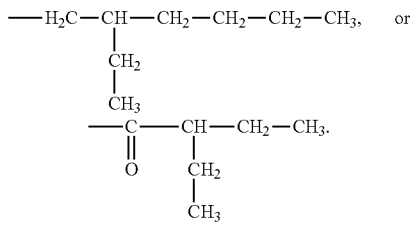

In some embodiments, $A_1$ is $H_2C-CH_2-CH_2-CH_2-CH_2-CH_3$. In some embodiments, $A_1$ is $-CH_2-CH_2-CH_2-CH_3$. In some embodiments, $A_1$ is

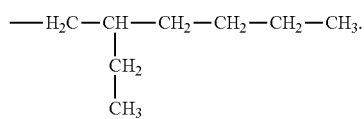

In some embodiments, $A_1$ is

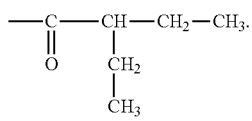

In some embodiments related to formula (IIa), $A_1$ is C1-10 alkyl, or C6-10 alkyl, such as a hexyl isomer, a heptyl isomer, an octyl isomer, a nonyl isomer, or a decyl isomer. In some embodiments, $A_1$ is:

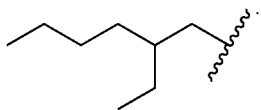 [SMILES: *CC(CC)CCCC]

In some embodiments, $A_2$ of formula (II) is hydrogen.

In some embodiments, $R_1$-$R_4$ of formula (II) are independently selected from hydrogen or alkyl.

In some embodiments, $R_5$-$R_8$ of formula (II) are independently selected from hydrogen and

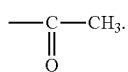

In some embodiments the chromophore comprises one of the following structures:

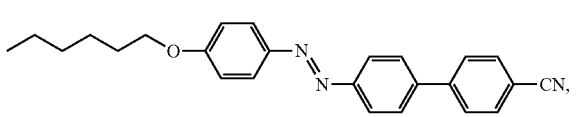

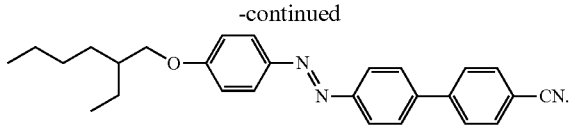

In some embodiments the chromophore comprises one of the following structures:

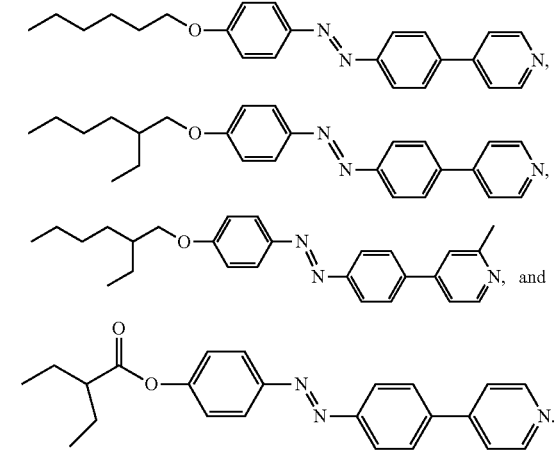

In some embodiments the chromophore comprises one of the following structures:

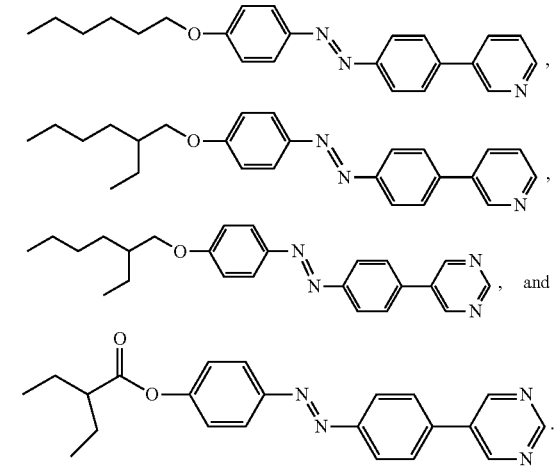

In some embodiments the chromophore comprises the following structure:

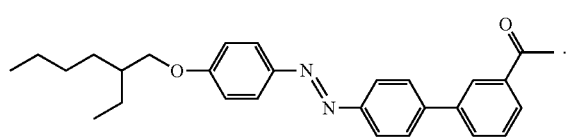 [SMILES: CCCCC(CC)COc1ccc(/N=N/c2ccc(-c3cccc(C(C)=O)c3)cc2)cc1]

Formulae (III)

Some embodiments include a chromophore represented by formulae (III):
wherein Pen=

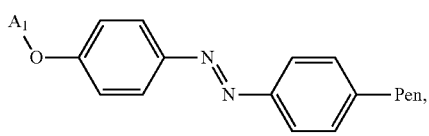

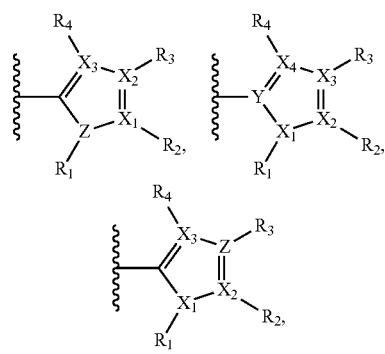

wherein $A_1$ is selected from optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, and/or any combination of said groups.

With respect to formula (III), in some embodiments $X_1$-$X_4$ are each independently selected from C and N.

In some embodiments, Z is selected from S, O, C, and N. In some embodiments, Y is selected from C and N.

With respect to formula (III), in some embodiments Pen is

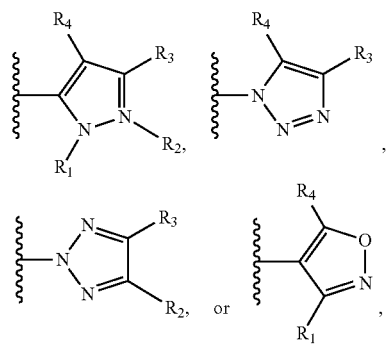

With respect to formula (III), in some embodiments $R_1$-$R_4$ are each independently selected from hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —CF$_3$, —NO$_2$, —Br, and/or any combination of said groups.

With respect to formula (III), in some embodiments $R_1$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_1$ is H; $C_{1-12}$ alkyl, such as CC$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc; optionally substituted alkoxy such as —O—C—O—C$_3$H$_7$, —O—C$_4$H$_9$, —O—C$_5$H$_{11}$, —O—C$_6$H$_{13}$, —O—C$_7$H$_{15}$, —O—C$_8$H$_{17}$, —O—C$_9$H$_{19}$, —O—C$_{10}$H$_{21}$, etc; $C_{1-12}$ acyl, such as such as —CO—C$_2$H$_5$, —CO—C$_3$H$_7$, —CO—C$_4$H$_9$, —CO—C$_5$H$_{11}$, —CO—C$_6$H$_{13}$, —CO—C$_7$H$_{15}$, —CO—C$_8$H$_{17}$, —CO—C$_9$H$_{19}$, —CO-phenyl, etc.; $C_{1-12}$ acyloxy, —OCO—C$_2$H$_5$, —OCO—C$_3$H$_7$, —OCO—C$_4$H$_9$, —OCO—C$_5$H$_{11}$, —OCO—C$_6$H$_{13}$, —OCO—C$_7$H$_{15}$, —OCO—C$_8$H$_{17}$, —OCO—C$_9$H$_{19}$, —OCO-phenyl, etc.; —F, —CN, or —CF$_3$. In some embodiments, $R_1$ is H. In some embodiments, $R_1$ is CH$_3$.

With respect to formula (III), in some embodiments $R_2$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_2$ is H; $C_{1-12}$ alkyl, such as CC$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc; optionally substituted alkoxy such as —O—C—O—C$_3$H$_7$, —O—C$_4$H$_9$, —O—C$_5$H$_{11}$, —O—C$_6$H$_{13}$, —O—C$_7$H$_{15}$, —O—C$_8$H$_{17}$, —O—C$_9$H$_{19}$, —O—C$_{10}$H$_{21}$, etc; $C_{1-12}$ acyl, such as such as —CO—C$_2$H$_5$, —CO—C$_3$H$_7$, —CO—C$_4$H$_9$, —CO—C$_5$H$_{11}$, —CO—C$_6$H$_{13}$, —CO—C$_7$H$_{15}$, —CO—C$_8$H$_{17}$, —CO—C$_9$H$_{19}$, —CO-phenyl, etc.; $C_{1-12}$ acyloxy, —OCO—C$_2$H$_5$, —OCO—C$_3$H$_7$, —OCO—C$_4$H$_9$, —OCO—C$_5$H$_{11}$, —OCO—C$_6$H$_{13}$, —OCO—C$_7$H$_{15}$, —OCO—C$_8$H$_{17}$, —OCO—C$_9$H$_{19}$, —OCO-phenyl, etc.; —F, —CN, or —CF$_3$. In some embodiments, $R_2$ is H.

With respect to formula (III), in some embodiments $R_3$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_3$ is H; $C_{1-12}$ alkyl, such as CC$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc; optionally substituted alkoxy such as —O—C—O—C$_3$H$_7$, —O—C$_4$H$_9$, —O—C$_5$H$_{11}$, —O—C$_6$H$_{13}$, —O—C$_7$H$_{15}$, —O—C$_8$H$_{17}$, —O—C$_9$H$_{19}$, —O—C$_{10}$H$_{21}$, etc; $C_{1-12}$ acyl, such as such as —CO—C$_2$H$_5$, —CO—C$_3$H$_7$, —CO—C$_4$H$_9$, —CO—C$_5$H$_{11}$, —CO—C$_6$H$_{13}$, —CO—C$_7$H$_{15}$, —CO—C$_8$H$_{17}$, —CO—C$_9$H$_{19}$, —CO-phenyl, etc.; $C_{1-12}$ acyloxy, —OCO—C$_2$H$_5$, —OCO—C$_3$H$_7$, —OCO—C$_4$H$_9$, —OCO—C$_5$H$_{11}$, —OCO—C$_6$H$_{13}$, —OCO—C$_7$H$_{15}$, —OCO—C$_8$H$_{17}$, —OCO—C$_9$H$_{19}$, —OCO-phenyl, etc.; —F, —CN, or —CF$_3$. In some embodiments, $R_3$ is H.

With respect to formula (III), in some embodiments $R_4$ is hydrogen, F, Cl, Br, I, or a substituent having a molecular weight of 15 Da or 30 Da to 50 Da, 100 Da, or 150 Da, and/or consisting of at least two chemical elements, wherein the chemical elements are C, H, N, O, S, P, F, Cl, Br, or I. In some embodiments, $R_4$ is H; $C_{1-12}$ alkyl, such as CC$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc; optionally substituted alkoxy such as —O—C—O—C$_3$H$_7$, —O—C$_4$H$_9$, —O—C$_5$H$_{11}$, —O—C$_6$H$_{13}$, —O—C$_7$H$_{15}$, —O—C$_8$H$_{17}$, —O—C$_9$H$_{19}$, —O—C$_{10}$H$_{21}$, etc; $C_{1-12}$ acyl, such as such as —CO—C$_2$H$_5$, —CO—C$_3$H$_7$, —CO—C$_4$H$_9$, —CO—C$_5$H$_{11}$, —CO—C$_6$H$_{13}$, —CO—C$_7$H$_{15}$, —CO—

$C_8H_{17}$, —CO—$C_9H_{19}$, —CO-phenyl, etc.; $C_{1-12}$ acyloxy, —OCO—$C_2H_5$, —OCO—$C_3H_7$, —OCO—$C_4H_9$, —OCO—$C_5H_{11}$, —OCO—$C_6H_{13}$, —OCO—$C_7H_{15}$, —OCO—$C_8H_{17}$, —OCO—$C_9H_{19}$, —OCO-phenyl, etc.; —F, —CN, or —$CF_3$. In some embodiments, $R_4$ is H. In some embodiments, $R_4$ is $CH_3$.

In some embodiments, $A_1$ of formula (III) is $H_2C$—$CH_2$—$CH_2$—$CH_2$—$CH_2$—$CH_3$—$CH_2$—$CH_2$—$CH_2$—$CH_3$,

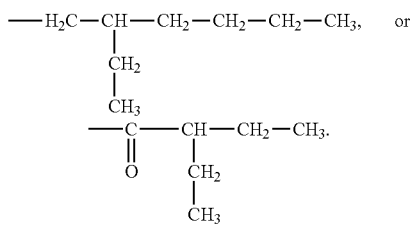

In some embodiments, $A_1$ is $H_2C$—$CH_2$—$CH_2$—$CH_2$—$CH_2$—$CH_3$. In some embodiments, $A_1$ is —$CH_2$—$CH_2$—$CH_2$—$CH_3$. In some embodiments, $A_1$ is

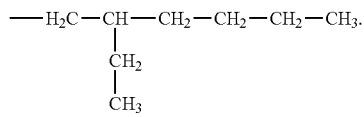

In some embodiments, $A_1$ is

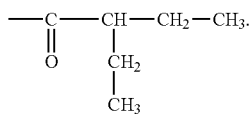

In some embodiments, Y of formula (III) is N.

In some embodiments, $R_1$-$R_4$ of formula (III) are independently selected from hydrogen or alkyl.

In some embodiments, Z of formula (III) is selected from N and O.

In some embodiments, at least one of $X_1$-$X_3$ of formula (III) is N.

In some embodiments the chromophore comprises the following structure:

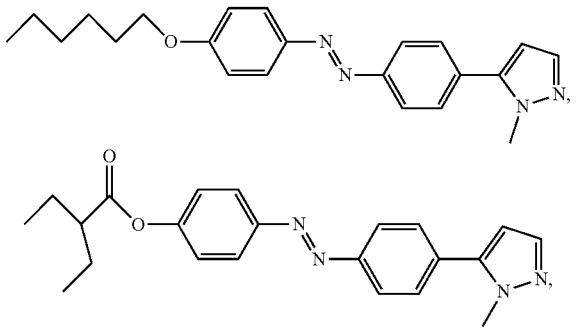

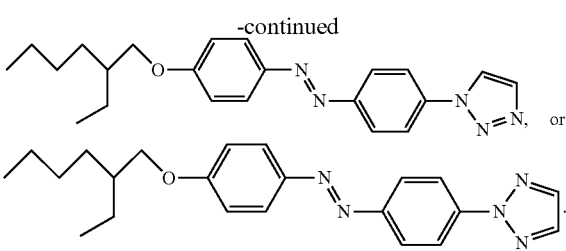

In some embodiments the chromophore comprises the following structure:

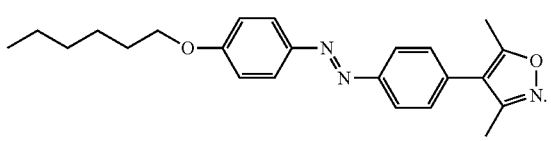 [SMILES: CCCCCCOc1ccc(/N=N/c2ccc(-c3c(C)noc3C)cc2)cc1]

Some embodiments include a photochromic composition. In some embodiments, a photochromic composition comprises a polymer matrix and a chromophore. In some embodiments, the chromophore comprises a moiety as represented by any of formulae (I-a), (I-b), (I-c), (I-d), (I-e), (I-f), (II), and (III).

Further described herein is a photochromic composition comprising a polymer matrix, and a chromophore, wherein the photochromic composition is photoresponsive upon irradiation by at least one wavelength of laser light across the visible light spectrum. Typically, the azo-benzene structure of general formulae (I-a), (I-b), (I-c), (I-d), (I-e), (I-f), (II), and (III) may be used as the chromophore.

The photochromic composition may contain more than one chromophore compound. In some embodiments of the photochromic composition, two or more chromophore compounds are mixed within the photochromic composition.

The concentration of the chromophore compound in the photochromic composition may vary widely depending on the desired photochromic properties. For instance, the desired application, whether the composition is tailored for single color holography, or multiple color holography, as well as the types and concentrations of chromophores, will have an effect on the required concentration of chromophore compound needed in the photochromic composition. In some embodiments, the chromophore compound is present in the photochromic composition in an amount in the range of about 0.01 wt % to about 60 wt %, about 0.5 wt % to about 30 wt %, about 1 wt % to about 20 wt %, about 3 wt % to about 15 wt %, about 1 wt % to about 10 wt %, about 3 wt % to about 7 wt %, about 5 wt %.

Various methods may be used to incorporate the chromophore into the polymer matrix of the photochromic composition. In some embodiments, the chromophore can be attached to the polymer backbone in one or more side chains. In some embodiments, the chromophore can be incorporated into the photochromic composition as a separate compound. In some embodiments of the photochromic composition, the chromophore may be doped into the polymer matrix such that the polymer and the chromophore are not chemically bonded. In some embodiments of the photochromic composition, one or more of the chromophores may be covalently bonded to the polymer matrix.

Various known methods may be used to covalently bond the chromophore into to the polymer matrix. In some embodiments, free radical polymerization is used to covalently bond the polymer matrix and the chromophore together.

In some embodiments, the photochromic composition further comprises additional components to induce polymerization. Typical additives that are used in polymerization process include initiators and crosslinking agents. In some embodiments, the photochromic composition further comprises an initiator. In some embodiments, the photochromic composition further comprises a cross-linking agent. In some embodiments, the photochromic composition further comprises any combination of initiator and cross-linking agent.

Liquid crystals have also been used to induce or improve photochromic properties in a material. Liquid crystals include matter in a state that has properties between those of conventional liquid and those of solid crystal. In some cases, adding liquid crystals to the photochromic composition may improve the photoresponse in the composition. In some embodiments, the photochromic composition further comprises a liquid crystal. In some embodiments, the liquid crystals comprise a polymer material. In some embodiments of the photochromic composition, the liquid crystal comprises an aromatic polyester polymer. In some embodiments, the liquid crystal is present in the photochromic composition in an amount of about 0.01 wt % to about 30 wt %. In some embodiments, the liquid crystal is present in the photochromic composition in an amount of about 1 wt % to about 15 wt %. In some embodiments, the liquid crystal is doped into the photochromic composition such that it is not bonded to the polymer matrix or the chromophore. In some embodiments, one or more of each of the chromophore compound and the liquid crystal are covalently bonded to the polymer matrix. In some embodiments, free radical polymerization is used to covalently bond the chromophore compound and the liquid crystal to the polymer matrix.

In some embodiments, the chromophore can be attached to the polymer backbone in one or more side chains. In some embodiments, the chromophore can be incorporated into the photochromic composition as a separate compound.

Various polymers can be used as the polymer matrix of the photochromic composition. In some embodiments, the polymer matrix comprises a repeating unit that includes a moiety represented by the following formula (IV):

(IV)

wherein $Rb_1$ and $Rb_2$ are independently selected from the group consisting of hydrogen, $C_1$-$C_{10}$ alkyl, $C_1$-$C_{10}$ alkenyl, and $C_6$-$C_{10}$ aryl. In some embodiments, the polymer matrix is formed from a substance selected from the group consisting of polyethylene terephthalate, polyacrylate, polymethacrylate, polyvinyl carbazole, polymethyl methacrylate, polyvinyl butyral, ethylene vinyl acetate, ethylene tetrafluoroethylene, polyimide, amorphous polycarbonate, polystyrene, siloxane sol-gel, polyurethane, and/or any combination thereof.

In some embodiments, a recurring unit of formulae (IV) and any other polymer monomer material may be incorporated to form a polymer matrix of a photochromic composition. In some embodiments, for example, the polymer can be a homopolymer of a desired recurring unit. In some embodiments, for example, two or more recurring units comprising different moieties may be included to form a polymer matrix of a photochromic composition. The polymer matrix and chromophore formed by inclusion of these moieties has photochromic properties. Those skilled in the art will appreciate that the use of the term "polymer" herein includes copolymers.

The desired polymer substance can also be attached to a polymer backbone that is the same or different. Many polymer backbones, including but not limited to, polyurethane, epoxy polymers, polystyrene, polyether, polyester, polyamide, polyimide, polysiloxane, polyacrylate, polyvinyl carbazole, and polymethacrylate, with the appropriate side chains attached, can be used to make the polymers of the photochromic compositions. Some embodiments contain backbone units based on acrylates or styrene, and some of preferred backbone units are formed from acrylate-based monomers, and some are formed from methacrylate monomers. It is believed that the first polymeric materials to include photoconductive functionality in the polymer itself were the polyvinyl carbazole materials developed at the University of Arizona. However, these polyvinyl carbazole polymers tend to become viscous when subjected to the heat-processing methods typically used to form the polymer into films or other shapes for use in photochromic devices.

The (meth)acrylate-based and acrylate-based polymers used in embodiments described herein exhibit good thermal and mechanical properties. Such polymers provide improved durability and workability during processing by injection-molding or extrusion, especially when the polymers are prepared by radical polymerization. Some embodiments provide a composition comprising a photochromic composition that is photoresponsive upon irradiation by one or more of a red laser, a green laser, and a blue laser. Some embodiments provide a composition comprising a photochromic composition that is photoresponsive upon irradiation by two or more of a red laser, a green laser, and a blue laser. Some embodiments provide a composition comprising a photochromic composition that is photoresponsive upon irradiation by three lasers, one of each of a red laser, a green laser, and a blue laser.

In some embodiments, a polymer comprising a chromophore of any of formulae (I-a), (I-b), (I-c), (I-d), (I-e), (I-f), (II), (IIa), and (III) and a repeating unit of formulae (IV) can be formed by copolymerization of the corresponding monomers to provide a photochromic composition. In some embodiments, monomers comprising a phenyl amine derivative can be copolymerized with the chromophore of any of formulae (I-a), (I-b), (I-c), (I-d), (I-e), (I-f), (II), and (III) to form the photochromic composition as well. Non-limiting examples of such monomers are carbazolylpropyl (meth)acrylate monomer; 4-(N,N-diphenylamino)-phenylpropyl (meth)acrylate; N-[(meth)acroyloxypropylphenyl]-N, N',N'-triphenyl-(1,1'-biphenyl)-4,4'-diamine; N-[(meth) acroyloxypropylphenyl]-N'-phenyl-N, N'-di(4-methylphenyl)-(1,1'-biphenyl)-4,4'-diamine; and N-[(meth) acroyloxypropylphenyl]-N'-phenyl-N, N'-di(4-buthoxyphenyl)-(1,1'-biphenyl)-4,4'-diamine. These monomers can be used singly or in combination to provide homopolymers or copolymers.

The photochromic composition described herein may be prepared in various ways, e.g., by polymerization of the corresponding monomers or precursors thereof. Polymerization may be carried out by methods known to a skilled artisan, as informed by the guidance provided herein. In some embodiments, radical polymerization using an azo-type initiator, such as AIBN (azoisobutyl nitrile), may be carried out. Further, by following the techniques described herein, it is possible in preferred embodiments to prepare such materials with exceptionally good properties, such as photoinduced birefringence, response time, and diffraction efficiency. In an embodiment of a radical polymerization method, the polymerization catalysis is generally used in an amount of from 0.01 to 5 mole % or from 0.1 to 1 mole % per mole of the total polymerizable monomers.

In some embodiments, the photochromic composition comprising the polymer matrix and the chromophore can be prepared in a conventional manner by free-radical copolymerization with the monomers in suitable solvents, such as, for example, aromatic hydrocarbons, such as toluene or xylene, halogenated aromatic hydrocarbons, such as chlorobenzene, ethers, such as tetrahydrofuran and dioxane, ketones, such as acetone and cyclohexanone and/or dimethylformamide, in the presence of polymerization initiators which supply free radicals, such as, for example, azobisisobutyronitrile or benzoyl peroxide, at elevated temperatures, in general at from 30° C. to 130° C., preferably at from 40° to 70° C., if possible in the absence of water and air. They can be isolated by precipitation using suitable agents, for example methanol. The products can be purified by reprecipitation, for example using chloroform/methanol.

In some embodiments, the photochromic compositions can be formed into self-supporting films. However, in some preferred embodiments, the photochromic compositions can be formed into films that are applied to support materials. This can be carried out by various techniques known per se, the method being selected depending on whether a thick or thin coating is desired. Thin coatings can be produced, for example, by spin coating or knife coating from solutions or melts, while thicker coatings can be produced from prefabricated cells, by melt pressing or by extrusion.

Additional additives may be used during polymerization to form the polymer matrix. In some embodiments additional additives such as a cross linking agent, an antiaging agent, a bulking agent, an ultraviolet ray absorbent, an antioxidant, a chain transfer agent, a plasticizer, a softener, a surface-active agent, can be used independently or in any combination thereof, to form the photochromic composition.

In some embodiments, the crosslinking agent used may be an isocyanate compound, an epoxy compound, a melamine-based resin, an aziridine derivative, a metal chelate compound, or the like. Particularly preferable is an isocyanate or epoxy compound since the compound gives an appropriate cohesive strength. It is particularly preferable that at the time of the production of a polymer, the polymer is copolymerized with a hydroxyl containing monomer such as 2-hydroxyethyl acrylate so as to introduce the hydroxyl group into the polymer and then a polyisocyanate compound is used as a crosslinking agent for this polymer. These compounds may be used alone, or two or more of them may be used by mixing.

Examples of the isocyanate compound include low aliphatic polyisocyanates such as butylene diisocyanate and hexamethylene diisocyanate; alicyclic isocyanates such as cyclopentylene diisocyanate, cyclohexylene diisocyanate, and isophrone diisocyanate; aromatic isocyanates such as 2,4-tolylene diisocyanate, 4,4'-diphenylmethane diisocyanate, and xylylene diisocyanate; isocyanate adducts such as a trimethylolpropane/tolylene diisocyanate trimer adduct, a trimethylolpropane/hexamethylene diisocyanate trimer adduct, and an isocyanurate product of hexamethylene diisocyanate; and diisocyanate adducts to polyol. These compounds may be used alone, or two or more of them may be used by mixing.

Examples of the epoxy include N,N,N',N'-tetraglycidyl-m-xylenediamine, and 1,3-bis(N,N-diglycidylaminomethyl) cyclohexane. These compounds may be used alone, or two or more of them may be used by mixing.

An example of the melamine-based resin is hexamethylolmelamine.

Examples of the aziridine derivative include commercially available products manufactured by Sogo Pharmaceutical Co., Ltd. (trade names: HDU, TAZM and TAZO). These compounds may be used alone, or two or more of them may be used by mixing.

Examples of the metal chelate compound include compounds wherein the metal component thereof is aluminum, iron, tin, titanium, or nickel, and the chelate component thereof is acetylene, methyl acetoacetate, or ethyl lactate. These compounds may be used alone, or two or more of them may be used by mixing.

The content of the crosslinking agent used is usually from about 0.01 to 5 parts by weight for 100 parts by weight of the base polymer such as (meth)acrylate-based polymer.

In some embodiments, the photochromic composition is formed into a thin film. The method for forming the photochromic composition into a thin film may be appropriately selected from known methods used to produce thin films. Specific examples thereof include roll coating, kiss roll coating, gravure coating, reverse coating, roll brush coating, spray coating, dip roll coating, bar coating, knife coating, and air knife coating.

In some embodiments the photochromic composition may be coated onto an optically transparent substrate. The optically transparent substrate may be plastic or glass.

In some embodiments, radical polymerization can be carried out under inert gas (e.g., nitrogen, argon, or helium) and/or in the presence of a solvent (e.g., ethyl acetate, tetrahydrofuran, butyl acetate, toluene or xylene). Polymerization may be carried out under a pressure from 1 to 50 Kgf/cm$^2$ or from 1 to 5 Kgf/cm$^2$. In some embodiments, the concentration of total polymerizable monomer in a solvent may be about 0.99% to about 50% by weight based on the total weight of the composition, preferably about 2% to about 9.1% by weight based on the total weight of the composition. The polymerization may be carried out at a temperature of about 50° C. to about 100° C., and may be allowed to continue for about 1 to about 100 hours, depending on the desired final molecular weight, polymerization temperature, and taking into account the polymerization rate.

In some embodiments, the photochromic composition responds favorably upon irradiation with light in at least one of a red wavelength, a green wavelength, and a blue wavelength. In some embodiments, the photochromic composition responds favorably upon irradiation with light in more than one of a red wavelength, a green wavelength, and a blue wavelength. In some embodiments, the photochromic compositions have chemical and optical properties that are compatible with the transmittance of all three wavelengths of color light. As described herein, a laser having a blue wavelength is as a laser having a wavelength in the range of about 400 nm to about 490 nm. In some embodiments, the blue laser has a wavelength of about 488 nm. In some embodiments, the blue laser has a wavelength of about 457 nm. As described herein, a laser having a green wavelength is as a laser having a wavelength in the range of about 490 nm to about 600 nm. In some embodiments, the green laser has a wavelength of about 532 nm. As described herein, a laser having a red wavelength is as a laser having a wavelength in the range of about 600 nm to about 700 nm. In some embodiments, the red laser has a wavelength of about 633 nm.

In some embodiments, the photochromic composition comprises a chromophore compound as represented by any of the general formulae (I-a), (I-b), (I-c), (I-d), (I-e), (I-f), (II), (IIa), and (III), that, in combination with the other components of the composition, configures the composition to be sensitive to two or more wavelengths of visible light lasers, e.g., blue, green, and red lasers. In some embodiments, the photochromic composition can be configured to be sensitive to two or more wavelengths of laser by selection of the type and amount of polymer and chromophore and to render the composition sensitive to the selected laser wavelengths. In some embodiments, the photochromic composition may further comprise a type and amount of sensitizer selected to render the composition sensitive to one or more visible light wavelengths.

As used herein, a composition that absorbs light at each of the blue, green, and red laser wavelength includes a composition that can absorb a detectable amount of incident light, such as at least about 10% of incident working wavelength light. The incident working wavelength is the wavelength of the laser light that is used to irradiate the photochromic composition. In some embodiments, the composition can absorb more than 10% of incident working wavelength light. In some embodiments, the composition absorbs at least about 20% of incident working wavelength light. In some embodiments, the composition absorbs at least about 30% of incident working wavelength light. In some embodiments, the composition absorbs at least about 40% of incident working wavelength light. In some embodiments, the composition absorbs at least about 50% of incident working wavelength light. In some embodiments, the composition absorbs at least about 60% of incident working wavelength light.

In some embodiments the photochromic composition is configured to be photoresponsive upon irradiation by at least a first laser having a first wavelength in the visible light spectrum, and wherein the first laser is selected from a blue laser, a green laser, and a red laser. In some embodiments the photochromic composition is configured to be photoresponsive upon irradiation by at least a first laser having a first wavelength in the visible light spectrum and a second laser having a second wavelength in the visible light spectrum, wherein the first wavelength is different from the second wavelength and wherein the first and second lasers are selected from a blue laser, a green laser, and a red laser. In some embodiments the photochromic composition is photoresponsive upon irradiation with a third laser having a third wavelength in the visible light spectrum, such that the third laser has a wavelength that is different from that of the first laser and the second laser, wherein the third laser is selected from a blue laser, a green laser, and a red laser. In some embodiments of the composition, the blue laser has a wavelength of about 488 nm, the green laser has a wavelength of about 532 nm, and the red laser has a wavelength of about 633 nm. In some embodiments of the composition, the blue laser has a wavelength of about 457 nm, the green laser has a wavelength of about 532 nm, and the red laser has a wavelength of about 633 nm.

In some embodiments, the molecular weight and the glass transition temperature, Tg, of the copolymer are selected to provide desirable physical properties. In some embodiments, it is valuable and desirable, although not essential, that the polymer is capable of being formed into films, coatings and shaped bodies of various kinds by standard polymer processing techniques (e.g., solvent coating, injection molding or extrusion).

In some embodiments, the polymer has a weight average molecular weight, Mw, in the range of from about 3,000 to about 500,000, preferably from about 5,000 to about 100,000. The term "weight average molecular weight" as used herein means the value determined by the GPC (gel permeation chromatography) method using polystyrene standards, as is well known in the art.

In some embodiments, the photochromic composition both has the ability to absorb light at different wavelengths and also transmit light at different wavelengths. In order for the photochromic device to be responsive to any given laser wavelength, the photochromic composition should have absorption, as well as transmission at the wavelength of the measurement. The absorption of the incident light is useful to initialize the response of the device. The transmission is needed for future reading of the grating at the wavelength of interest, including from about 400 nm to about 700 nm. Preferably, the transmission of the sample is from about 20% to about 90%. In some embodiments, the transmission is from about 40% to about 80%. In some embodiments, the transmission is from about 40% to about 60%. The photochromic device can be irradiated with blue, green, or red laser and the transmitted light intensity is measured with and without the photochromic device in place. In some embodiments, the composition has a transmittance of higher than about 20% at a thickness of 100 m when irradiated by one or more of a blue laser, a green laser, and a red laser. In some embodiments, the composition has a transmittance of higher than about 30% at a thickness of 100 m when irradiated by one or more of a blue laser, a green laser, and a red laser. In some embodiments, the composition has a transmittance of higher than about 40% at a thickness of 100 m when irradiated by one or more of a blue laser, a green laser, and a red laser. In some embodiments, the composition has a transmittance of higher than about 50% at a thickness of 100 m when irradiated by one or more of a blue laser, a green laser, and a red laser. In some embodiments, the composition has a transmittance of higher than about 20% at a thickness of 100 m when irradiated by two or more of a blue laser, a green laser, and a red laser. In some embodiments, the composition has a transmittance of higher than about 30% at a thickness of 100 m when irradiated by two or more of a blue laser, a green laser, and a red laser. In some embodiments, the composition has a transmittance of higher than about 40% at a thickness of 100 m when irradiated by two or more of a blue laser, a green laser, and a red laser. In some embodiments, the composition has a transmittance of higher than about 50% at a thickness of 100 m when irradiated by two or more of a blue laser, a green laser, and a red laser.

Other embodiments include a method of modulating light, comprising providing a photochromic composition (e.g., a photochromic composition as described herein) that comprises a polymer matrix and a chromophore as represented by any of general formulae (I-a), (I-b), (I-c), (I-d), (I-e), (I-f), (II), (IIa), and (III) wherein the polymer matrix comprises a moiety of the formula (IV), or a moiety of polyethylene terephthalate, polyacrylate, polymethacrylate, polymethyl methacrylate, polyvinyl butyral, ethylene vinyl acetate, ethylene tetrafluoroethylene, polyimide, amorphous polycarbonate, polystyrene, siloxane sol-gel, polyurethane, and combinations thereof, and irradiating the photochromic composition with one or more of a blue laser, a green laser and a red laser to thereby modulate a photochromic property of the composition. In some embodiments, modulating a photochromic property comprises activating the photochromic composition. In some embodiments, the photochromic composition is irradiated with a blue laser, a green laser, and a red laser.

Another one of many advantages of some of the photochromic composition disclosed herein is the high diffraction efficiency, η. Diffraction efficiency is defined as the ratio of the intensity of a diffracted beam to the intensity of an incident probe beam, and is determined by measuring the intensities of the respective beams. Various samples of embodiments described herein provide a diffraction efficiency of at least about 20% upon irradiation by one or more of a blue laser, a green laser and a red laser. In some embodiments the photochromic compositions described herein provide a diffraction efficiency of at least about 20% upon irradiation by one or more of a blue laser, a green laser and a red laser. In some embodiments, the photochromic compositions provide a diffraction efficiency of at least about 25% upon irradiation by one or more of a blue laser, a green laser and a red laser. In some embodiments, the photorefractive compositions provide a diffraction efficiency of at least about 30% upon irradiation by one or more of a blue laser, a green laser and a red laser. In some embodiments, the photorefractive compositions provide a diffraction efficiency of at least about 40% upon irradiation by one or more of a blue laser, a green laser and a red laser.

For a photochromic device, usually the thickness of a photochromic layer is from about 10 □m to about 1000 □m. Preferably, the thickness range is from about 30 □m to about 500 □m. If the sample thickness is less than 10 □m, the diffracted signal may not be in the desired Bragg Refraction region, but Raman-Nathan Region which may not show proper grating behavior. Also, the transmittance for all color laser beams in overly thick photochromic layers can be reduced significantly and result in no grating signals.

Additional embodiments include an optical device comprising a photochromic composition as described herein. In some embodiments, the optical device is responsive to irradiation by at least one of a blue laser, a green laser, and a red laser. In some embodiments, the optical device is responsive to irradiation by at least two of a blue laser, a green laser, and a red laser. In some embodiments, the optical device is responsive to irradiation by at least one of a blue laser, a green laser, and a red laser. In some embodiments, the composition is photochromic upon irradiation by continuous wave (CW) lasers.

FIG. 1 is a schematic depiction illustrating a hologram recording system with a photochromic composition. Information may be recorded into the hologram medium, and the recorded information may be read out simultaneously. A laser source 11 may be used to write information onto a recording medium 12. The recording medium 12 comprises a photochromic composition as described herein and is positioned over a support material 13.

Laser beam irradiation 11 from the single light source split on two beams-object 14 and reference 16. Both beams, object 14 and reference 16 intersect into recording medium 12 causing an interference pattern, which generates formation of gratings in the Bragg regime. Object beam 14 and reference beam 16 can be applied from various sides of the device other than those illustrated in FIG. 1. For example, instead of projecting from the same side of the recording medium 12 (transmission type of hologram), object beam 14 and reference beam 16 could project from opposite sides of the recording medium 12 (reflection type of hologram). Wide variety of angles between the object beam 14 and reference beam 16 can also be used. Multiple recordings (multiplicity) are possible in the photochromic composition of the recording medium 12 by changing the angle between the incident beams.

An image display device 19 is set up parallel to the X-Y plane of the recording medium 12. Various types of image display devices may be employed. Some non-limiting examples of image display devices include a liquid crystal device, a Pockels Readout Optical Modulator, a Multichannel Spatial Modulator, a CCD liquid crystal device, an AO or EO modulation device, or an opto-magnetic device. On the other side of the recording medium 12, a read-out device 18 is also set up parallel to the X-Y plane of the recording medium 12. Suitable read-out devices include any kind of opto-electro converting devices, such as CCD, photo diode, photoreceptor, or photo multiplier tube.

In order to read out recorded information, the object beam 14 is shut out and only the reference beam 16, which is used for recording, is irradiated. A reconstructed image may be restored, and the reading device 18 is installed in the same direction as the transmitted portion 15 of the object beam and away from the reference beam 16. However, the position of the reading device 18 is not restricted to the positioning shown in FIG. 1. Recorded information in the photochromic composition can be erased completely by whole surface light irradiation with single writing beam with circular polarization, or applying thermal treatment or thermal treatment and light irradiation together.

The method can build the diffraction grating on the recording medium. This hologram device can be used not only for optical memory devices but also other applications, such as a hologram interferometer, a 3D holographic display, coherent image amplification applications, novelty filtering, self-phase conjugation, beam fanning limiter, signal processing, and image correlation, etc.

Holographic image performance may be measured by the speed with which the image is written to the device, known as the response time, the maximum difference in the refractive index within the material, known as the photoinduced birefringence (Dn), the diffraction efficiency, and the brightness of the image. Surprisingly, the inventors discovered that by using the novel azo-benzene chromophores disclosed herein, the photochromic device shows higher birefringence with bright holographic images, than devices that comprise the prior art azo-benzene chromophores. Therefore, in some embodiments, the improvement in birefringence of photochromic devices comprising the novel azo-benzene type chromophore disclosed herein, is about 50% or more compared to photochromic devices comprising prior art azo-benzene chromophores. In some embodiments, the improvement in birefringence of photochromic devices comprising the novel azo-benzene type chromophore disclosed herein, is about 100% or more compared to photochromic devices comprising prior art azo-benzene chromophores. In some embodiments, the improvement in birefringence of photochromic devices comprising the novel azo-benzene type chromophore disclosed herein, is about 120% or more compared to photochromic devices comprising prior art azo-benzene chromophores. In some embodiments, a photochromic composition may have a birefringence of about $0.5 \times 10^{-3}$ to about $2 \times 10^{-3}$, about $0.7 \times 10^{-3}$ to about $1.7 \times 10^{-3}$, about $1 \times 10^{-3}$ to about $1.7 \times 10^{-3}$, or about $1.2 \times 0^{-3}$ to about $1.7 \times 10^{-3}$.

The image brightness may be measured using a luminance meter, which measures the absolute value of the Image brightness in $cd/m^2$, as is described below. In some embodiments, when using the photochromic compositions, as disclosed herein, which comprise a novel azo-benzene type chromophore compound, the Image Brightness of the image is about 100 cd/m$^2$ or higher. In some embodiments, when using the photochromic compositions, as disclosed herein, the Image Brightness of the image is about 150 cd/m$^2$ or higher. In some embodiments, when using the photochromic compositions, as disclosed herein, the Image Brightness of the image is about 200 cd/m$^2$ or higher. In some embodiments, when using the photochromic compositions, as disclosed herein, the Image Brightness of the image is about 250 cd/m$^2$ or higher.

The embodiments are now further described by the following examples, which are intended to be illustrative of the invention, but are not intended to limit the scope or underlying principles in any way.

Syntheses and Production Methods

The embodiments will be explained with respect to preferred embodiments which are not intended to limit any particular embodiment. In the present disclosure, the listed substituent groups include both further substituted and unsubstituted groups unless specified otherwise.

Synthesis of Chromophore 1

The novel azo-benzene chromophore (Chromophore 1) was synthesized according to the following synthesis scheme:

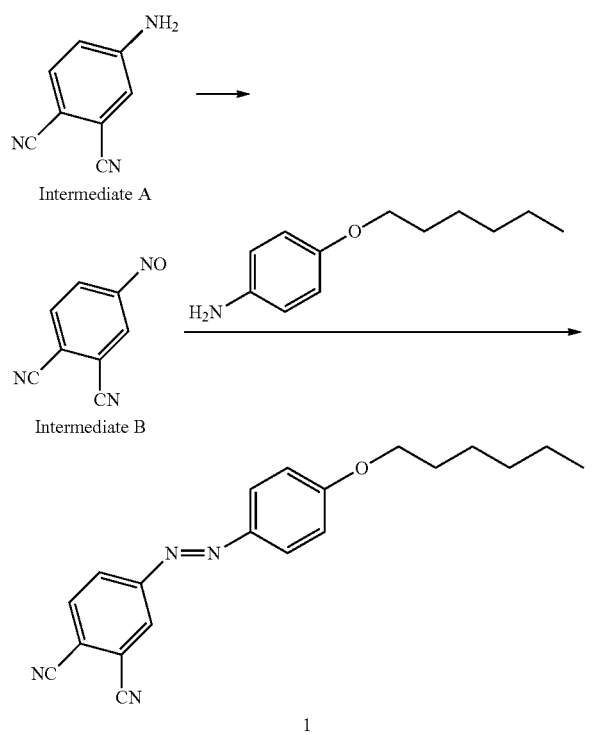

4-Aminiphthalonitrile (Intermediate A) (5.7 g, 40 mmol) was dissolved in 200 mL of dichloromethane and ozone (48.0 g, 2 eq) in 400 mL of water was added while vigorously stirred, and left stirred at room temperature for five hours. The reaction was monitored by TLC. Formation of solid pellets was observed and those proved to be actual product. Work-up by washing dichloromethane layer with 1 M HCl, followed by NaHCO$_3$ solution, and water. Dried over anhydrous MgSO$_4$ and rotavaped to give Intermediate B as greenish thick oil which solidified with time (6.1 g, %) which was used for the next step without purification.

Intermediate B (800 mg, 5 mmol) and 4-hexyloxyaniline (980 mg, 1 eq) was reacted in acetic acid (30 mL) overnight (16 hours) at room temperature. After water was added, the solid which was formed was separated by filtration, washed, and dried in a vacuum oven to give 1.7 g of crude brownish product which was purified by column chromatography (silica gel, dichloromethane) to give pure Chromophore 1 as orange color solid (1.25 g, yield 75%). $^1$H NMR (400 MHz, CDCl$_3$): □ 8.25 (d, J=1.8 Hz, 1H), 8.16 (dd, J=8.4 and 1.8 Hz, 1H), 7.95 (d, J=9.2 Hz, 2H), 7.92 (d, J=8.4 Hz, 1H), 7.02 (d, J=8.8 Hz), 4.07 (t, J=6.4 Hz, 2H), 1.83 (m, 2H), 1.48 (m, 2H), 1.35 (m, 4H), 0.91 (t, 6.9 Hz, 3H).

Synthesis of Chromophore 2

The novel azo-benzene chromophore (Chromophore 2) was synthesized according to the following synthesis scheme:

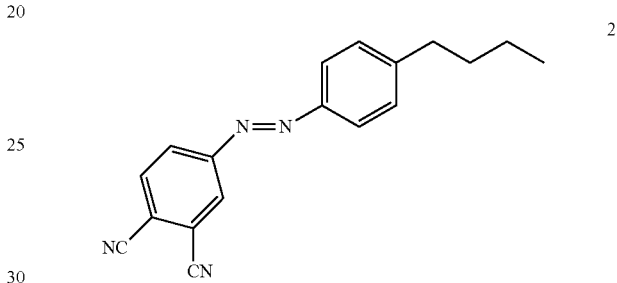

Chromophore 2 was prepared using the same procedure on the same scale as for Chromophore 1 but 4-butylaniline was used instead. Purification by column gave product as dark orange solid (550 mg, yield 38%). $^1$H NMR (400 MHz, CDCl$_3$): □□ 8.29 (d, J=1.8 Hz, 1H), 8.20 (dd, J=8.4 and 1.8 Hz, 1H), 7.95 (d, J=8.4 Hz, 1H), 7.89 (d, J=8.0 Hz, 2H), 7.37 (d, J=8.4 Hz), 2.71 (t, J=7.7 Hz, 2H), 1.65 (m, 2H), 1.38 (m, 2H), 0.95 (t, J=7.4 Hz, 3H).

Synthesis of Intermediate E

The azo-benzene structure (Intermediate E) was synthesized according to the following synthesis scheme:

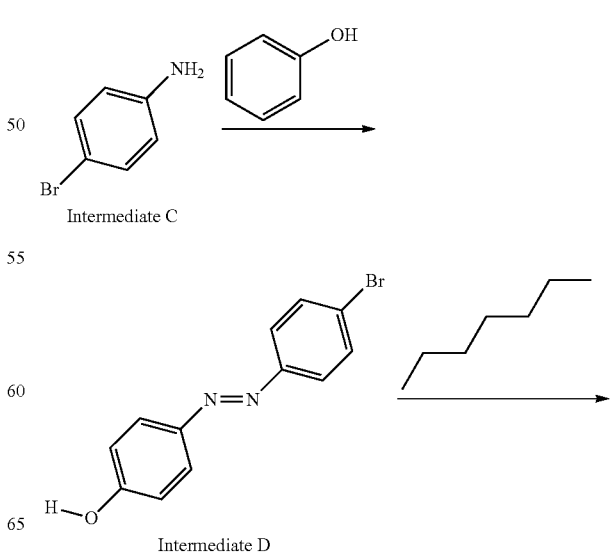

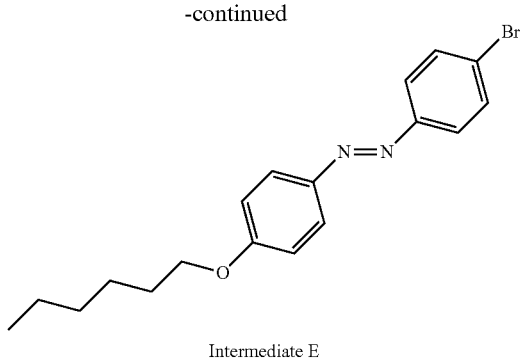

Intermediate E

A solution of 4-bromoaniline (17.7 g, 100 mmol) and 3M HCl (200 mL) was combined to dissolve the solid. The mixture was cooled to 0° C. in an ice bath with stirring. Freshly prepared 1 M sodium nitrite solution (6.9 g, 100 mmol) was then added slowly with stirring. The rate of addition was adjusted so that the temperature of the solutions remains below 10° C. The solution was kept in an ice bath and used immediately in the next step.

Then, a solution of phenols (9.41 g, 100 mmol) in 2 M NaOH (300 mL) was prepared and cooled in an ice bath. The diazonium salt from last step was then added slowly with stirring to the phenol solution. The reaction mixture was then left standing in the ice bath for 0.5 hrs. The pH of the solution was adjusted with dilute NaOH solutions (0.1 M) in order to neutralize. The precipitate was centrifuged to get the solid portion. Ethyl acetate was used to dissolve the solid and dry over concentrated $Na_2SO_4$, to obtain Intermediate D, a brown color solid (17 g, yield 62%). $^1$H-NMR (CDCl3): 7.87 (2H, d), 7.75 (2H, d), 7.62 (2H, d), 6.94 (2H, d), 5.40 (H, s). LC-MS: M+277.

Then all reagents were combined and heated to 60° C. overnight. TLC showed the completion of the reaction, which was then stopped, and dried and concentrated, and further purified by two times recrystallization to obtain Intermediate E, 4 g of orange color solid with the yield of 62%. $^1$H-NMR (CDCl3): δ 7.90 (2H, d), 7.76 (2H, d), 7.62 (2H, d), 7.00 (2H, d), 4.03 (2H, t), 1.82-1.24 (8H, m), 0.91 (3H, m).

Synthesis of Chromophore 3

The novel azo-benzene chromophore (Chromophore 3) was synthesized according to the following synthesis scheme:

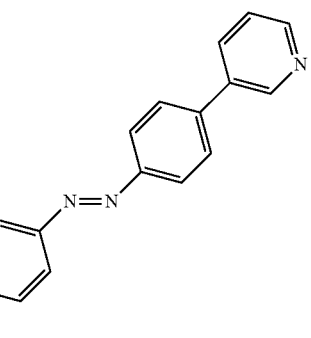

A mixture of Intermediate E, ((E)-1-(4-bromophenyl)-2-(4-(hexyloxy)phenyl)diazene), (2.77 mmol), 3-pyridinyl boronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 5 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.71 g (71%) of Chromophore 3, (E-3-(4-((4-(hexyloxy)phenyl)diazenyl)phenyl)pyridine). $^1$H-NMR (CDCl3): δ 8.91 (H, d), 8.62 (H, m), 7.94 (5H, m), 7.73 (2H, d), 7.40 (H, m), 7.02 (2H, d), 4.04 (2H, t), 1.82-1.24 (8H, m), 0.93 (3H, m). LC-MS: MH+ 360. UV-Vis in ethyl acetate 360 nm.

Synthesis of Chromophore 4

The novel azo-benzene chromophore (Chromophore 4) was synthesized according to the following synthesis scheme:

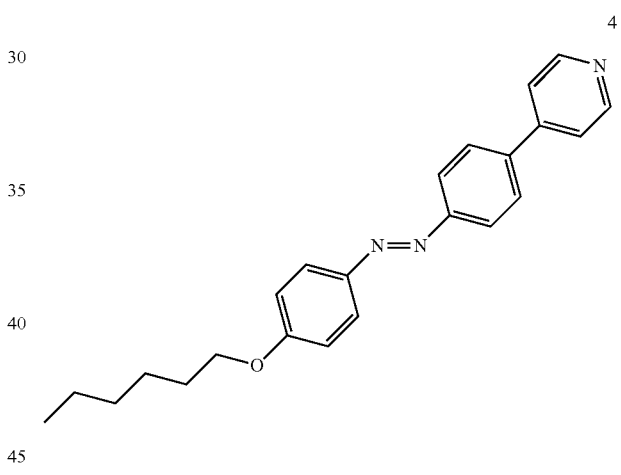

A mixture of Intermediate E ((E)-1-(4-bromophenyl)-2-(4-(hexyloxy)phenyl)diazene) (2.77 mmol), 4-pyridinyl boronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 15 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.57 g (57%) of Chromophore 4 ((E)-4-(4-((4-(hexyloxy)phenyl)diazenyl)phenyl)pyridine). $^1$H-NMR (CDCl3): δ 8.69 (2H, d), 7.99 (2H, d), 7.94 (2H, d), 7.78 (2H, d), 7.57 (2H, d), 7.02 (2H, d), 4.04 (2H, t), 1.82-1.24 (8H, m), 0.93 (3H, m). LC-MS: MH+ 360. UV-Vis in ethyl acetate 361 nm.

Synthesis of Chromophore 5

The novel azo-benzene chromophore (Chromophore 5) was synthesized according to the following synthesis scheme:

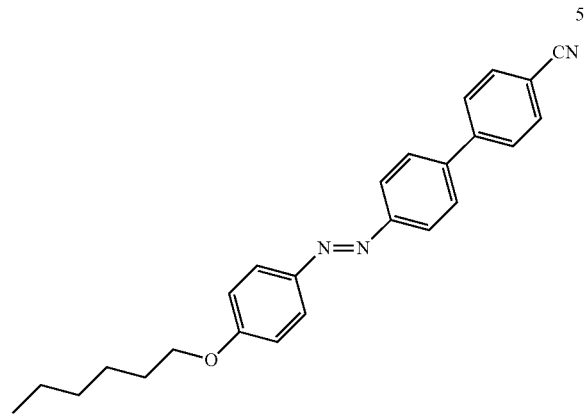 [SMILES: CCCCCCOc1ccc(/N=N/c2ccc(-c3ccc(C#N)cc3)cc2)cc1]

A mixture of Intermediate E, ((E)-1-(4-bromophenyl)-2-(4-(hexyloxy)phenyl)diazene), (2.77 mmol), 4-cyanophenylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give orange solid of Chromophore 5 [((E)-4'-((4-(hexyloxy)phenyl)diazenyl)-[1,1'-biphenyl]-4-carbonitrile]. It was further purified by recrystallization more than 3 times. $^1$H-NMR (CDCl3): δ 7.96 (2H, d), 7.92 (2H, d), 7.75 (4H, d), 7.71 (2H, d), 7.02 (2H, d), 4.04 (2H, t), 1.82-1.24 (8H, m), 0.91 (3H, m). LC-MS: MH+ 384. UV-Vis in ethyl acetate 362 nm.

Synthesis of Chromophore 6

The novel azo-benzene chromophore (Chromophore 6) was synthesized according to the following synthesis scheme:

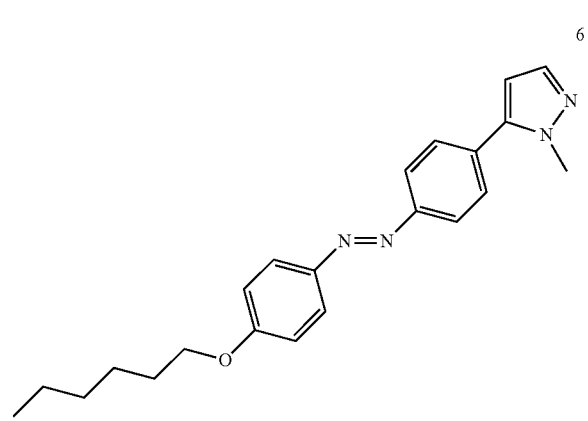 [SMILES: CCCCCCOc1ccc(/N=N/c2ccc(-c3ccnn3C)cc2)cc1]

A mixture of Intermediate E, ((E)-1-(4-bromophenyl)-2-(4-(hexyloxy)phenyl)diazene) (2.77 mmol), 1-methyl-5-(4,4,5,5-tetramethyl-1,3,2-dioxaborolan-2-yl)-1H-pyrazole (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.38 g (75%) of Chromophore 6, [(E)-5-(4-((4-(hexyloxy)phenyl)diazenyl)phenyl)-1-methyl-1H-pyrazole]. It was further purified by recrystallization. $^1$H-NMR (CDCl3): δ 7.95 (2H, d), 7.91 (2H, d), 7.56 (3H, m), 7.02 (2H, d), 6.38 (H, d), 4.04 (2H, t), 3.94 (3H, s), 1.82-1.24 (8H, m), 0.91 (3H, m). LC-MS: MH+ 363. UV-Vis in ethyl acetate 359 nm.

Synthesis of Chromophore 7

The novel azo-benzene chromophore (Chromophore 7) was synthesized according to the following synthesis scheme:

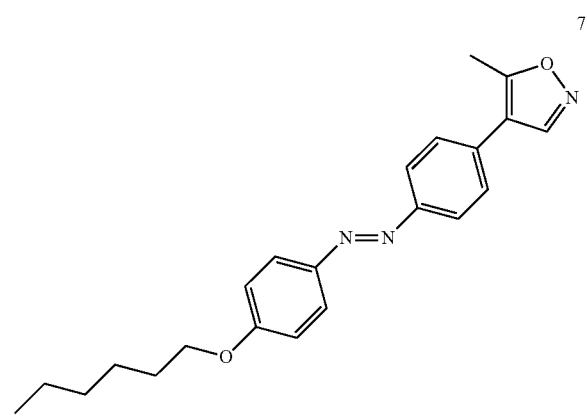 [SMILES: CCCCCCOc1ccc(/N=N/c2ccc(-c3cnoc3C)cc2)cc1]

A mixture of Intermediate E, ((E)-1-(4-bromophenyl)-2-(4-(hexyloxy)phenyl)diazene) (2.77 mmol), 3,5-dimethyl-4-(4,4,5,5-tetramethyl-1,3,2-dioxaborolan-2-yl)isoxazole (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.32 g (61%) of Chromophore 7, [(E)-4-(4-((4-(hexyloxy)phenyl)diazenyl)phenyl)-3,5-dimethylisoxazole]. It was further purified by recrystallization. $^1$H-NMR (CDCl3): δ 7.94 (2H, d), 7.90 (2H, d), 7.39 (2H, d), 7.01 (2H, d), 4.05 (2H, t), 2.45 (3H, s), 2.31 (3H, s), 1.82-1.24 (8H, m), 0.92 (3H, m). LC-MS: MH+ 378. UV-Vis in ethyl acetate 356 nm.

Synthesis of Intermediate F

The azo-benzene structure (Intermediate F) was synthesized according to the following synthesis scheme:

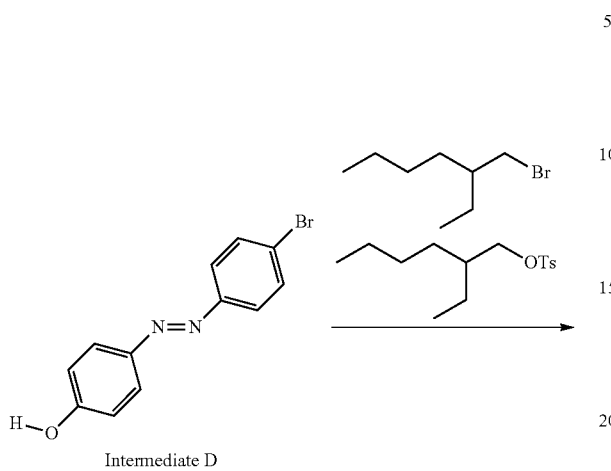

Intermediate D

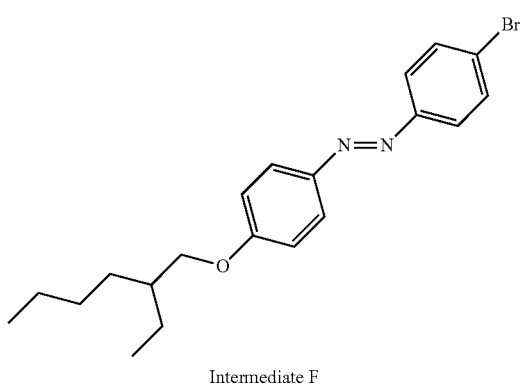

Intermediate F

A mixture of Intermediate D, 2-ethylhexyl 4-methylbenzenesulfonate (22.6 mmol), 4-nitrophenol (18 mmol), potassium carbonate (27 mmol), and DMF (anhydrous, 40 mL) is stirred under argon and heated at 80° C. until all nitrophenol is consumed. The reaction mixture is poured into ice/water (200 mL) and extracted with a mixture of hexane/ethyl acetate (200+200 mL). The extract is washed with water (200 mL), dried over magnesium sulfate, and the solvent is removed under reduced pressure. An orange solid is obtained and further purified by column chromatography. The yield was roughly 35-40% of Intermediate F. $^1$H-NMR (CDCl3): δ 8.19 (2H, d), 6.95 (2H, d), 3.92 (2H, t), 1.76 (H, m), 1.48-1.20 (8H, m), 0.90 (6H, m). LC-MS: MH+ 391. UV-Vis in EtOAc 353 nm.

Synthesis of Chromophore 8

The novel azo-benzene chromophore (Chromophore 8) was synthesized according to the following synthesis scheme:

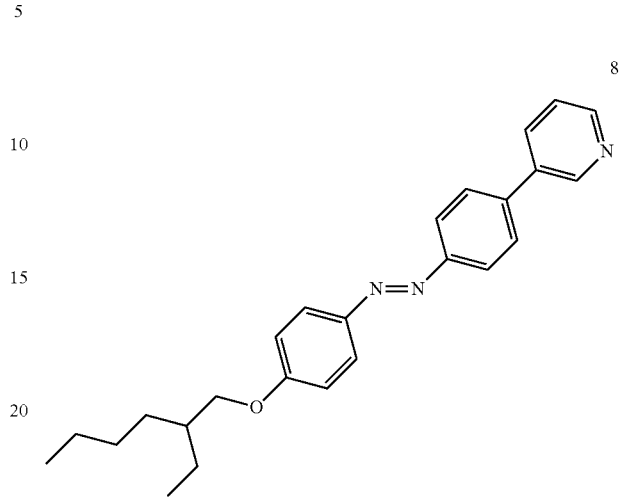

A mixture of Intermediate F, ((E)-1-(4-bromophenyl)-2-(4-((2-ethylhexyl)oxy)phenyl)diazene), (2.77 mmol), 4-cyanophenylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.63 g (85%) of Chromophore 8, [(E)-3-(4-((4-((2-ethylhexyl)oxy)phenyl)diazenyl)phenyl)pyridine]. It was further purified by recrystallization. $^1$H-NMR (CDCl3): δ 8.91 (H, d), 8.62 (H, m), 7.99 (5H, m), 7.73 (2H, d), 7.41 (H, m), 7.03 (2H, d), 3.94 (2H, d), 1.82-1.24 (9H, m), 0.94 (6H, m). LC-MS: MH+ 388. UV-Vis in ethyl acetate 360 nm.

Synthesis of Chromophore 9

The novel azo-benzene chromophore (Chromophore 9) was synthesized according to the following synthesis scheme:

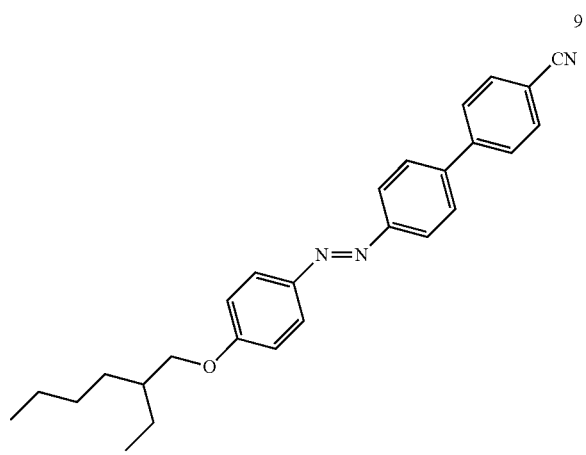 [SMILES: CCCCC(CC)COc1ccc(/N=N/c2ccc(-c3ccc(C#N)cc3)cc2)cc1]

A mixture of Intermediate F, ((E)-1-(4-bromophenyl)-2-(4-((2-ethylhexyl)oxy)phenyl)diazene), (2.77 mmol), 4-cyanophenylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 1.15 g (72%) of Chromophore 9, [(E)-4'-((4-((2-ethylhexyl)oxy)phenyl)diazenyl)-[1,1'-biphenyl]-4-carbonitrile]. It was further purified by recrystallization. $^1$H-NMR (CDCl3): δ 7.96 (2H, d), 7.92 (2H, d), 7.75 (4H, d), 7.73 (2H, d), 7.03 (2H, d), 3.93 (2H, d), 1.82-1.24 (9H, m), 0.92 (6H, m). LC-MS: MH+ 412. UV-Vis in ethyl acetate 363 nm.

Synthesis of Chromophore 10

The novel azo-benzene chromophore (Chromophore 10) was synthesized according to the following synthesis scheme:

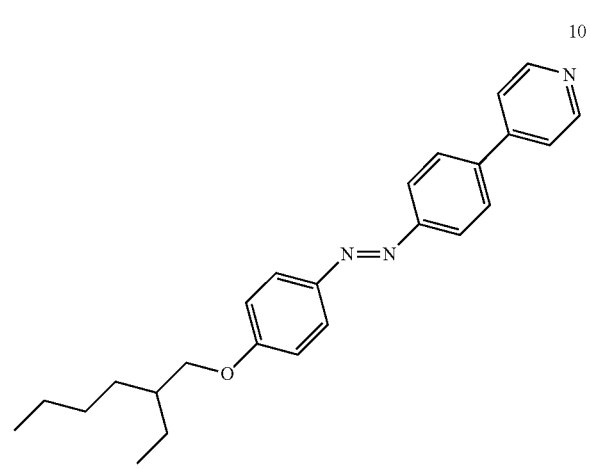 [SMILES: CCCCC(CC)COc1ccc(/N=N/c2ccc(-c3ccncc3)cc2)cc1]

A mixture of Intermediate F, ((E)-1-(4-bromophenyl)-2-(4-((2-ethylhexyl)oxy)phenyl)diazene) (2.77 mmol), pyridin-4-ylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.61 g (61%) of Chromophore 10 [(E)-4-(4-((4-((2-ethylhexyl)oxy)phenyl)diazenyl)phenyl)pyridine]. It was then further purified by recrystallization. $^1$H-NMR (CDCl3): δ 8.69 (2H, d), 7.99 (2H, d), 7.94 (2H, d), 7.78 (2H, d), 7.57 (2H, d), 7.03 (2H, d), 3.94 (2H, d), 1.82-1.24 (9H, m), 0.92 (6H, m). LC-MS: MH+ 388. UV-Vis in ethyl acetate 361 nm.

Synthesis of Chromophore 11

The novel azo-benzene chromophore (Chromophore 11) was synthesized according to the following synthesis scheme:

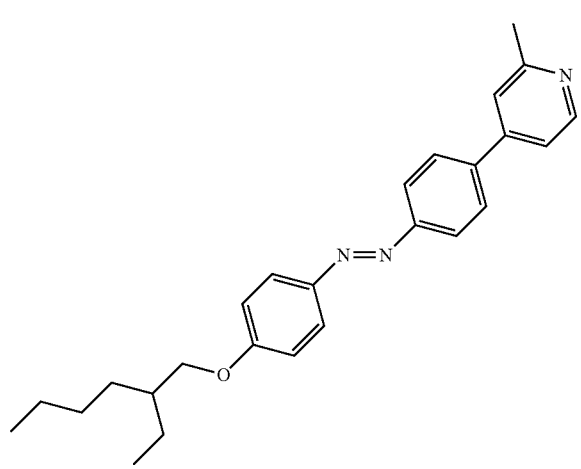

A mixture of Intermediate F, ((E)-1-(4-bromophenyl)-2-(4-((2-ethylhexyl)oxy)phenyl)diazene) (2.77 mmol), (2-methylpyridin-4-yl)boronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.22 g (31%) of Chromophore 11 [(E)-4-(4-((4-((2-ethylhexyl)oxy)phenyl)diazenyl)phenyl)-2-methylpyridine]. It was then further purified by recrystallization. $^1$H-NMR (CDCl3): δ 8.57 (1H, s), 7.98 (4H, m), 7.77 (2H, d), 7.42 (1H, s), 7.37 (1H, m), 7.02 (2H, d), 3.94 (2H, d), 2.63 (3H, s), 1.82-1.24 (9H, m), 0.94 (6H, m). LC-MS: MH+ 402. UV-Vis in ethyl acetate 361 nm.

Synthesis of Chromophore 12

The novel azo-benzene chromophore (Chromophore 12) was synthesized according to the following synthesis scheme:

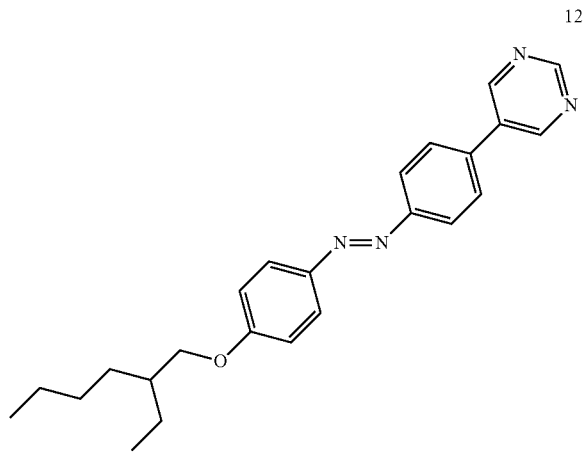 [SMILES: CCCCC(CC)COc1ccc(/N=N/c2ccc(-c3cncnc3)cc2)cc1]

A mixture of Intermediate F ((E)-1-(4-bromophenyl)-2-(4-((2-ethylhexyl)oxy)phenyl)diazene) (2.77 mmol), pyrimidin-5-ylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.57 g (57%) of Chromophore 12 [(E)-5-(4-((4-((2-ethylhexyl)oxy)phenyl)diazenyl)phenyl)pyrimidine]. It was then further purified by recrystallization. $^1$H-NMR (CDCl3): δ 9.23 (1H, d), 9.02 (2H, d), 8.00 (2H, d), 7.93 (2H, d), 7.73 (2H, d), 7.03 (2H, d), 3.94 (2H, d), 1.82-1.24 (9H, m), 0.92 (6H, m). LC-MS: MH+ 389. UV-Vis in ethyl acetate 361 nm.

Synthesis of Chromophore 13

The novel azo-benzene chromophore (Chromophore 13) was synthesized according to the following synthesis scheme:

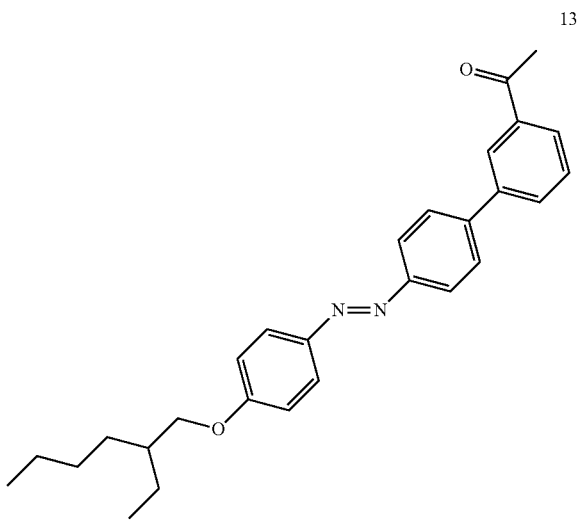 [SMILES: CCCCC(CC)COc1ccc(/N=N/c2ccc(-c3cccc(C(C)=O)c3)cc2)cc1]

A mixture of Intermediate F ((E)-1-(4-bromophenyl)-2-(4-((2-ethylhexyl)oxy)phenyl)diazene) (2.77 mmol), (3-acetylphenyl)boronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.49 g (45%) of Chromophore 13 [(E)-1-(4'-((4-((2-ethylhexyl)oxy)phenyl)diazenyl)-[1,1'-biphenyl]-3-yl)ethanone]. It was then further purified by recrystallization. $^1$H-NMR (CDCl3): δ 8.24 (1H, s), 7.98 (5H, m), 7.86 (1H, d), 7.76 (2H, d), 7.58 (1H, t), 7.02 (2H, d), 3.93 (2H, d), 2.67 (3H, s), 1.82-1.24 (9H, m), 0.96 (6H, m). LC-MS: MH+ 429. UV-Vis in ethyl acetate 361 nm.

Synthesis of Chromophore 14

The novel azo-benzene chromophore (Chromophore 14) was synthesized according to the following synthesis scheme:

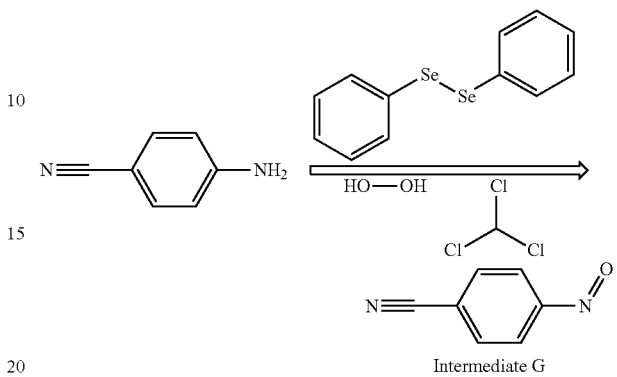

To a stirring 100 mL solution of chloroform at room temperature, added 27.10 g (229 mmol, 1 eq) of the 4-Aminobenzonitrile. Shortly after dissolution, 100 g (1029 mmol, 4.5 eq) of the 35 wt % hydrogen peroxide and 3.24 g of diphenyl diselenide (10 mmol, 0.04 eq) were added. The mixture was reacted overnight, and then the precipitate was filtered. The precipitate was put in 300 mL of hexanes and stirred for about 10 minutes at room temperature, and then filtered again, and then the collected precipitate was immediately put in the refrigerator. Due to the sensitive nature of the nitroso compound, the material couldn't be dried to get an exact weight for the yield calculations (or NMR Analysis). However, the yield of Intermediate G can be estimated to be over 90%.

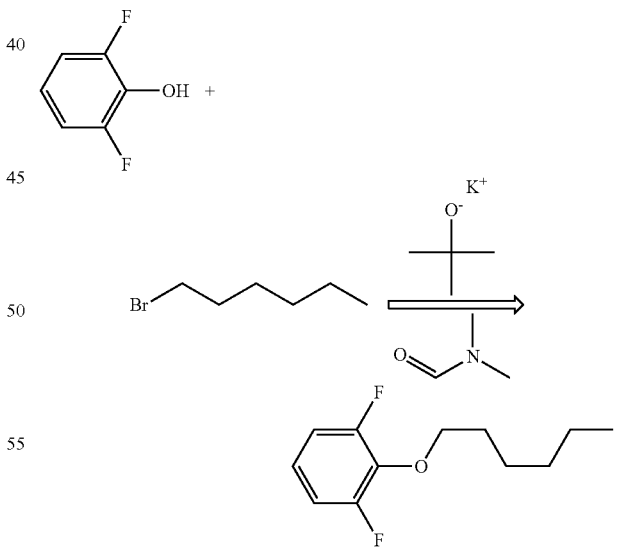

To a stirring quantity of 200 mL of DMF at room temperature, added 20 g (154 mmol, 1 eq) of the 2,6-Difluorophenol. Subsequently added 40 mL (285 mmol, 1.85 eq) of the bromohexane and followed it by the addition of 30 g (267 mmol, 1.73 eq) of the base, and then the mixture was put in a 80° C. pre-heated bath. After 4 hours of reaction, the reaction was poured over 800 mL of ice water and 1 L of ether. 33.19 g of a transparent liquid was obtained. Yield was quantitative. $^1$H-NMR (TCE): ☐ 0.88 (3H, t), 1.30 (4H, m), 1.43 (2H, m), 1.73 (2H, m), 4.10 (2H, t), 6.90 (3H, m).

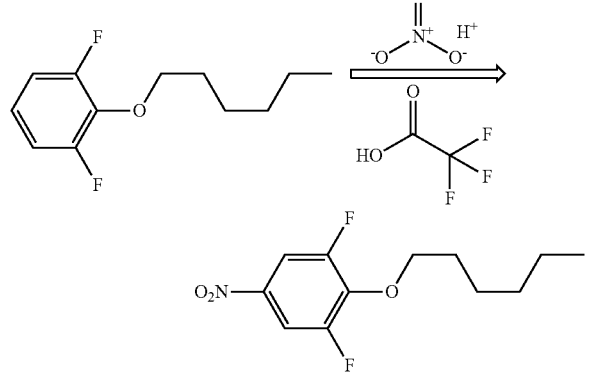

To a 0° C. cooled, stirring solution of 200 mL TFA, added 33 g (154 mmol, 1 eq) of the cooled difluoroether. To cooled 130 mL of TFA added 13.2 g (147 mmol, 0.95 eq) of 70% HNO$_3$. Added the nitric acid solution dropwise to the fluoroether solution. After the addition completed, let the solution warm to room temperature. After 1 hour, poured reaction over 1.5 L of ice water. Extracted with 1.5 L of ether. The organic layer was collected and neutralized of residual acid with sodium bicarbonate. Purified by column chromatography 9Hex:1 DCM. 22.43 g of a greenish transparent liquid was obtained. Yield was quantitative. $^1$H-NMR (TCE): ☐ 0.88 (3H, t), 1.31 (4H, m), 1.42 (2H, m), 1.76 (2H, m), 4.31 (2H, t), 7.84 (2H, m).

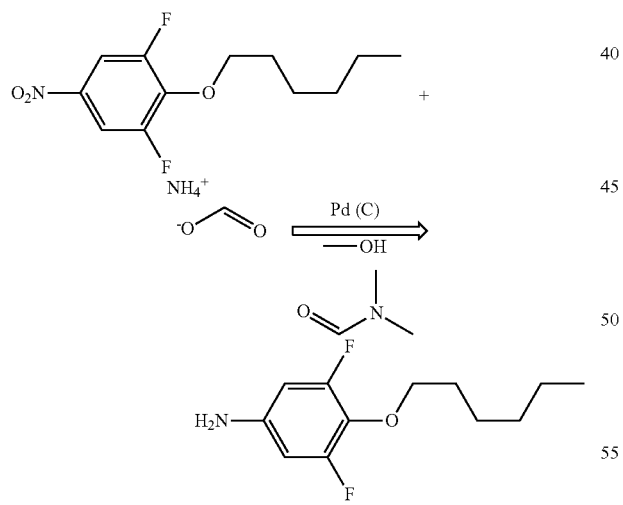

To a stirring mixture of 100 mL of DMF and 100 mL of MeOH, added 22 g (85 mmol, 1 eq) of the nitroether. Added the 26.8 g (425 mmol, 5 eq) of the NH$_4$HCO$_2$. And finally added 1 g Pd (10 wt % on carbon) (CAUTION: add very slowly AND in 0.5 g portions-fire hazard!). After 30 minutes of reaction at room temperature, poured reaction over 1 L of water. Extracted this mixture with 1 L of ether. Purified the material using 1Hex: 1 DCM. 16.95 g of a yellowish-white, crumby powder was obtained. Yield was 87%. $^1$H-NMR (DMSO): ☐ 0.86 (3H, t), 1.27 (4H, m), 1.38 (2H, m), 1.59 (2H, m), 3.83 (2H, t), 5.39 (2H, s), 6.21 (2H, m).

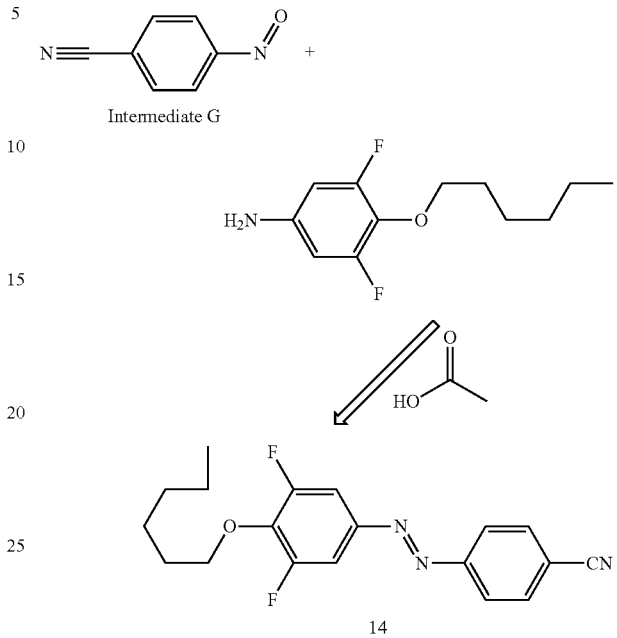

To a stirring solution of 200 mL of glacial acetic acid at room temperature, added 16.5 g (72 mmol, 1 eq) of the aminoether. Subsequently added 50 g of the nitroso compound. After 5 hours of reaction, poured reaction over 2 L of cooled water (with NaOH) to neutralize the acid. Extracted with 1.5 L of ether. Collected the organic layer and performed column chromatography using 1Hex: 1 DCM. 12.24 g of a light orange powder, Chromophore 14, was obtained. Yield was 50%. $^1$H-NMR (TCE): ☐ 0.89 (3H, t), 1.32 (4H, m), 1.45 (2H, m), 1.77 (2H, m), 4.26 (2H, t), 7.60 (2H, m), 7.81 (2H, d), 7.95 (2H, d).

Synthesis of Chromophore 15

The novel azo-benzene chromophore (Chromophore 15) was synthesized according to the following synthesis scheme:

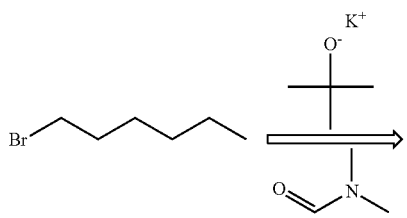

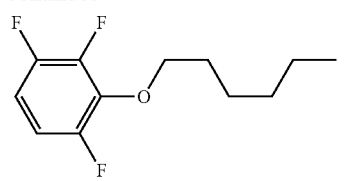

To a stirring quantity of 100 mL of DMF at room temperature, added 15 g (101 mmol, 1 eq) of the trifluorophenol. Subsequently added 30 mL (214 mmol, 2.1 eq) of the bromohexane and followed it by the addition of 25 g (223 mmol, 2.2 eq) of the base. After 1 overnight of reaction, poured reaction over 500 mL of water (with KOH). Extracted with 500 mL of ether. The organic layer was collected and rotovaped. Performed column chromatography using 9Hex: 1 DCM to elute the product. 23.01 g of a transparent liquid was obtained. Yield was quantitative. $^{1}$H-NMR (TCE): ☐ 0.88 (3H, t), 1.30 (4H, m), 1.44 (2H, m), 1.73 (2H, m), 4.14 (2H, t), 6.82 (2H, m).

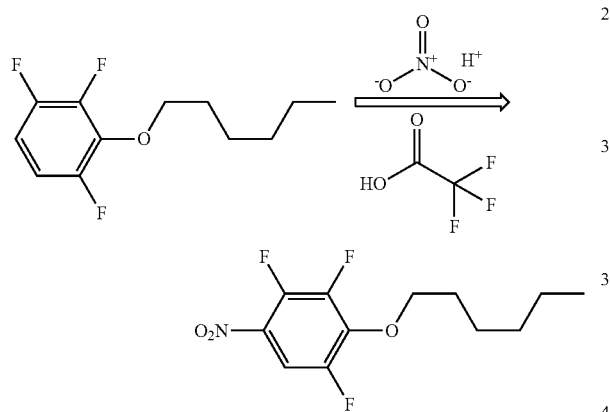

To a 0° C. cooled, stirring solution of 250 mL TFA, added 26.01 g (112 mmol, 1 eq) of the trifluoro ether. To this solution added 15 g (167 mmol, 1.5 eq) of 70% HNO$_3$ dropwise. After the addition completed, let the solution warm to room temperature and then placed in a 60° C. bath. After 2 hours, TLC (1Hex: 1 DCM, R$_f$=0.8) indicated reaction incomplete. Added an additional 4.83 g of 70% HNO$_3$ dropwise. After 45 minutes of additional reaction, poured reaction over 800 mL of cooled water (with KOH dissolved) to neutralize the acid. Extracted this solution with 800 mL of ether. Performed column chromatography using 9Hex:1 DCM. 20.65 g of a viscous greenish-yellow transparent liquid was obtained. Yield was 66%. $^{1}$H-NMR (TCE): ☐ 0.88 (3H, t), 1.31 (4H, m), 1.44 (2H, m), 1.77 (2H, m), 4.37 (2H, t), 7.73 (1H, m).

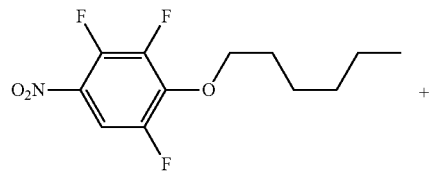 +

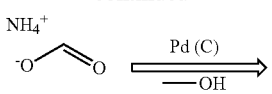

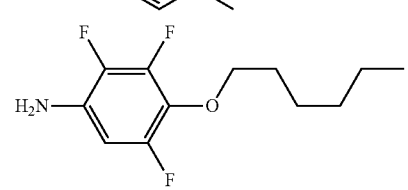

To a stirring solution of 100 mL of DMF at room temperature, dissolved 10 g (36 mmol, 1 eq) of the nitroether. Added 52 g (825 mmol, 23 eq) of the ammonium formate. Added 1 g Pd (10 wt % on carbon) (CAUTION: add very slowly AND in 0.5 g portions-fire hazard!). Slowly added 25 mL of methanol. After 40 minutes of reaction, filtered the solution over celite. Washed the celite with a few milliliters of THF to extract all of the amine. Performed column chromatography using 4Hex:1 DCM. 6.65 g of a viscous brown oil was obtained. Yield was 74%. $^{1}$H-NMR (DMSO): ☐ 0.85 (3H, t), 1.27 (4H, m), 1.39 (2H, m), 1.61 (2H, m), 3.91 (2H, t), 6.43 (1H, m).

Intermediate G

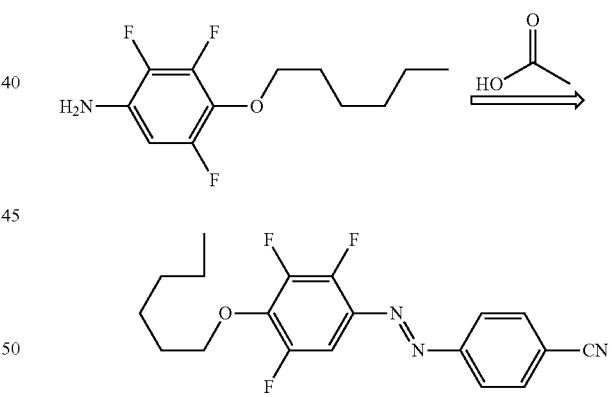

15

A stirring solution of 100 mL of glacial acetic acid at room temperature was combined with 25 g of the nitroso (Intermediate G) with 6.65 g (27 mmol, 1 eq) amino ether. Subsequently added 20 g of the nitroso compound. Put in 50° C. bath. After 2 hours of reaction, extracted the mix with 800 mL of cooled water (with KOH) to neutralize the acid and extracted with 600 mL of ether. Collected the organic layer and performed column chromatography using 4Hex: 1 DCM. 2.14 g of a light orange powder, Chromophore 15, was obtained. Yield was 7.4%. $^{1}$H-NMR (TCE): ☐ 0.89 (3H, t), 1.31 (4H, m), 1.45 (2H, m), 1.79 (2H, m), 4.31 (2H, t), 7.42 (1H, m), 7.83 (2H, d), 8.00 (2H, d).

Synthesis of Chromophore 16

The novel azo-benzene chromophore (Chromophore 16) was synthesized according to the following synthesis scheme:

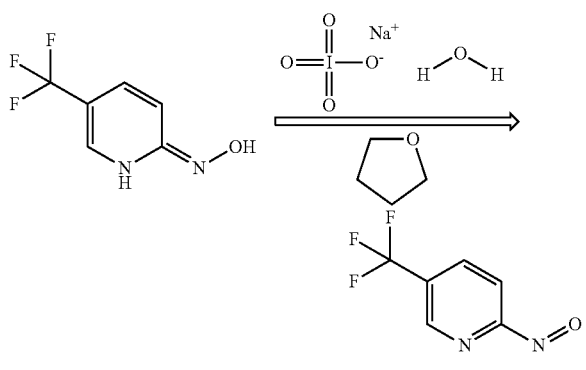

To a stirring 20 mL solution of THF at room temperature, added 1 g (5.6 mmol, 1 eq) of the fluoropyridine. Dissolved 0.96 g (4.5 mmol, 0.8 eq) of the sodium periodate in 10 mL of water. Cooled both solutions to 0° C. Added the periodate solution dropwise to the THF solution. After 30 minutes, added 50 mL of water to the reaction mixture. Filtered the precipitate. 1 g of a yellow precipitate was obtained. Yield was quantitative.

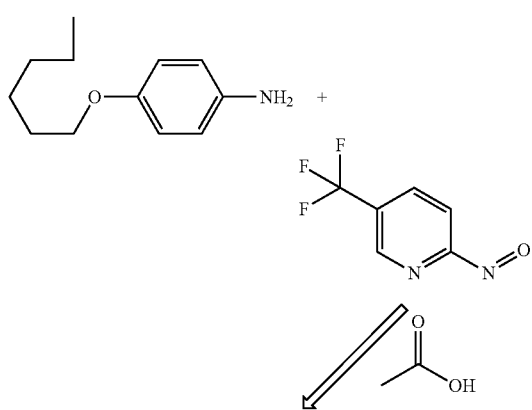

To a stirring solution of 20 mL of glacial acetic acid at room temperature, added 1 g (5.2 mmol, 1 eq) of the aminoether. Subsequently added 0.90 g (5.2 mmol, 1 eq) of the nitroso compound. After 1.5 hours of reaction, extracted the mix with 200 mL of ether and 200 mL of water. Collected the organic layer and performed column chromatography using just hexanes to pack the column and then changing gradient of 9:1 hexane: ethyl acetate to 7:3 hexane: ethyl acetate to 1:1 hexane: ethyl acetate. Purified a second time using 4:1 hexane:ethyl acetate. 250 mg of an orange powder, Chromophore 16, was obtained. Yield was 14%.

$^1$H-NMR (TCE): ☐ 0.90 (3H, t), 1.34 (4H, m), 1.45 (2H, m), 1.81 (2H, m), 4.05 (2H, t), 7.05 (2H, d), 7.85 (1H, d), 8.06 (3H, m), 8.93 (1H, s).

Synthesis of Chromophore 17

The novel azo-benzene chromophore (Chromophore 17) was synthesized according to the following synthesis scheme:

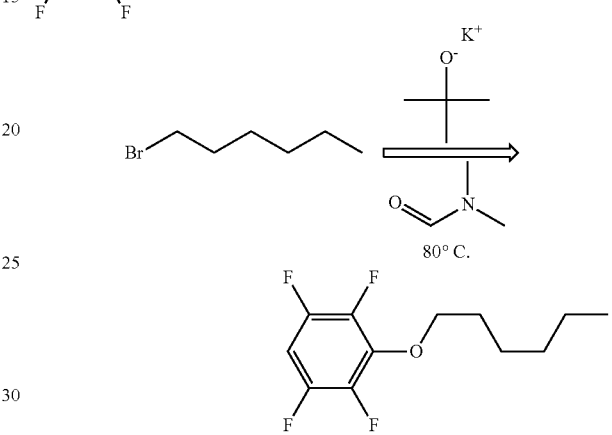

To a stirring quantity of 150 mL of DMF at room temperature, added 25 g (150 mmol, 1 eq) of the tetrafluorophenol. Subsequently added 35 mL (250 mmol, 1.7 eq) of the bromohexane and followed it by the addition of 28 g (250 mmol, 1.7 eq) of the base. Put in 80° C. bath. After 2 hours of reaction, TLC (1Hex: 1 DCM, R$_f$=0.9) indicated completion of reaction. Poured reaction over 1 L of water. Extracted with 700 mL of ether. Collected organic layer and rotovaped. Performed column chromatography using 9Hex: 1 DCM to elute the product. 34.83 g of a transparent liquid was obtained. Yield was 92%. $^1$H-NMR (TCE): ☐ 0.88 (3H, t), 1.30 (4H, m), 1.43 (2H, m), 1.74 (2H, m), 4.19 (2H, t), 6.79 (1H, m).

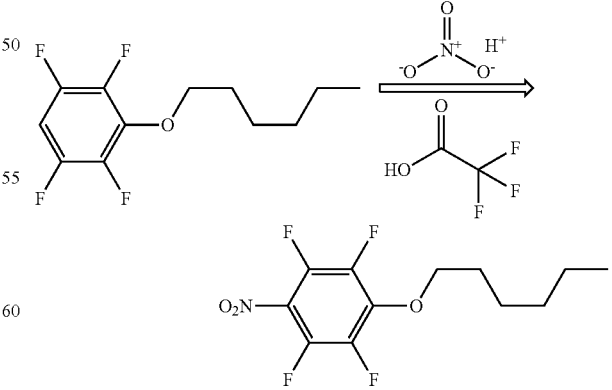

To a 0° C. cooled, stirring solution of 200 mL TFA, added 30 g (120 mmol, 1 eq) of the tetrafluoro ether. To this solution added 11.8 g (132 mmol, 1.1 eq) of 70% HNO$_3$ in 100 mL of cooled TFA dropwise. After the addition completed, let the solution warm to room temperature. Put the reaction in 60° C. bath. After 1.5 hours, TLC (9Hex: 1 DCM, $R_f$=0.8) indicated reaction incomplete. Added an additional 12.45 g of 70% $HNO_3$ dropwise. After 3.5 additional hour of reaction, poured reaction over 1 L of cooled water (with KOH dissolved) to neutralize the acid. Extracted this solution with 1 L of ether. Performed column chromatography using 9Hex:1 DCM. 3 g of a yellow transparent liquid was obtained. Yield was 8%. $^1$H-NMR (TCE): □ 0.88 (3H, t), 1.30 (4H, m), 1.46 (2H, m), 1.77 (2H, m), 4.37 (2H, t).

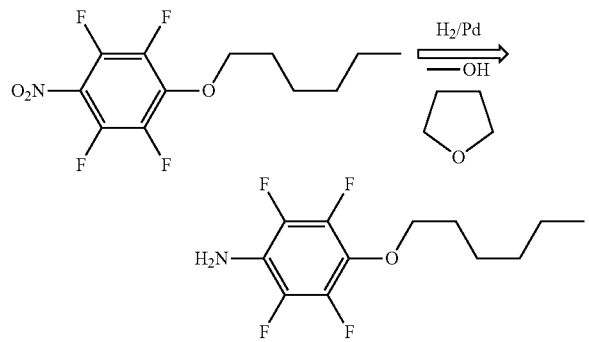

To a stirring solution of 100 mL of THF, dissolved 3 g (10 mmol, 1 eq) of the nitroether. Added 1 g Pd (10 wt % on carbon) (CAUTION: add very slowly AND in 0.5 g portions-fire hazard!). Added 25 mL of methanol. Put the reaction mixture under 50 psi of hydrogen in the hydrogenator. After 25 minutes, added 50 mL of DCM to quench the reaction. The solution filtered over celite and then rotovaped. 2.64 g of a brown viscous wax was obtained. Yield was quantitative. $^1$H-NMR (DMSO): □ 0.86 (3H, t), 1.27 (4H, m), 1.39 (2H, m), 1.65 (2H, m), 3.97 (2H, t), 5.7 (2H, s).

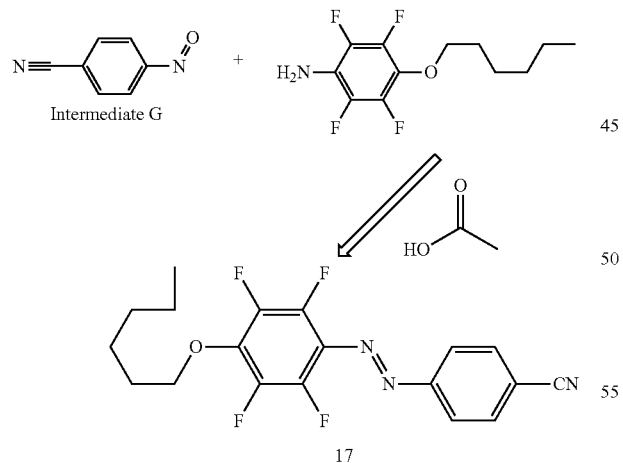

To a stirring solution of 50 mL of glacial acetic acid at room temperature, added 2.64 g (10 mmol, 1 eq) of the amino ether. Subsequently added 20 g of the nitroso (Intermediate G) compound. Put in 60° C. bath. After 2 hours of reaction at room temperature, extracted the mix with 400 mL of cooled water (with KOH) to neutralize the acid and extracted with 400 mL of ether. Collected the organic layer and performed column chromatography using 9Hex: 1 DCM. 280 mg of a light orange powder, Chromophore 17, was obtained. Yield was 7.4%. $^1$H-NMR (TCE): □ 0.89 (3H, t), 1.31 (4H, m), 1.45 (2H, m), 1.79 (2H, m), 4.35 (2H, t), 7.84 (2H, d), 7.99 (2H, d).

Synthesis of Chromophore 18

The novel azo-benzene chromophore (Chromophore 18) was synthesized according to the following synthesis scheme:

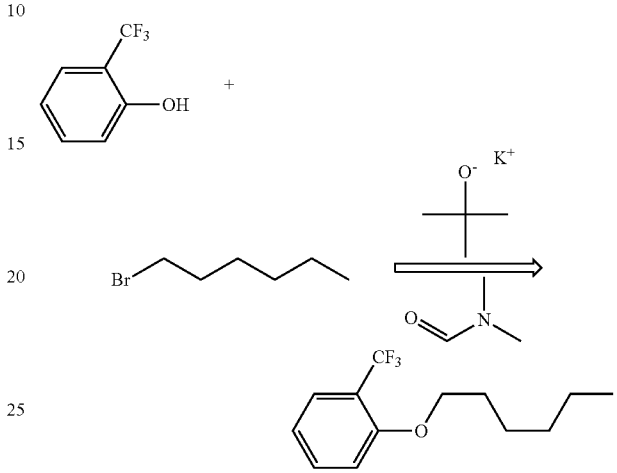

To a stirring quantity of 100 mL of cooled DMF at room temperature, added 25 g (154 mmol, 1 eq) of trifluorophenol. Subsequently added 32.5 mL (231 mmol, 1.5 eq) of the bromohexane and followed it by the addition of 26 g (232 mmol, 1.5 eq) of the base. After 2.5 hours of reaction, TLC (1Hex: 1 DCM, $R_f$=0.9) indicated completion of reaction. Poured reaction over 800 mL of water (with 10 g KOH dissolved in it). Extracted with 800 mL of ether. Collected organic layer and rotovaped. Performed column chromatography using 9Hex: 1 DCM to elute the product. Obtained 38.92 g of a transparent liquid. Yield was quantitative. $^1$H-NMR (TCE): □ 0.88 (3H, t), 1.31 (4H, m), 1.45 (2H, m), 1.80 (2H, m), 4.02 (2H, t), 6.98 (2H, m), 7.47 (1H, t), 7.55 (1H, d).

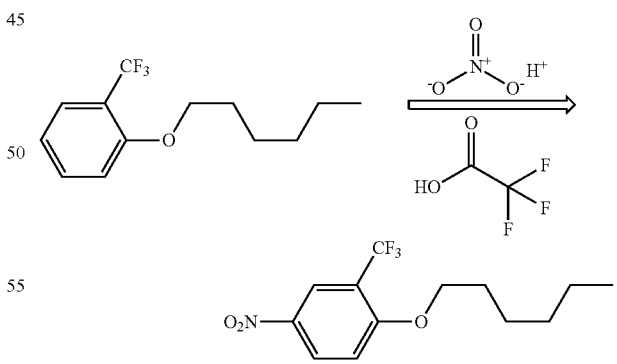

To a 0° C. cooled, stirring solution of 38 g (154 mmol, 1 eq) of the trifluoroether, added 200 mL TFA. To this solution added 11.1 g (123 mmol, 0.8 eq) of 70% $HNO_3$ dropwise. After the addition completed, let the solution warm to room temperature. After 40 minutes of stirring at room temperature, reaction was stopped and TLC (9Hex: 1 DCM, $R_f$=0.5) indicated reaction incomplete. Added an additional 2.48 g of 70% $HNO_3$ dropwise. After 1 additional hour of stirring, poured reaction over 800 mL of cooled water (with KOH dissolved) to neutralize the acid. Extracted this solution with 800 mL of ether. Performed column chromatography twice using 9Hex:1 DCM. Obtained 7 g of a brownish-orange viscous liquid. Yield was 16%. $^1$H-NMR (TCE): ☐ 0.88 (3H, t), 1.30 (4H, m), 1.46 (2H, m), 1.83 (2H, m), 4.14 (2H, t), 7.05 (1H, d), 8.38 (1H, d), 8.45 (1H, d).

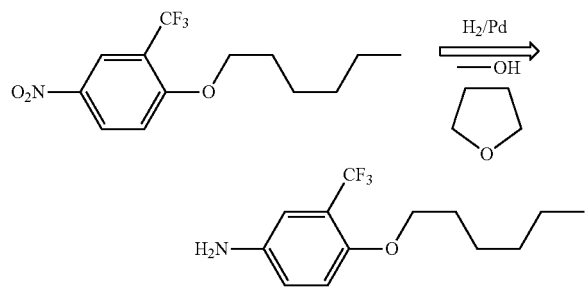

To a stirring solution of 100 mL of THF, dissolved 7 g (24 mmol, 1 eq) of the nitroether. Added 1 g Pd (10 wt % on carbon) (CAUTION: add very slowly AND in 0.5 g portions-fire hazard!). 25 mL of methanol was added. The reaction mixture was put under 50 psi of hydrogen in the hydrogenator. After 15 minutes, added 100 mL of DCM to quench the reaction. TLC (1Hex:1 DCM, $R_f$=0.5) indicated completion of reaction. The solution was filtered over celite and then rotovaped. About 6.6 g of a greenish-brown transparent liquid was obtained. Yield was quantitative. $^1$H-NMR (TCE): ☐ 0.86 (3H, t), 1.29 (4H, m), 1.42 (2H, m), 1.74 (2H, m), 2.95 (2H, s), 3.9 (2H, t), 6.80 (2H, m), 6.88 (1H, d).

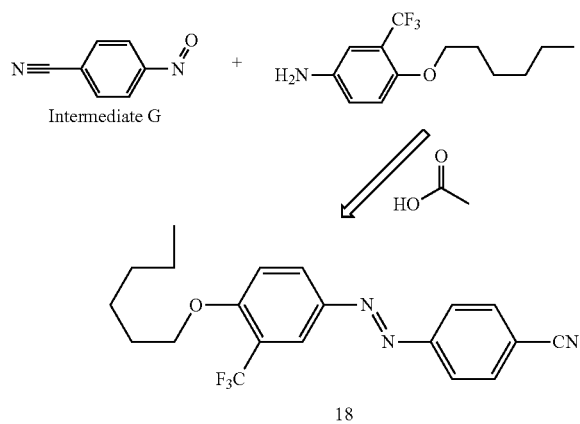

To a stirring solution of 100 mL of glacial acetic acid at room temperature, added 36 g of the nitroso compound (Intermediate G). Subsequently added 6.37 g (48 mmol, 1 eq) of the amino ether. After 4 hours of reaction at room temperature, the mixture was extracted with 500 mL of cooled water (with KOH) to neutralize the acid and then extracted with 500 mL of ether. Collected the organic layer and performed column chromatography using 4Hex: 1 DCM. 4.78 g of an orange powder was obtained, Chromophore 18. Yield was >26%. $^1$H-NMR (TCE): ☐ 0.89 (3H, t), 1.32 (4H, m), 1.48 (2H, m), 1.83 (2H, m), 4.14 (2H, t), 7.10 (1H, d), 7.80 (2H, d), 7.96 (2H, d), 8.1 (1H, d), 8.2 (1H, s).

Synthesis of Chromophore 19

The novel azo-benzene chromophore (Chromophore 19) was synthesized according to the following synthesis scheme:

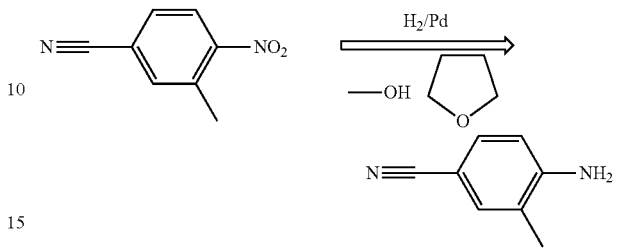

To a stirring 100 mL solution of THF at room temperature, added 9.89 g (61 mmol, 1 eq) of the benzonitrile. Then added 1 g palladium over 10% carbon. Then added 25 mL of methanol. The system was then put under 50 psi of pressure in a hydrogenator. After no more hydrogen consumption was observed, the reaction was stopped and filtered over celite. Performed column chromatography using 1:1 hexane:dichloromethane as the mobile phase. Obtained 7.5 g of a beige powder. Yield was 93%. $^1$H-NMR (DMSO): ☐ 2.27 (3H, s), 6.06 (2H, s), 6.41 (1H, d), 6.46 (1H, s), 7.30 (1H, d).

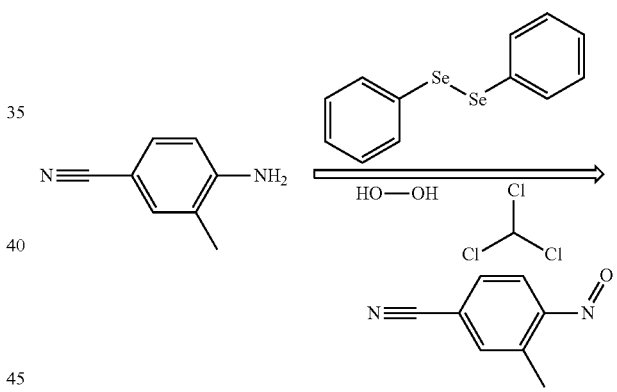

To a stirring 100 mL solution of chloroform at room temperature, added 7.50 g (57 mmol, 1 eq) of the 4-Aminobenzonitrile. Shortly after dissolution, added 40 mL (364 mmol, 6.4 eq) of the 35% by wt hydrogen peroxide and subsequently followed by 1.5 g of diphenyl diselenide (4.8 mmol, 0.08 eq). After one overnight of reaction, collected the organic layer. Due to the sensitive nature of the nitroso compound, the material couldn't be dried to get an exact weight for the yield calculations (or NMR analysis).

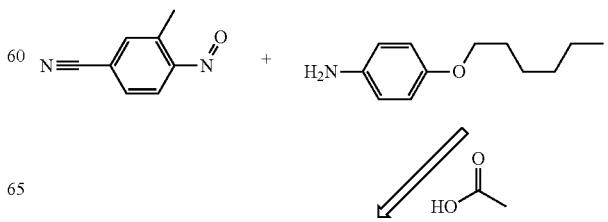

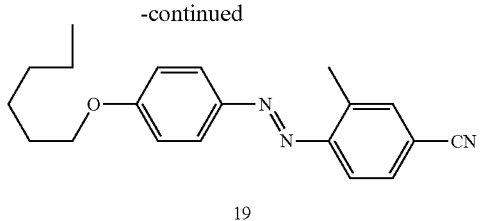

19

To a stirring solution of 300 mL of glacial acetic acid at room temperature, added 12 g (62 mmol, 1 eq) of the aminoether. Subsequently added all of the nitroso compound (the collected solution from previous reaction). After 1 hour of reaction, poured solution over 600 mL of cooled water (with KOH to neutralize the acid) and extracted with 800 mL of ether. Collected the organic layer and performed column chromatography using 7:3 Hexane: dichloromethane. Performed a second round of column chromatography using only toluene to elute the product. Obtained 8.58 g of a red-orange powder Chromophore 19 (along with 1.92 g of an impure batch). Yield was >43%. $^1$H-NMR (TCE): ☐ 0.92 (3H, t), 1.33 (4H, m), 1.45 (2H, m), 1.81 (2H, m), 2.62 (3H, s), 4.05 (2H, t), 7.02 (2H, d), 7.70 (2H, m), 7.78 (1H, s), 7.94 (2H, m).

Synthesis of Intermediate H

The azo-benzene structure (Intermediate H) was synthesized according to the following synthesis scheme:

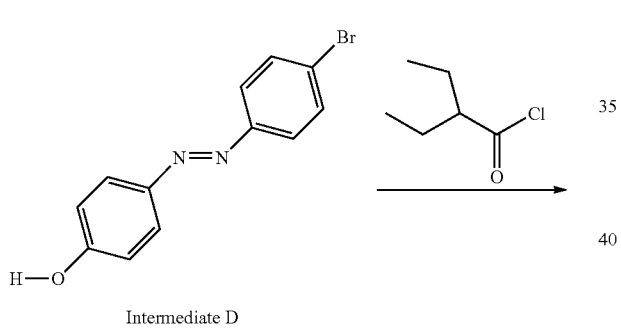

Intermediate D

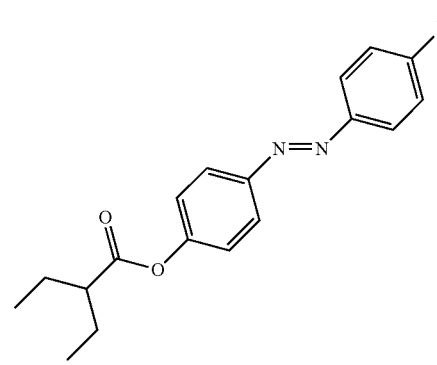

Intermediate H

A mixture of (E)-4-((4-bromophenyl)diazenyl)phenol (Intermediate D) (3.6 mmol), 2-ethylbutanoyl chloride (3.6 mmol), triethylamine (3.6 mL), and THF (anhydrous, 40 mL) is stirred under room temperature. The reaction mixture is poured into ice/water (200 mL) and extracted with a mixture of hexane/ethyl acetate (200+200 mL). The extract is washed with water (200 mL), dried over magnesium sulfate, and the solvent is removed under reduced pressure. Obtained orange solid from column as Intermediate H. The yield was 88%. $^1$H-NMR (CDCl3): δ 7.95 (2H, d), 7.77 (2H, d), 7.65 (2H, d), 7.23 (2H, d), 2.49 (1H, m), 1.81-1.58 (4H, m), 1.06 (6H, t). qLC-MS: MH+ 377. UV-Vis in ethyl acetate 330 nm.

Synthesis of Chromophore 20

The azo-benzene chromophore (Chromophore 20) was synthesized according to the following synthesis scheme:

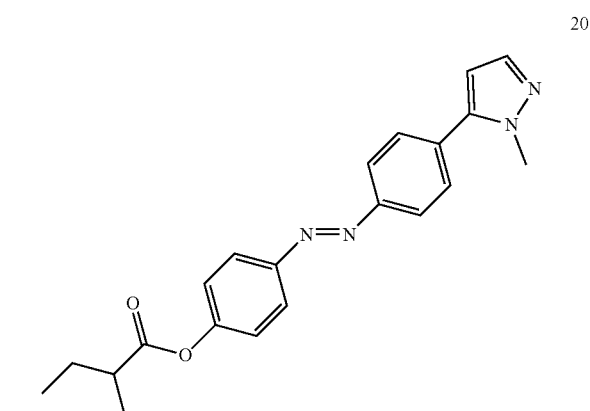

20

A mixture of ((E)-4-((4-bromophenyl)diazenyl)phenyl 2-ethylbutanoate (Intermediate H) (2.77 mmol), 1-methyl-5-(4,4,5,5-tetramethyl-1,3,2-dioxaborolan-2-yl)-1H-pyrazole (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.4 g (80%) of Chromophore 20, (E)-4-((4-(1-methyl-1H-pyrazol-5-yl)phenyl)diazenyl)phenyl 2-ethylbutanoate. The compound was further purified by recrystallization. $^1$H-NMR (CDCl3): δ 7.99 (4H, m), 7.58 (4H, m), 7.23 (1H, s), 6.39 (1H, s), 3.95 (3H, s), 2.49 (1H, m), 1.81-1.58 (4H, m), 1.06 (6H, t). LC-MS: MH+ 377. UV-Vis in ethyl acetate 340 nm.

Synthesis of Chromophore 21

The azo-benzene chromophore (Chromophore 21) was synthesized according to the following synthesis scheme:

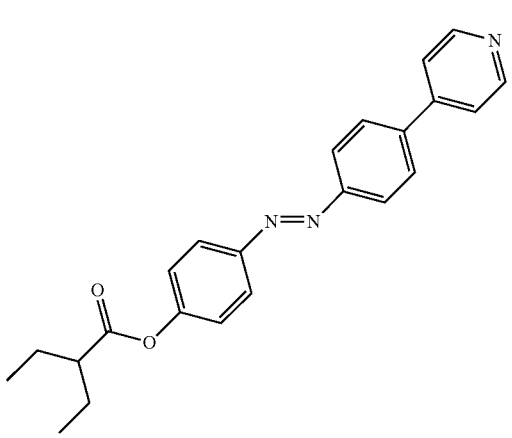

21

A mixture of (E)-4-((4-bromophenyl)diazenyl)phenyl 2-ethylbutanoate (Intermediate H) (2.77 mmol), pyridin-4-ylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.31 g (52%) of Chromophore 21, (E)-4-((4-(pyridin-4-yl)phenyl)diazenyl)phenyl 2-ethylbutanoate. The compound was further purified by recrystallization. $^1$H-NMR (CDCl3): δ 8.70 (2H, d), 8.01 (4H, m), 7.80 (2H, d), 7.57 (2H, d), 7.24 (2H, d), 2.49 (1H, m), 1.81-1.58 (4H, m), 1.06 (6H, t). LC-MS: MH+ 374. UV-Vis in ethyl acetate 338 nm.

Synthesis of Chromophore 22

The azo-benzene chromophore (Chromophore 22) was synthesized according to the following synthesis scheme:

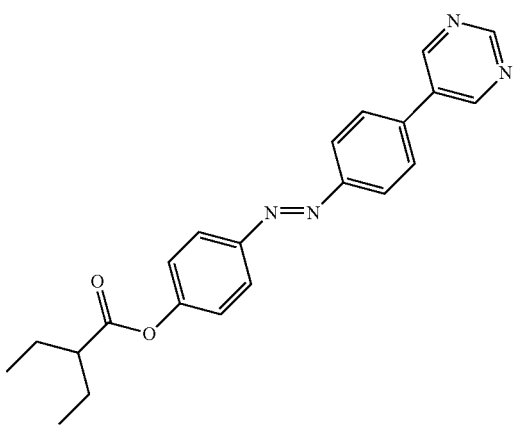

22

A mixture of (E)-4-((4-bromophenyl)diazenyl)phenyl 2-ethylbutanoate (Intermediate H) (2.77 mmol), pyrimidin-5-ylboronic acid (3.6 mmol), a solution of sodium carbonate (7 mmol) in water (3 mL), tetrakis(triphenylphosphine)palladium(0) (0.139 mmol), ethanol (12 mL), and toluene (25 mL) was stirred under argon and heated at 100° C. for 3 hours. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (1:1) as an eluent to give 0.78 g (78%) of Chromophore 22, (E)-4-((4-(pyrimidin-5-yl)phenyl)diazenyl)phenyl 2-ethylbutanoate. The compound was further purified by recrystallization. $^1$H-NMR (CDCl3): δ 9.24 (1H, d), 9.02 (2H, d), 8.07 (2H, d), 8.00 (2H, d), 7.75 (2H, d), 7.26 (2H, d), 2.49 (1H, m), 1.81-1.58 (4H, m), 1.06 (6H, t). LC-MS: MH+ 375. UV-Vis in ethyl acetate 337 nm.

Synthesis of Chromophore 23 and Chromophore 24

The azo-benzene chromophores (Chromophore 32 and Chromophore 33) were synthesized according to the following synthesis scheme:

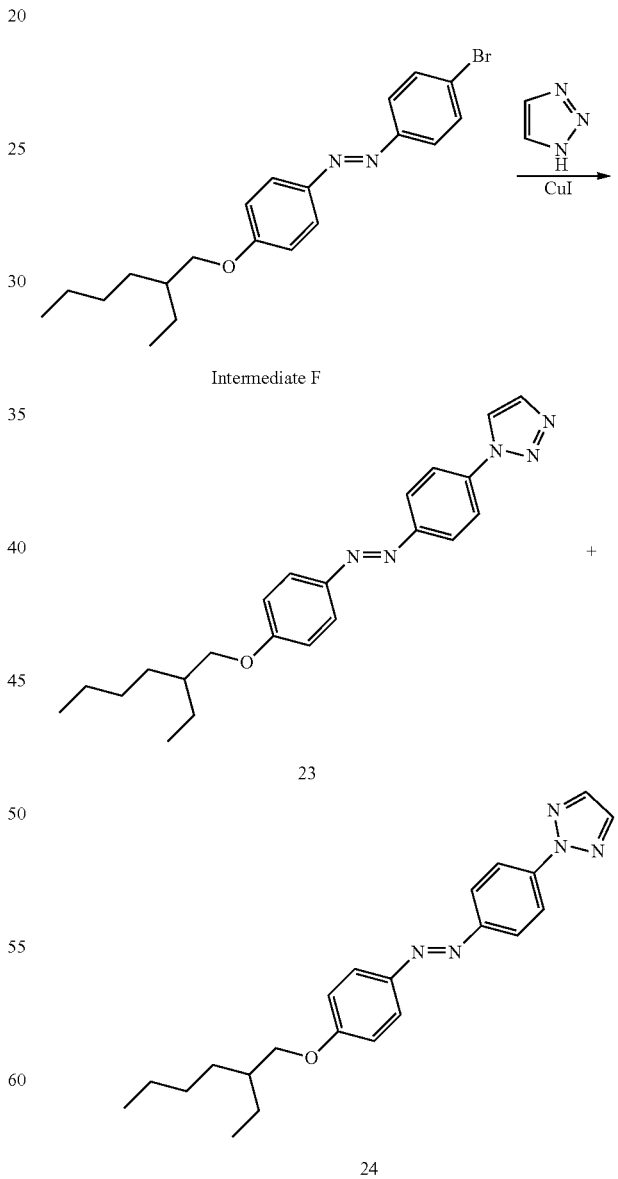

Intermediate F

23

24

A mixture of Intermediate F ((E)-1-(4-bromophenyl)-2-(4-((2-ethylhexyl)oxy)phenyl)diazene) (2.57 mmol), 1H-1, 2,3-triazole (10 mmol), Trans-(1R,2R)N,N'-Dimethyl-cyclohexane-1,2-diamine (0.283 mmol), copper(I) iodide (1 mmol), potassium carbonate (5.4 mmol) in 10 mL dry DMF was stirred under argon and heated at 160° C. for 2 days. After cooling to room temperature, the mixture was diluted with water (100 mL) and stirred for 1 hour. Finally, the reaction mixture was extracted with ethyl acetate (100 mL), and the volatiles were removed under reduced pressure. The residue was chromatographed using silica gel and hexane/ethyl acetate (7:3) as an eluent to give 0.34 g (34% yield) of Chromophore 23 ((E)-2-(4-((4-((2-ethylhexyl)oxy)phenyl) diazenyl)phenyl)-2H-1,2,3-triazole) and give 0.19 g (19% yield) of Chromophore 24 ((E)-1-(4-((4-((2-ethylhexyl)oxy) phenyl)diazenyl)phenyl)-1H-1,2,3-triazole). The compounds were further purified by recrystallization. (E)-2-(4-((4-((2-ethylhexyl)oxy)phenyl)diazenyl)phenyl)-2H-1,2,3-triazole $^1$H-NMR (CDCl3): δ 8.23 (2H, d), 8.02 (2H, d), 7.93 (2H, d), 7.85 (2H, s), 7.02 (2H, d), 3.93 (2H, d), 1.82-1.24 (9H, m), 0.96 (6H, m). LC-MS: MH+ 378. UV-Vis in ethyl acetate 362 nm. (E)-1-(4-((4-((2-ethylhexyl)oxy) phenyl)diazenyl)phenyl)-1H-1,2,3-triazole $^1$H-NMR (CDCl3): δ 8.06 (3H, m), 7.94 (5H, m), 7.04 (2H, d), 3.94 (2H, d), 1.82-1.24 (9H, m), 0.96 (6H, m). LC-MS: MH+ 378. UV-Vis in ethyl acetate 359 nm.

Synthesis of Chromophore 25

The azo-benzene chromophore (Chromophore 25) was synthesized according to the following synthesis scheme:

A mixture of 2-ethyl-1-bromohexane (25 mmol), 4-nitrophenol (20 mmol), potassium carbonate (30 mmol), and DMF (anhydrous, 40 mL) is stirred under argon and heated at 80° C. until all nitrophenol is consumed. The reaction mixture is poured into ice/water (200 mL) and extracted with a mixture of hexane/ethyl acetate (200+200 mL). The extract is washed with water (200 mL), dried over magnesium sulfate, and the solvent is removed under reduced pressure. Around 5 grams of Intermediate I is obtained, a colorless liquid with yield nearly quantitatively. $^1$H-NMR (CDCl3): δ 8.19 (2H, d), 6.95 (2H, d), 3.92 (2H, t), 1.76 (H, m), 1.48-1.20 (8H, m), 0.90 (6H, m).

Then, Intermediate I (20 mmol) is mixed with Pd in THF and methanol. The solution is connected with a hydrogen system, and the atmosphere is exchanged several times, and then the solution is shaken for about half an hour. TLC indicated completion of the reaction. The reaction mixture was filtered through a celite packed short column, and the solvent was removed under reduced pressure. Around 3.9 grams light brownish liquid is obtained, Intermediate J, with yield nearly 90%. $^1$H-NMR (CDCl3): δ 6.72 (2H, d), 6.64 (2H, d), 3.74 (2H, t), 1.70 (H, m), 1.48-1.20 (8H, m), 0.88 (6H, m).

Then, aniline and the nitroso (Intermediate J) are added and left at room temperature to stir overnight. For workup, 0.2 L ice water is added, and ethyl acetate is used to extract three times, and then neutralized with NaHCO3. The organic phase is dried over Na2SO4, filtered and concentrated, and then run through a column. Further purification is performed by recrystallization, and then dried in a vacuum to obtain about 0.6 g of Chromophore 25, with the yield 40%. $^1$H-NMR (CDCl3): δ 7.94 (4H, d), 7.79 (2H, d), 7.02 (2H, d), 3.94 (2H, d), 1.75 (H, m), 1.48-1.32 (8H, m), 0.92 (6H, m). LC-MS: MH+ 336. UV-Vis in ethyl acetate 362 nm.

Synthesis of Chromophore 26

The azo-benzene chromophore (Chromophore 31) was synthesized according to the following synthesis scheme:

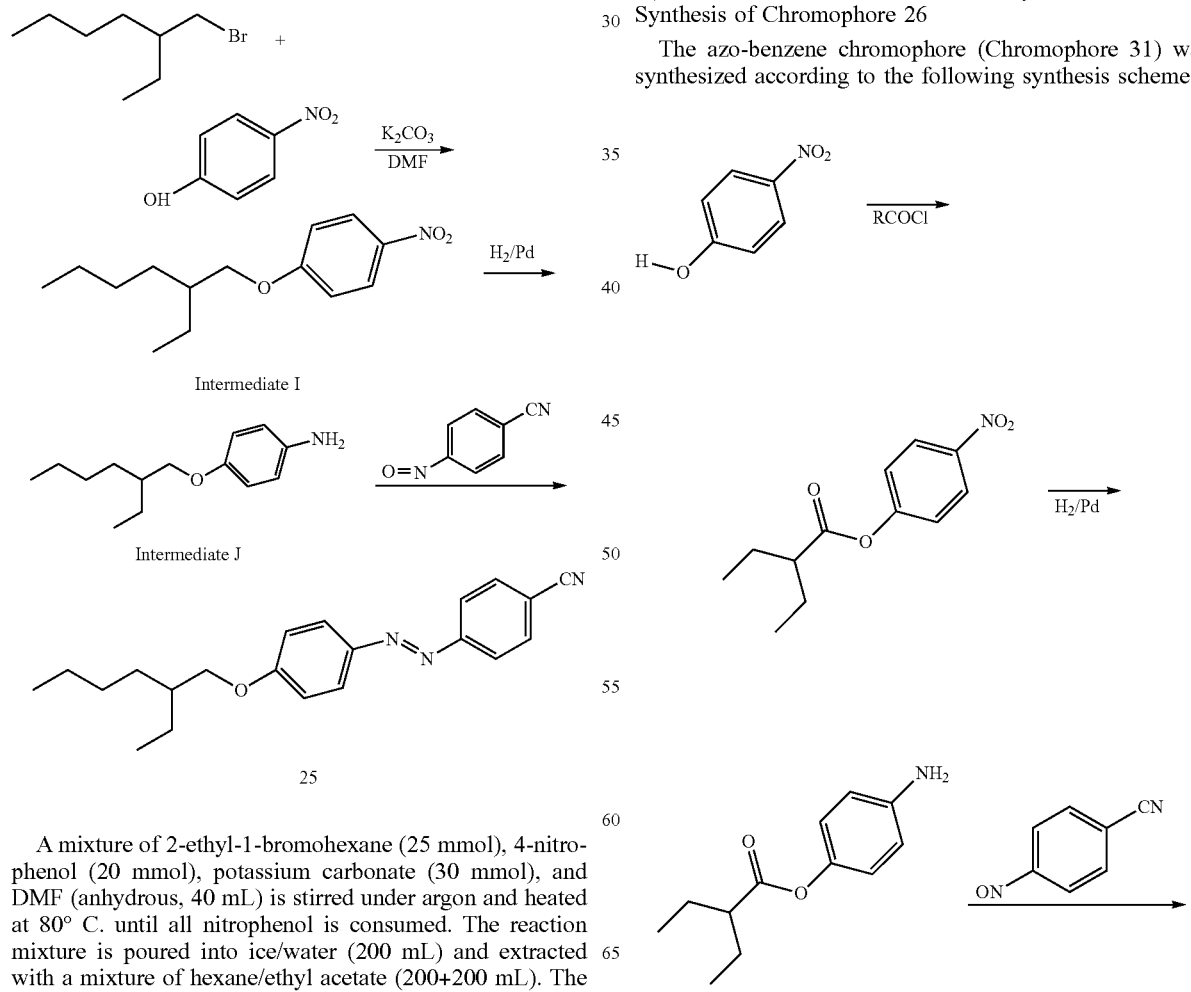

-continued

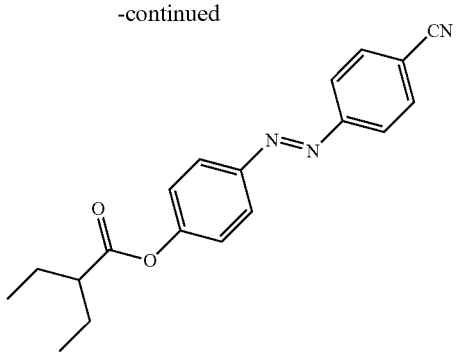

26

A mixture of 2-ethylbutanoyl chloride (25 mmol), 4-nitrophenol (20 mmol), potassium carbonate (30 mmol), and DMF (anhydrous, 40 mL) is stirred under argon and heated at 80° C. until all nitrophenol is consumed. The reaction mixture is poured into ice/water (200 mL) and extracted with a mixture of hexane/ethyl acetate (200+200 mL). The extract is washed with water (200 mL), dried over magnesium sulfate, and the solvent is removed under reduced pressure. A colorless liquid was obtained with yield nearly quantitatively. $^1$H-NMR (CDCl3): δ 8.27 (2H, d), 7.26 (2H, d), 2.49 (1H, m), 1.81-1.58 (4H, m), 1.03 (6H, t).

Then, the resulting product from the last step (20 mmol) was mixed with Pd in THF and methanol. The mixture was connected with a hydrogen system, and the atmosphere was exchanged several times, then the mixture was shaken for about half an hour. TLC showed the reaction was complete. The reaction mixture was filtered through a celite packed short column, and the solvent was removed under reduced pressure. Around 3.0 grams light brownish liquid with yield nearly quantitatively was obtained. $^1$H-NMR (CDCl3): δ 6.85 (2H, d), 6.67 (2H, d), 2.40 (1H, m), 1.81-1.58 (4H, m), 1.01 (6H, t).

Then, the resulting product from the last step was added to aniline and nitroso, and stirred at room temperature overnight. Then 0.2 L ice water was added, and ethyl acetate was used to extract three times, and then neutralized with NaHCO₃. The organic phase was dried over Na₂SO₄, filtered and concentrated, and then run through a column. Further purification was done by recrystallization, and then dried in a vacuum, to obtain Chromophore 26. $^1$H-NMR (CDCl3): δ 7.97 (4H, m), 7.82 (2H, d), 7.26 (2H, d), 2.49 (1H, m), 1.81-1.58 (4H, m), 1.06 (6H, t). LC-MS: MH+ 322. UV-Vis in EtOAc 329 nm.

Polymer Matrix Material

Polymethyl methacrylate (PMMA) was purchased from Aldrich and used as received. Liquid Crystal Liquid Crystal TL213 was purchased from Merck and used as received.

EXAMPLES

In some embodiments, the photochromic composition comprises two or more different components, including, for example, the host polymer matrix and a chromophore compound. In some embodiments, the photochromic composition includes about 95% of the host polymer and about 5% of the chromophore.

In some embodiments, photochromic device fabrication involves two steps. The first step involves chunk preparation wherein the components described herein are mixed along with a solvent in a glass container and stirred until all the contents of the vial are dissolved completely. The contents of the vial are then transferred to a preheated glass plate at 55° C. and the solvent is allowed to evaporate completely leaving a solid chunk. The resulting chunk is then melted by placing it on a preheated (150° C.) conductive oxide coated glass (substrate) slide. Glass bead spacers of known thickness are placed on the substrate and a second substrate is placed over the chunk containing substrate and pressed well to complete the photochromic device fabrication.

Example 1—Preparation of Photochromic Composition

A photorefractive composition testing sample was prepared. The components of the composition, prepared as described in the above production methods, were as follows:

| | |
|---|---|
| (i) PMMA: | 95 wt % |
| (ii) Chromophore 3: | 5 wt % |

To prepare the composition, the components listed above were dissolved in dichloromethane with stirring and then dripped onto glass plates at 60° C. using a filtered glass syringe. The resulting composites were then heated to 60° C. for five minutes and then vacuumed for five more minutes. The composites were then heated to 150° C. for five minutes and then vacuumed for 30 seconds. The composites were then scrapped off of the glass plates and cut into chunks.

Small portions of this chunk were taken off and sandwiched between 2 inch by 2 inch glass plates separated by a 100 m spacer to form the individual sample.

Measurement 1: Photoinduced Birefringence

Figure 2:
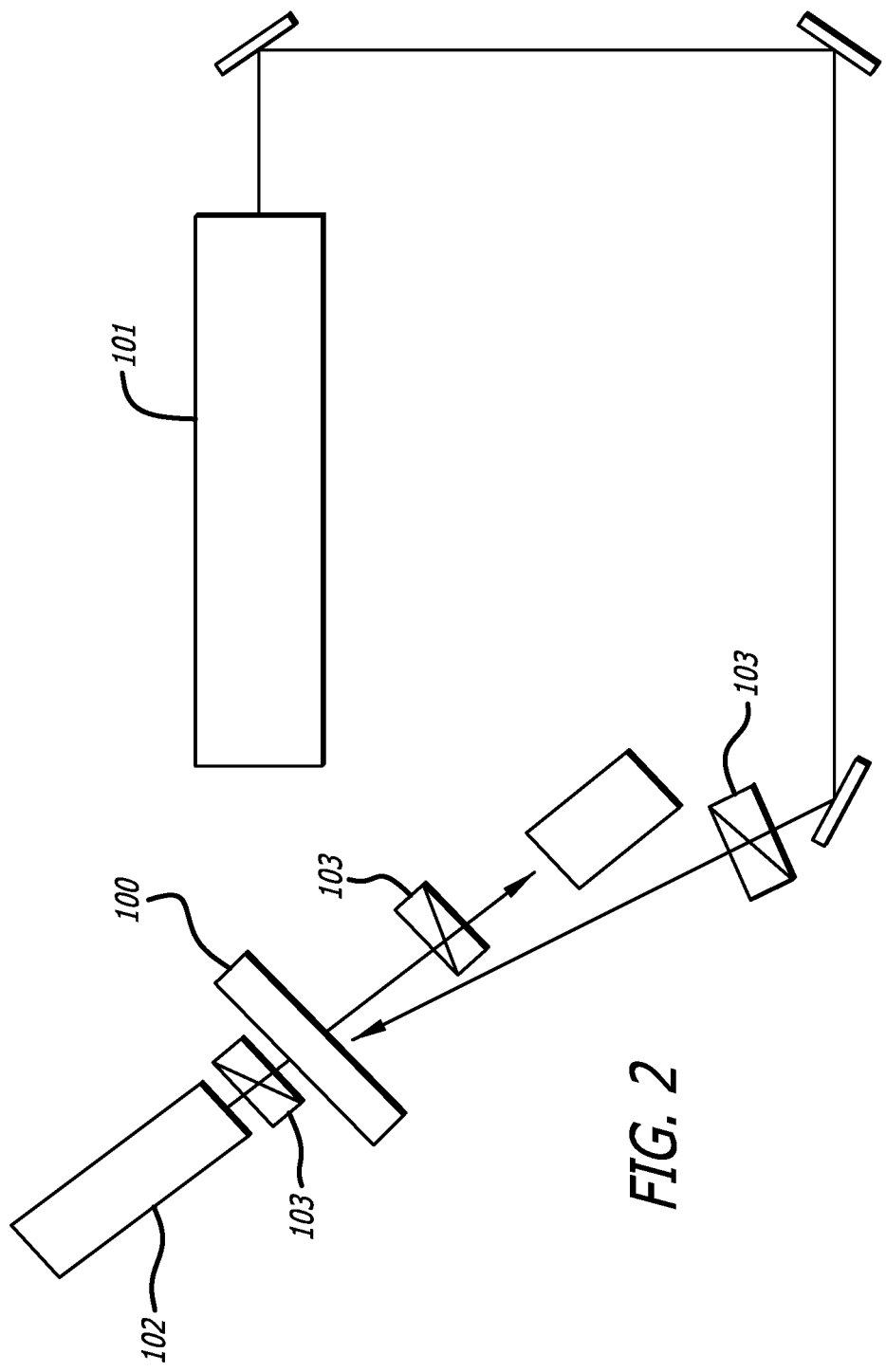
FIG. 2 is a schematic depiction illustrating a non-limiting embodiment of the optical setup for measuring the photoinduced birefringence of a photochromic composition.

The photoinduced birefringence (□n) is an important factor for a compositions holographic image display performance. Larger □n can provide better image contrast and overall display brightness. FIG. 2 is a schematic depiction illustrating a non-limiting embodiment of the optical setup for measuring the photoinduced birefringence of a photochromic device. The photochromic device 100 was irradiated with a 488 nm linearly s-polarized beam from an Ar+ laser at 200 mW/cm². The incident angle of the pumping beam 101 was fixed at 7°. The intensity of the probe beam 102 at 633 nm from a He—Ne laser transmitted through a pair of crossed polarizers 103, with the sample film between them, was measured with a photodiode. The photoinduced birefringence was estimated from the change in transmittance. All experiments were carried out at room temperature. The measured value of birefringence Δn induced in the Example 1 photochromic composition was $0.92*10^3$.

Example 2

A photochromic composition was prepared similarly to Example 1, except Chromophore 6 was used.

The measured photoinduced birefringence for the Example 2 photochromic composition was $1.34*10^{-3}$.

Example 3

A photochromic composition was prepared similarly to Example 1, except Chromophore 7 was used.

The measured photoinduced birefringence for the Example 3 photochromic composition was $1.15*10^{-3}$.

Example 4

A photochromic composition was prepared similarly to Example 1, except Chromophore 8 was used.

The measured photoinduced birefringence for the Example 4 photochromic composition was 0.96*10⁻³.

Example 5

A photochromic composition was prepared similarly to Example 1, except Chromophore 10 was used.
The measured photoinduced birefringence for the Example 5 photochromic composition was 1.70*10⁻³.

Example 6

A photochromic composition was prepared similarly to Example 1, except Chromophore 12 was used.
The measured photoinduced birefringence for the Example 6 photochromic composition was 1.68*10⁻³.

Example 7

A photochromic composition was prepared similarly to Example 1, except Chromophore 17 was used.
The measured photoinduced birefringence for the Example 7 photochromic composition was 0.70*10⁻³.

Example 8

A photochromic composition was prepared similarly to Example 1, except Chromophore 18 was used.
The measured photoinduced birefringence for the Example 8 photochromic composition was 0.96*10⁻³.

Example 9

A photochromic composition was prepared similarly to Example 1, except Chromophore 25 was used.
The measured photoinduced birefringence for the Example 9 photochromic composition was 1.22*10⁻³.

Table 1 below shows the photoinduced birefringence measurements for the Examples 1-9 devices.

TABLE 1

Comparison of the measured photoinduced birefringence for the devices of Examples 1-9.

| Example | PMMA Conc. | Chrom. | Chrom. Conc. | Liquid Crystal | Thickness ($\mu m$) | $\Delta n$ |
|---|---|---|---|---|---|---|
| Example 1 | 95 wt % | 3 | 5 wt % | None | 100 | $0.92 * 10^{-3}$ |
| Example 2 | 95 wt % | 6 | 5 wt % | None | 100 | $1.34 * 10^{-3}$ |
| Example 3 | 95 wt % | 7 | 5 wt % | None | 100 | $1.15 * 10^{-3}$ |
| Example 4 | 95 wt % | 8 | 5 wt % | None | 100 | $0.96 * 10^{-3}$ |
| Example 5 | 95 wt % | 10 | 5 wt % | None | 100 | $1.70 * 10^{-3}$ |
| Example 6 | 95 wt % | 12 | 5 wt % | None | 100 | $1.68 * 10^{-3}$ |
| Example 7 | 95 wt % | 17 | 5 wt % | None | 100 | $0.70 * 10^{-3}$ |
| Example 8 | 95 wt % | 18 | 5 wt % | None | 100 | $0.96 * 10^{-3}$ |
| Example 9 | 95 wt % | 18 | 5 wt % | None | 100 | $1.22 * 10^{-3}$ |

The data in Table 1 shows the photoinduced birefringence of the photochromic devices varies significantly with different chromophore structures. The desired photochromic properties can be tailored by varying the chromophore structure.

EMBODIMENTS

The following embodiments are provided as non-limiting examples consistent with this disclosure.

Embodiment 1

A chromophore represented by formula (I-a), (I-b), (I-c), (I-d), (I-e), or (I-f):

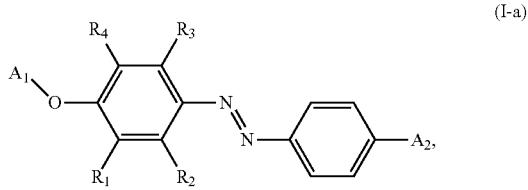

(I-a)

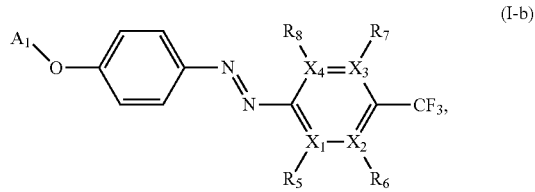

(I-b)

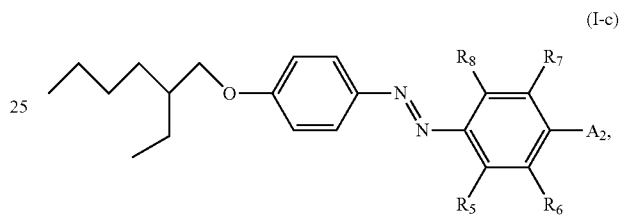

(I-c)

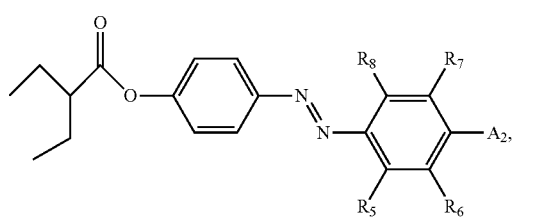

(I-d)

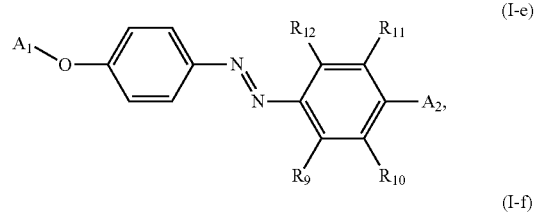

(I-e)

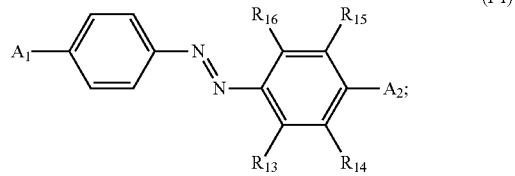

(I-f)

wherein:

$A_1$ is optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, or optionally substituted ether;

$A_2$ is —CN, —CF$_3$, or —NO$_2$;

$X_1$-$X_4$ are each independently C or N, provided that at least one of $X_1$-$X_4$ is N;

$R_1$-$R_4$ are each independently hydrogen, —F, —CN, or —$CF_3$, provided that at least one of $R_1$-$R_4$ is not hydrogen;

$R_5$-$R_8$ are each independently hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, or —$CF_3$;

$R_9$-$R_{12}$ are each independently hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, or —$CF_3$, provided that at least one of $R_9$-$R_{12}$ is not hydrogen;

and $R_{13}$-$R_{16}$ are each independently hydrogen, —F, —CN, or —$CF_3$, provided that at least one of $R_{13}$-$R_{16}$ is not hydrogen.

Embodiment 2

The chromophore of Embodiment 1, wherein $A_2$ is —CN.

Embodiment 3

The chromophore of Embodiment 1 or 2, wherein $R_1$ is —F or —$CF_3$.

Embodiment 4

The chromophore of Embodiment t 1, 2, or 3, wherein $R_2$-$R_4$ are independently hydrogen or —F.

Embodiment 5

The chromophore of Embodiment 1, 2, 3, or 4, wherein $X_1$ is N, and $R_5$-$R_8$ are hydrogen.

Embodiment 6

The chromophore of Embodiment 1, 2, 3, 4, or 5, wherein $R_9$-$R_{12}$ are independently hydrogen or alkyl.

Embodiment 7

The chromophore of Embodiment 1, 2, 3, 4, 5, or 6, wherein $R_{13}$-$R_{16}$ are independently hydrogen or —CN.

Embodiment 8

The chromophore of Embodiment 1, wherein the chromophore is:

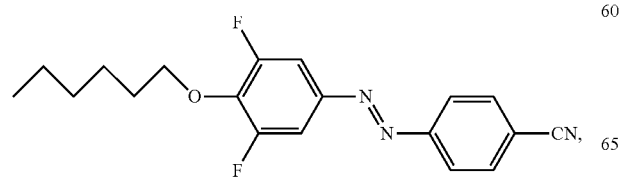

-continued

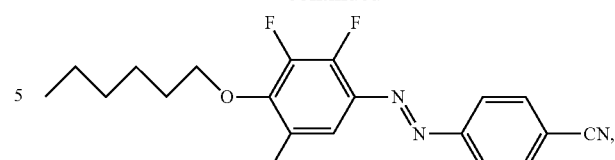

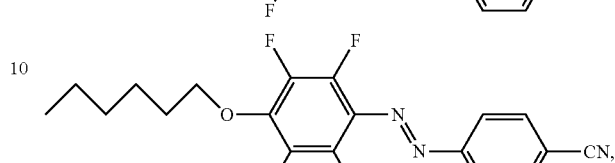

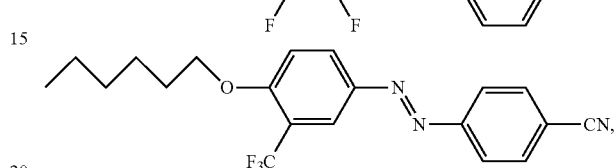

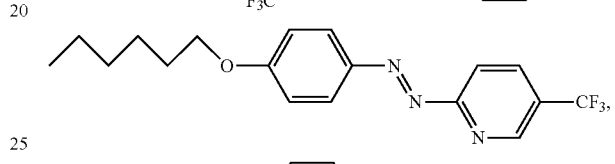

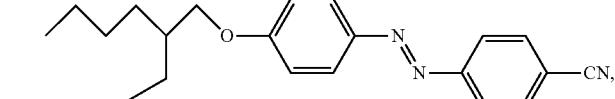

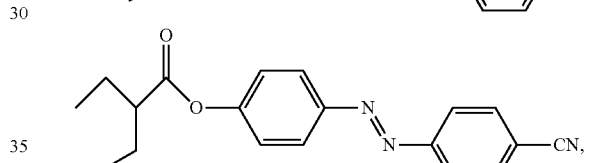

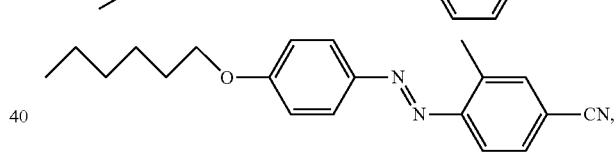

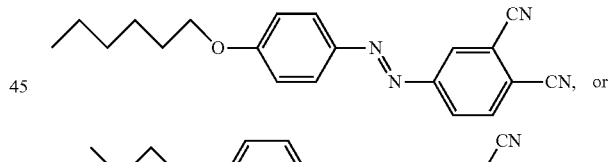

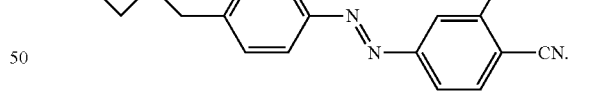

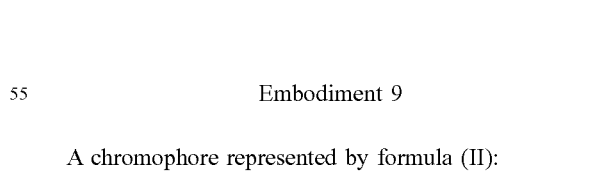

Embodiment 9

A chromophore represented by formula (II):

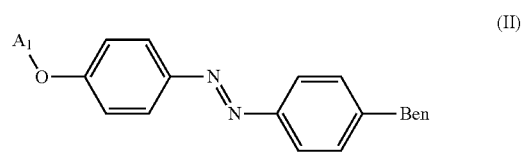

(II)

wherein Ben is

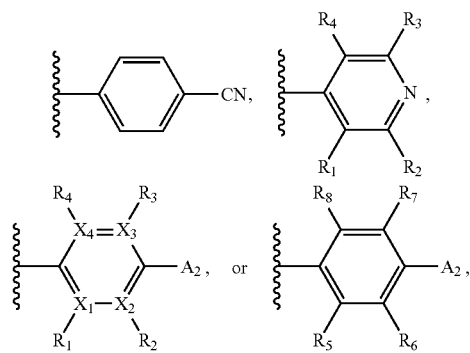

wherein:
- $A_1$ is optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, or optionally substituted ether;
- $A_2$ is —H, —F, —CN, —CF$_3$, or —NO$_2$;
- $X_1$-$X_4$ are each independently C or N, provided that at least one of $X_1$-$X_4$ is N;
- $R_1$-$R_8$ are each independently hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, or —CF$_3$, provided that at least one of $R_5$-$R_8$ is not hydrogen.

Embodiment 10

The chromophore of Embodiment 9, wherein $A_2$ is hydrogen.

Embodiment 11

The chromophore of Embodiment 9 or 10, wherein $R_1$-$R_4$ are independently hydrogen or alkyl.

Embodiment 12

The chromophore of Embodiment 9, 10, or 11, wherein $X_2$ is N.

Embodiment 13

The chromophore of Embodiment 9, 10, 11, or 12, wherein $X_2$ and $X_3$ are N.

Embodiment 14

The chromophore of Embodiment 9, 10, 11, 12, or 13, wherein $R_5$-$R_8$ are independently hydrogen

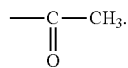

Embodiment 15

The chromophore of Embodiment 9, wherein the chromophore is:

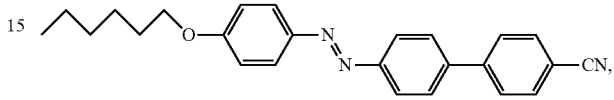

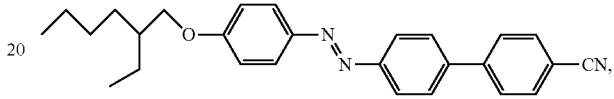

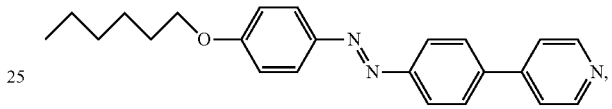

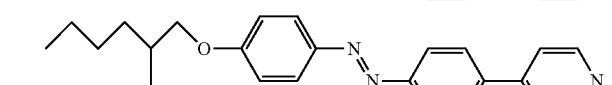

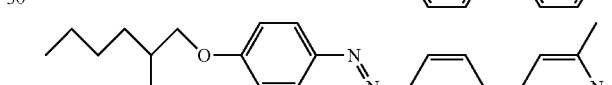

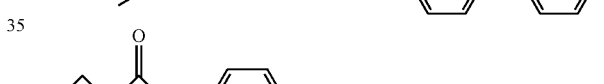

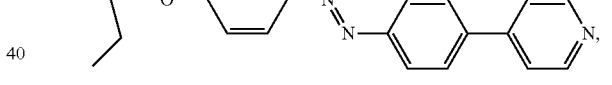

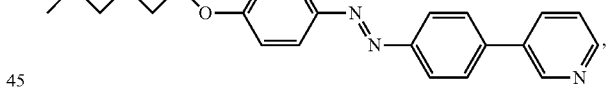

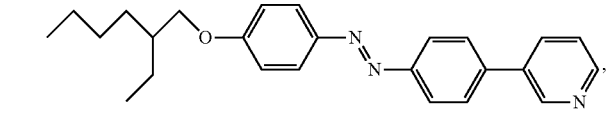

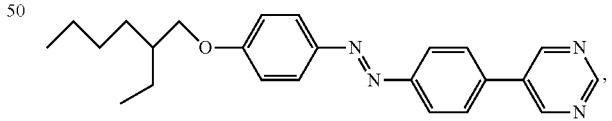

, or

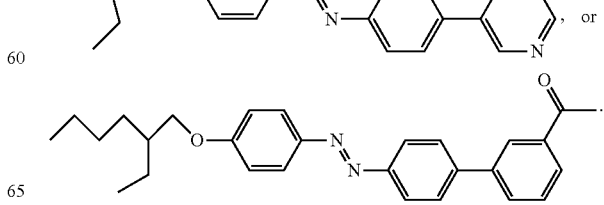

Embodiment 16

A chromophore represented by formulae (III):

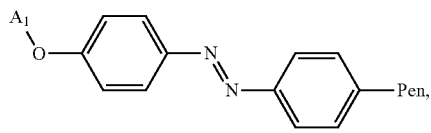

wherein Pen is

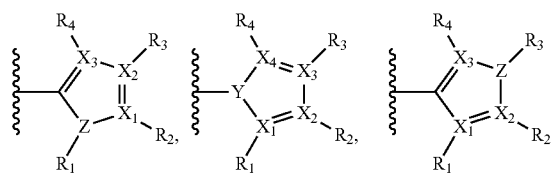

wherein:
- $A_1$ is optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, or optionally substituted ether,
- $X_1$-$X_4$ are each C or N;
- Z is S, O, C, or N;
- Y is C or N;
- $R_1$-$R_4$ are each independently hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —CN, —$CF_3$, —$NO_2$, or —Br.

Embodiment 17

The chromophore of Embodiment 16, wherein Y is N.

Embodiment 18

The chromophore of Embodiment 16 or 17, wherein $R_1$-$R_4$ are independently hydrogen or alkyl.

Embodiment 19

The chromophore of Embodiment 16, 17, or 18, wherein Z is N or O.

Embodiment 20

The chromophore of Embodiment 16, 17, 18, or 19, wherein at least one of $X_1$-$X_3$ is N.

Embodiment 21

The chromophore of Embodiment 16, wherein the chromophore is:

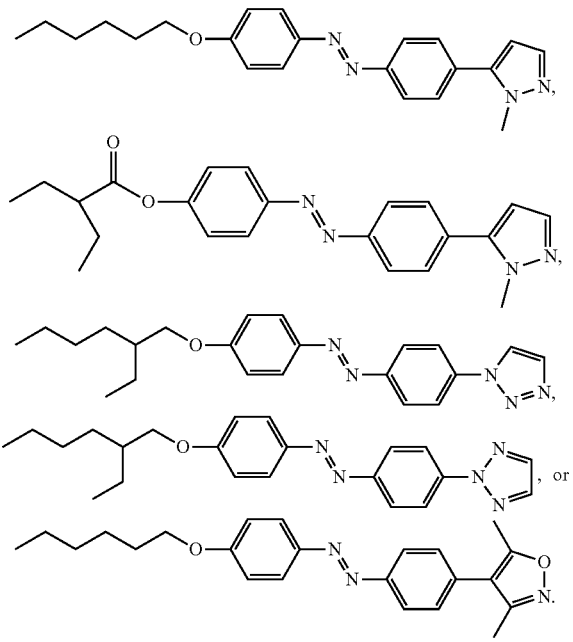

Embodiment 22

The chromophore of Embodiment 1, 2, 3, 4, 5, 6, 7, 9, 10, 11, 12, 13, 14, 16, 17, 18, 19, or 20, wherein $A_1$ is —$H_2C$—$CH_2$—$CH_2$—$CH_2$—$CH_2$—$CH_3$—$CH_2$—$CH_2$—$CH_2$—$CH_3$, —$H_2C$—CH—$CH_2$—$CH_2$—$CH_2$—$CH_3$, or
        |
       $CH_2$
       |
       $CH_3$

—C—CH—$CH_2$—$CH_3$.
 ||  |
 O  $CH_2$
     |
    $CH_3$

Embodiment 23

A photochromic composition comprising an optically transparent polymer matrix and a chromophore of Embodiment 1, 2, 3, 4, 5, 6, 7, 8, 9, 10, 11, 12, 13, 14, 15, 16, 17, 18, 19, 20, 21, or 22.

Embodiment 24

The photochromic composition of Embodiment 23, wherein the composition is configured to be photoresponsive upon irradiation by first laser having a first wavelength in the visible light spectrum, and wherein the first laser is selected from a blue laser, a green laser, and a red laser.

Embodiment 25

The photochromic composition of Embodiment 23 or 24, wherein two or more chromophores are mixed within the composition.

Embodiment 26

The photochromic composition of Embodiment 23, 24, or 25, wherein the chromophore is present in the composition in an amount in the range of about 0.01 wt % to about 30 wt %.

Embodiment 27

The photochromic composition of Embodiment 23, 24, 25, or 26, wherein the chromophore is present in the composition in an amount in the range of about 1 wt % to about 15 wt %.

Embodiment 28

The photochromic composition of Embodiment 23, 24, 25, 26, or 27, wherein the polymer matrix comprises a repeating unit that includes a moiety represented by the following formula (IV):

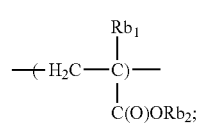

wherein $Rb_1$ and $Rb_2$ are independently hydrogen, $C_1$-$C_{10}$ alkyl, $C_1$-$C_{10}$ alkenyl, or $C_6$-$C_{10}$ aryl.

Embodiment 29

The photochromic composition of Embodiment 23, 24, 25, 26, 27, or 28, wherein the polymer matrix is formed from polyethylene terephthalate, polyacrylate, polymethacrylate, polyvinyl carbazole, polymethyl methacrylate, polyvinyl butyral, ethylene vinyl acetate, ethylene tetrafluoroethylene, polyimide, amorphous polycarbonate, polystyrene, siloxane sol-gel, polyurethane, or any combination thereof.

Embodiment 30

The photochromic composition of Embodiment 23, 24, 25, 26, 27, 28, or 29, wherein the chromophore may be doped into the polymer matrix such that the polymer and the chromophore are not chemically bonded.

Embodiment 31

The photochromic composition of Embodiment 23, 24, 25, 26, 27, 28, 29, or 30, wherein one or more of the chromophore compounds is covalently bonded to the polymer matrix.

Embodiment 32

The photochromic composition of Embodiment 31, wherein free radical polymerization is used to covalently bond the polymer matrix and the chromophore together.

Embodiment 33

The photochromic composition of Embodiment 32, further comprising a component to induce polymerization selected from the group consisting of an initiator, a cross-linking agent, or any combination thereof.

Embodiment 34

The photochromic composition of Embodiment 23, 24, 25, 26, 27, 28, 29, 30, 31, 32, or 33, further comprising a liquid crystal.

Embodiment 35

The photochromic composition of Embodiment 23, 24, 25, 26, 27, 28, 29, 30, 31, 32, 33, or 34, wherein the composition is configured to be photoresponsive upon irradiation by a first laser having a first wavelength in the visible light spectrum and a second laser having a second wavelength in the visible light spectrum, wherein the first wavelength is different from the second wavelength and wherein the first and second lasers are selected from a blue laser, a green laser, and a red laser.

Embodiment 36

The photochromic composition of Embodiment 35, wherein the composition is photoresponsive upon irradiation with a third laser having a third wavelength in the visible light spectrum, such that the third laser has a wavelength that is different from that of the first laser and the second laser, wherein the third laser is selected from a blue laser, a green laser, and a red laser.

Embodiment 37

The composition of Embodiment 23, 24, 25, 26, 27, 28, 29, 30, 31, 32, 33, 34, 35, or 36, wherein the blue laser has a wavelength of about 488 nm, the green laser has a wavelength of about 532 nm, and the red laser has a wavelength of about 633 nm.

Embodiment 38

The composition of Embodiment 23, 24, 25, 26, 27, 28, 29, 30, 31, 32, 33, 34, 35, or 36, wherein the blue laser has a wavelength of about 457 nm, the green laser has a wavelength of about 532 nm, and the red laser has a wavelength of about 633 nm.

Embodiment 39

An optical device that comprises the photochromic composition according to Embodiments 23, 24, 25, 26, 27, 28, 29, 30, 31, 32, 33, 34, 35, 36, 37, or 38.

All literature references and patents mentioned herein are hereby incorporated in their entireties. Although the foregoing invention has been described in terms of certain preferred embodiments, other embodiments will become apparent to those of ordinary skill in the art in view of the disclosure herein without departing from the scope of the invention. Accordingly, all such modifications and changes are intended to fall within the scope of the invention, as defined by the appended claims.

What is claimed is:

1. A chromophore represented by for Lila (III):

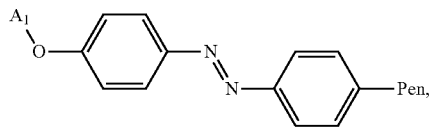

wherein Pen is

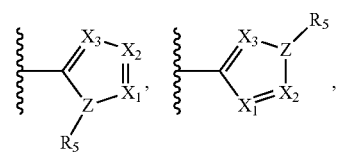

wherein;

$A_1$ is optionally substituted alkyl, optionally substituted alkenyl, optionally substituted heteroalkyl, or optionally substituted carbonyl;

$X_1$ is $CR_1$ or N, $X_2$ is $CR_2$ or N, $X_3$ is $CR_3$ or N, $X_4$ is $CR_4$ or N;

$R_1$-$R_4$ are each independently hydrogen, optionally substituted alkyl, optionally substituted alkenyl, optionally substituted heteroalkyl, optionally substituted amido, optionally substituted alkoxy, optionally substituted carbonyl, and optionally substituted carboxy, optionally substituted aryloxy, optionally substituted acyloxy, optionally substituted ketone, optionally substituted ester, optionally substituted ether, —F, —ON, —$CF_3$, —$NO_2$, or —Br;

$R_5$ is hydrogen, optionally substituted alkyl, optionally substituted alkenyl, optionally substituted heteroalkyl, optionally substituted carbonyl, optionally substituted ketone, —F, —ON, —$CF_3$, —$NO_2$, or —Br, wherein Z is N or O.

2. The chromophore of claim 1, wherein $R_1$-$R_4$ are independently hydrogen or alkyl.

3. The chromophore of claim 1, wherein at least one of $X_1$-$X_3$ is N.

4. The chromophore of claim 1, wherein the chromophore is A or B or C:

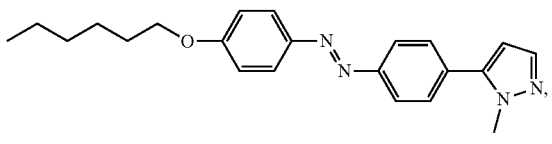

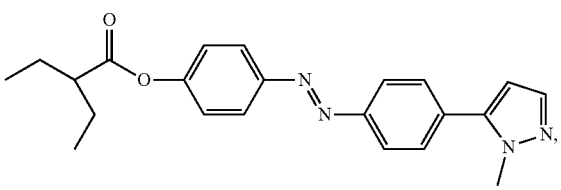

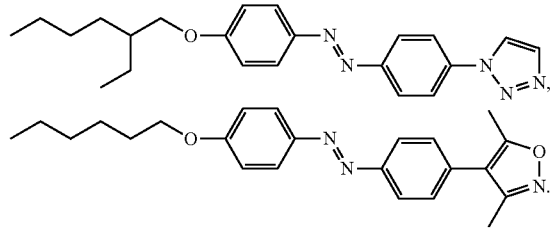

5. The chromophore of claim 1, wherein $A_1$ is —$H_2C$—$CH_2$—$CH_2$—$CH_2$—$CH_2$—$CH_3$, —$CH_2$—$CH_2$—$CH_2$—$CH_3$,

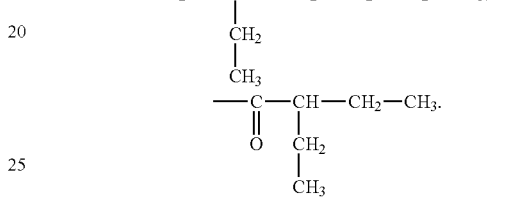

6. A photochromic composition comprising an optically transparent polymer matrix and the chromophore of claim 1.

7. The photochromic composition of claim 6, wherein the composition is configured to be photoresponsive upon irradiation by first laser having a first wavelength in the visible light spectrum, and wherein the first laser is selected from the group consisting of a blue laser, a green laser, and a red laser.

8. The photochromic composition of claim 6, wherein two or more chromophores are mixed within the composition.

9. The photochromic composition of claim 6, wherein the chromophore is present in the composition in an amount in the range of about 0.01 wt % to about 30 wt %.

10. The photochromic composition of claim 6, wherein the chromophore is present in the composition in an amount in the range of about 1 wt % to about 15 wt %.

11. The photochromic composition of claim 6, wherein the polymer matrix comprises a repeating unit that includes a moiety represented by the following formula (IV):

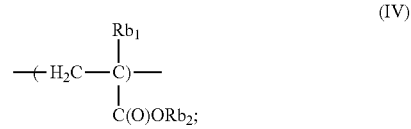

wherein $Rb_1$, and $Rb_2$ are independently hydrogen, $C_1$-$C_{10}$ alkyl, $C_1$-$C_{10}$ alkenyl, or $C_6$-$C_{10}$ aryl.

12. The photochromic composition of claim 6, wherein the polymer matrix is formed from polyethylene terephthalate, polyacrylate, polymethacrylate, polyvinyl carbazole, polymethyl methacrylate, polyvinyl butyral, ethylene vinyl acetate, ethylene tetrafluoroethylene, polyimide, amorphous polycarbonate, polystyrene, siloxane sol-gel, polyurethane, or any combination thereof.

13. The photochromic composition of claim 6, wherein the chromophore may be doped into the polymer matrix such that the polymer and the chromophore are not chemically bonded.

14. The photochromic composition of claim 6, wherein one or more of the chromophore compounds is covalently bonded to the polymer matrix.

15. The photochromic composition of claim 6, wherein the composition is configured to be photoresponsive upon irradiation by a first laser having a first wavelength in the visible light spectrum and a second laser having a second wavelength in the visible light spectrum, wherein the first wavelength is different from the second wavelength and wherein the first and second lasers are selected from the group consisting of a blue laser, a green laser, and a red laser.

16. The photochromic composition of claim 15, wherein the composition is photoresponsive upon irradiation with a third laser having a third wavelength in the visible light spectrum, such that the third laser has a wavelength that is different from that of the first laser and the second laser, wherein the third laser is selected from the group consisting of a blue laser, a green laser, and a red laser.

17. The photochromic composition of claim 16, wherein the blue laser has a wavelength of about 488 nm or about 457 nm, the green laser has a wavelength of about 532 nm, and the red laser has a wavelength of about 633 nm.

18. An optical device that comprises the photochromic composition according to claim 6.

* * * * *